(12) United States Patent
Louette et al.

(10) Patent No.: US 9,945,867 B2
(45) Date of Patent: Apr. 17, 2018

(54) ANALYTE MASS SPECTROMETRY QUANTITATION USING A UNIVERSAL REPORTER

(71) Applicant: Thermo Fisher Scientific GMBH, Dreieich (DE)

(72) Inventors: Joel Louette, Ulm (DE); John Charles Rogers, Rockton, IL (US); Scott M. Peterman, Grimes, IA (US); Bruno Domon, Strassen (LU); Elodie Duriez, Arlon (BE)

(73) Assignee: Thermo Fisher Scientific GmbH, Dreieich (DE)

( * ) Notice: Subject to any disclaimer, the term of this patent is extended or adjusted under 35 U.S.C. 154(b) by 0 days.

(21) Appl. No.: 14/927,586

(22) Filed: Oct. 30, 2015

(65) Prior Publication Data

US 2016/0097749 A1   Apr. 7, 2016

Related U.S. Application Data

(60) Continuation of application No. 14/579,206, filed on Dec. 22, 2014, now Pat. No. 9,377,469, which is a (Continued)

(51) Int. Cl.
*G01N 30/72* (2006.01)
*H01J 49/00* (2006.01)
(Continued)

(52) U.S. Cl.
CPC ......... *G01N 33/6848* (2013.01); *B82Y 15/00* (2013.01); *C07K 2/00* (2013.01); *G01N 30/7233* (2013.01); *G01N 30/8665* (2013.01); *G01N 30/8675* (2013.01); *G01N 33/532* (2013.01); *G01N 33/68* (2013.01); *H01J 49/0009* (2013.01); *H01J 49/0031* (2013.01); *H01J 49/0036* (2013.01); *G01N 2458/15* (2013.01);
(Continued)

(58) Field of Classification Search
USPC .... 250/281, 282, 288, 526; 435/23, 24, 183, 435/188; 436/174, 175, 176, 183; 530/300, 350, 355; 73/61.55
See application file for complete search history.

(56) References Cited

U.S. PATENT DOCUMENTS 7,396,688 B2    7/2008  Estell et al.
7,501,286 B2 *  3/2009  Gygi ................. G01N 33/68
                                                436/173
(Continued)

FOREIGN PATENT DOCUMENTS

WO   WO 2002/071066       9/2002
WO       03/016861 A2     2/2003
(Continued)

OTHER PUBLICATIONS

U.S. Appl. No. 14/579,206, filed Dec. 22, 2014.
(Continued)

*Primary Examiner* — Bernard Souw
(74) *Attorney, Agent, or Firm* — McNeill Baur PLLC

(57) ABSTRACT

Quantitation of analytes, including but not limited to peptides, polypeptides, and proteins, in mass spectrometry using a labeled peptide coupled to a reporter, and a universal reporter.

4 Claims, 35 Drawing Sheets

Related U.S. Application Data division of application No. 13/805,059, filed as application No. PCT/US2011/043159 on Jul. 7, 2011, now Pat. No. 8,933,396, which is a continuation-in-part of application No. PCT/US2011/038629, filed on May 31, 2011.

(60) Provisional application No. 61/361,970, filed on Jul. 7, 2010.

(51) Int. Cl.
    *B82Y 15/00* (2011.01)
    *G01N 33/68* (2006.01)
    *G01N 33/532* (2006.01)
    *C07K 2/00* (2006.01)
    *G01N 30/86* (2006.01)

(52) U.S. Cl.
    CPC ...... *Y10T 436/25* (2015.01); *Y10T 436/25125* (2015.01)

(56) References Cited

U.S. PATENT DOCUMENTS

| | | | | |
|---|---|---|---|---|
| 7,632,686 B2* | 12/2009 | Anderson | ........... | G01N 33/6848 435/173.7 |
| 7,693,665 B2* | 4/2010 | Zhu | .................... | G01N 33/6812 250/281 |
| 7,786,086 B2* | 8/2010 | Reches | ................... | A61L 27/56 514/1.1 |
| 7,901,942 B2* | 3/2011 | Kamiie | ............... | G01N 30/7266 435/23 |
| 7,939,331 B2 | 5/2011 | Leite et al. | | |
| 8,017,739 B2 | 9/2011 | Eichner et al. | | |
| 8,933,396 B2 | 1/2015 | Louette et al. | | |
| 8,940,546 B2 | 1/2015 | Grothe, Jr. et al. | | |
| 9,252,003 B2* | 2/2016 | Hermanson | ............ | G01N 33/60 |
| 9,274,124 B2* | 3/2016 | Anderson | .......... | G01N 33/6848 |
| 9,297,808 B2 | 3/2016 | Louette et al. | | |
| 9,366,678 B2* | 6/2016 | Coon | ................. | G01N 33/6848 |
| 9,377,469 B2* | 6/2016 | Louette | .................. | B82Y 15/00 |
| 2004/0033530 A1* | 2/2004 | Awrey | ............... | G01N 33/6848 435/7.1 |
| 2004/0072251 A1* | 4/2004 | Anderson | .......... | G01N 33/6848 435/7.1 |
| 2006/0210978 A1* | 9/2006 | Shokat | ..................... | C12N 9/54 435/6.14 |
| 2006/0246531 A1* | 11/2006 | Shokat | ..................... | C07K 14/47 435/23 |
| 2007/0260040 A1* | 11/2007 | Sharma | ................ | C07D 403/04 530/333 |
| 2009/0060930 A1* | 3/2009 | Mautino | ............ | A61K 39/0011 424/185.1 |
| 2011/0177491 A1* | 7/2011 | Kamiie | ............... | G01N 33/6848 435/4 |
| 2012/0021446 A1* | 1/2012 | Ohtsuki | ................... | C07K 7/06 435/23 |
| 2012/0305762 A1* | 12/2012 | Kaneko | ................ | H01J 49/427 250/283 |
| 2013/0105684 A1 | 5/2013 | Louette et al. | | |
| 2013/0210051 A1* | 8/2013 | Louette | .................. | B82Y 15/00 435/23 |
| 2014/0158881 A1* | 6/2014 | Cooper | ............... | H01J 49/0009 250/282 |
| 2014/0230517 A1* | 8/2014 | Coon | .................. | G01N 30/8665 73/1.02 |
| 2014/0255966 A1* | 9/2014 | Ohtsuki | ............. | G01N 33/6848 435/23 |
| 2016/0139140 A1* | 5/2016 | Thompson | ........... | C07D 403/12 506/4 |
| 2016/0154006 A1* | 6/2016 | Hermanson | ............ | G01N 33/60 506/12 |

FOREIGN PATENT DOCUMENTS

| | | |
|---|---|---|
| WO | 03/046148 A2 | 6/2003 |
| WO | WO 2003/078962 | 9/2003 |
| WO | WO 2004/031730 | 4/2004 |
| WO | WO 2011/116028 | 9/2011 |
| WO | WO 2012/170549 | 12/2012 |
| WO | WO 2014/066117 | 5/2014 |
| WO | WO 2014/184320 | 11/2014 |

OTHER PUBLICATIONS

International Preliminary Report on Patentability for PCT/US2011 /043159 issued Jan. 8, 2013, 10 pages.
International Search Report and Written Opinion for PCT/US2011/043159 mailed Mar. 27, 2012, 18 pages.
(D2) Henke et al. Absolute SILAC for Accurate Quantitation of Proteins in Complex Mixtures Down to Attomole Level. Journal of Proteome Research 7 (2008), pp. 1118-1130.
Kim et al. Biomarker Detection and Quantification in Bodily Fluids Using Concatenated Reference Peptides Including a Universal Reporter. HUPO (Sep. 4-7, 2011) 3 pages.
Kim et al. Novel proteomics approach for absolute quantification using polypeptides containing a reporter as internal standards, ASMS (Jun. 5-9, 2011) 3 pages.
Krokhin et al. An Improved Model for Prediction of Retention Times of Tryptic Peptides in Ion Pair Reversed-phase HPLC, Molecular and Cellular Proteomics 3.9 (2004 ), pp. 908-919.
(D3) Ong et al. Stable Isotope Labeling by Amino Acids in Cell Culture, SILAC, as a Simple and Accurate Approach to Expression Proteomics. Molecular & Cellular Proteomics 1.5 (2002), pp. 376-386.
Spicer et al. Sequence-Specific Retention Calculator. A Family of Peptide Retention Time Prediction Algorithms in Reversed-Phase HPLC: Applicability to Various Chromatographic Conditions and Columns. Analytical Chemistry 79 (2007) 8762-8768.
Bystrom, et al., "Plasma Renin Activity by LC-MS/MS: Development of a Prototypical Clinical Assay Reveals a Subpopulation of Human Plasma Samples with Substantial Peptidase Activity," Clinical Chemistry, 2010, 56(10): 1561-1569.
Desiderio, "Mass Spectrometric Analysis of Neuropeptidergic Systems in the Human Pituitary and Cerebrospinal Fluid," Journal of Chromatography B, 1999, 731:3-22.
Partial European Search Report dated Dec. 2, 2016, from corresponding European Patent Application No. 14806982.6, (corresponding to PCT/US2014/041208), 7 pages.
Extended European Search Report dated Mar. 23, 2017, from European Patent Application No. 14806982.6 (corresponding to PCT/US2014/041208), 16 pages.

* cited by examiner

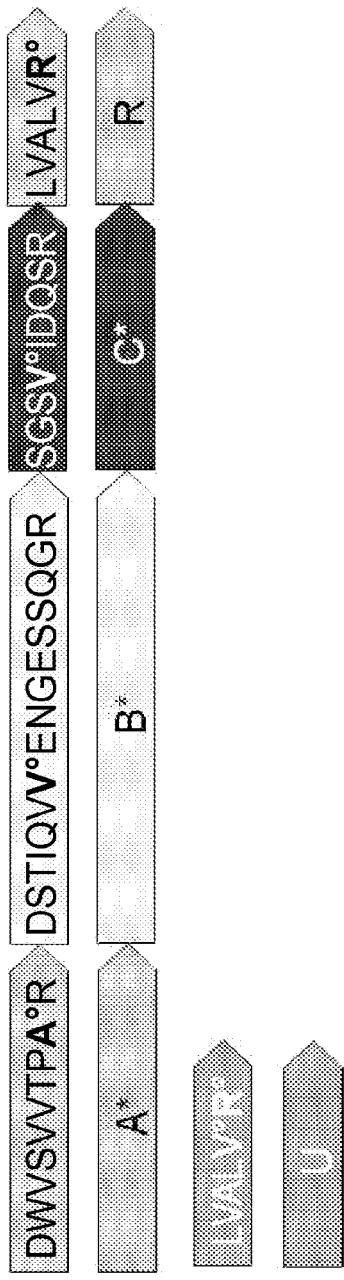

Bfc = flanking aa sequence on c-terminal side of the endogenous peptide B
Cfc = flanking aa sequence on c-terminal side of the endogenous peptide C
Afn = flanking aa sequence on n-terminal side of the endogenous peptide A
Bfn = flanking aa sequence on n-terminal side of the endogenous peptide B

| Reconstitution volume | Low amol/µl | | | | | | | High amol/µl |
|---|---|---|---|---|---|---|---|---|
| | A | B | C | D | E | F | G | H |
| 900 µl | 3 | 9 | 27 | 81 | 243 | 729 | 2187 | 6561 |
| 300 µl | 9 | 27 | 81 | 243 | 729 | 2187 | 6561 | 19683 |
| 180 µl | 15 | 45 | 135 | 405 | 1215 | 3645 | 10935 | 32805 |
| 90 µl | 30 | 90 | 270 | 810 | 2430 | 7290 | 21870 | 65610 |
| 45 µl | 60 | 180 | 540 | 1620 | 4860 | 14580 | 43740 | 131220 |

FIG. 17

|   | amol/45µl |
|---|---|
| A | 2,700 |
| B | 8,100 |
| C | 24,300 |
| D | 72,900 |
| E | 218,700 |
| F | 656,100 |
| G | 1,968,300 |
| H | 5,904,900 |
| Sorbitol | 50 mmolar |

FIG. 18

|   | amol/45µl | Isomers sequences | Δ u vs. A |
|---|---|---|---|
| A | 2,700 | LVALVR | 40 |
| B | 8,100 | LVALVR | 33 |
| C | 24,300 | LVALVR | 28 |
| D | 72,900 | LVALVR | 24 |
| E | 218,700 | LVALVR | 20 |
| F | 656,100 | LVALVR | 16 |
| G | 1,968,300 | LVALVR | 4 |
| H | 5,904,900 | LVALVR | -- |

Large bold = heavy AA

FIG. 19

| amol/45µl | Isomers sequences | Δ u vs. A |
|---|---|---|
| 218,700 | LVALVR | 40 |
| 5,904,900 | LVALVR | 33 |

Large bold = heavy AA

| Targeted protein | Peptide | SRM transitions | | | | Actual concentration measured | |
|---|---|---|---|---|---|---|---|
| | | z(Q1) | Q1 | | Q3 | | |
| | | | | | | fmol of peptide | Protein (ng/mL) |
| Fatty acid-binding protein, adipocyte (FABP4) | EVGVGFATR* (SEQ ID NO. 90) | 2 | 473.3 | 357.2 | 561.0 | 717.4 | 84.4 | 1.2 |
| | Universal reporter A* | 2 | 626.3 | 752.4 | 851.4 | 1051.6 | | |
| Fatty acid-binding protein, adipocyte (FABP4) | EVGVGFATR* (SEQ ID NO. 90) | 2 | 338.7 | 381.2 | 480.3 | 579.4 | 85.4 | 1.3 |
| | Universal reporter B* | 2 | 340.8 | 397.3 | 468.3 | 567.4 | | |
| Insulin-like growth factor binding protein 7 (IBP7) | HEVTGWVLVSPLSK (SEQ ID NO. 91) | 2 | 780.4 | 452.3 | 539.3 | 1293.8 | 51.2 | 1.5 |
| | Universal reporter B* | 2 | 340.8 | 397.3 | 468.3 | 567.4 | | |
| Insulin-like growth factor binding protein 7 (IBP7) | ITVVDALHEIPVK (SEQ ID NO. 92) | 2 | 721.4 | 351.2 | 730.4 | 1029.6 | 58.0 | 1.7 |
| | Universal reporter B* | 2 | 340.8 | 397.3 | 468.3 | 567.4 | | |

FIG. 24

| Targeted human protein | Sequence of the isotopically labeled polypeptides and the reporter | |
|---|---|---|
| | Selected proteotypic peptides and reporter peptide | |
| Uromodulin (UROM) | UROM-A | DWVSVVTPAR + (SEQ ID NO. 49) |
| | UROM-B | DSTIQVVENGESSQGR + (SEQ ID NO. 50) |
| | UROM-C | SGSVIDQSR + (SEQ ID NO. 51) |
| | Reporter Peptide | LVALVR (SEQ ID NO. 52) |
| Kininogen-1 (KNG-1) | KNG1-A | TVGSDTFYSFK + (SEQ ID NO. 70) |
| | KNG1-B | YFIDFVAR + (SEQ ID NO. 71) |
| | KNG1-C | YNSQNQSNNQFVLYR + (SEQ ID NO. 72) |
| | Reporter Peptide | LVALVR (SEQ ID NO. 52) |
| Alpha-N-acetyglucosaminidase (ANAG) | ANAG-A | LLLTSAPSLATSPAFR + (SEQ ID NO. 74) |
| | ANAG-B | YDLLDLTR + (SEQ ID NO. 75) |
| | ANAG-C | SDVFEAWR + (SEQ ID NO. 76) |
| | Reporter Peptide | LVALVR (SEQ ID NO. 52) |

FIG. 26A

| URP (SEQ ID NO. 52) | fmol/μL | [M+2H]²⁺ | Transition 1 | Transition 2 | Transition 3 |
|---|---|---|---|---|---|
| LVALVR | 0.01 | 335.73 | 173.12 | 458.31 | 557.38 |
| LVALVR | 0.03 | 337.74 | 173.12 | 462.32 | 561.38 |
| LVALVR | 0.09 | 340.74 | 183.13 | 468.32 | 567.39 |
| LVALVR | 0.27 | 343.75 | 183.13 | 474.33 | 573.40 |
| LVALVR | 0.81 | 347.25 | 183.13 | 481.35 | 580.42 |
| LVALVR | 2.43 | 349.26 | 183.13 | 486.35 | 584.22 |
| LVALVR | 7.29 | 352.26 | 183.13 | 486.35 | 590.44 |
| LVALVR | 21.87 | 355.77 | 183.13 | 495.35 | 599.44 |

| Protein name | MM (Da) | Peptide sequence | Limit of detection Peptide [amol] | Limit of quantification Peptide [amol] | Actual concentration measured Peptide [amol] | Actual concentration measured Protein [µg/mL] |
|---|---|---|---|---|---|---|
| Kininogen-1 (KNG1) | 71,957 | TVGSDTFYSFK (SEQ ID NO. 70) | 18 | 54 | 198 | 14.2 |
| | | YFIDFVAR (SEQ ID NO. 71) | 54 | 162 | 224 | 16.1 |
| | | YNSQNQSNNQFVLYR (SEQ ID NO. 72) | 18 | 54 | 185 | 13.3 |
| Alpha-N-acetyglucosamidase (ANAG) | 82,167 | LLLTSAPSLATSPAFR (SEQ ID NO. 74) | 54 | 162 | 2 | 0.2 |
| | | YDLLDLTR (SEQ ID NO. 75) | 162 | 486 | 5 | 0.5 |
| | | SDVFEAWR (SEQ ID NO. 76) | 18 | 54 | 1 | 0.1 |
| Uromodulin (UROM) | 69,761 | DWVSVVTPAR (SEQ ID NO. 49) | 162 | 486 | 1065 | 74.3 |
| | | DSTIQVVENGESSQGR (SEQ ID NO. 50) | 2 | 162 | 483 | 33.7 |
| | | SGSVIDQSR (SEQ ID NO. 51) | 54 | 162 | 250 | 17.5 |

FIG. 29

ANALYTE MASS SPECTROMETRY QUANTITATION USING A UNIVERSAL REPORTER

This application is a continuation of U.S. Ser. No. 14/597,206 filed Dec. 22, 2014, which is a divisional of U.S. Ser. No. 13/805,059 filed December 18, now U.S. Pat. No. 8,933,396; which is a national stage of PCT/US2011/043159 filed Jul. 7, 2011 and PCT/US2011/038629 filed May 31, 2011; and U.S. Application Ser. No. 61/361,970 filed Jul. 7, 2010, each of which is expressly incorporated by reference herein in its entirety.

Mass spectrometry (MS), in conjunction with internal standard peptides labeled or modified with stable heavy isotopes resulting in a heavy isotope labeled sequence or, stated differently, a sequence modified with a stable heavy isotope, provides fast, accurate and precise absolute quantitation of peptides, polypeptides, and proteins in biological and other samples. This method is based on isotopic dilution mass spectrometry (IDMS), also known as AQUA (WO 03/016861).

IDMS has limitations, as discussed below. Improvements such as the inventive method are thus desirable.

The inventive method resulted in absolute quantification of analytes by MS, and enabled a simple concentration calibration of analytes in reference solutions. The method used a heavy isotope labeled analyte (internal standard) that is in equimolar concentration with, and that is cleavably coupled to, a reporter R (that may or may not be heavy isotope labeled); and a heavy isotope labeled universal reporter U. Analytes include, but are not limited to, peptides, polypeptides, and proteins, and may be RNAi, DNA, and lipids. Universal reporter U includes, but is not limited to, peptides (i.e., polymers of amino acids) and other polymers.

In one embodiment the inventive method resulted in absolute quantification of peptide, polypeptide, and proteins analytes by MS. The method used a heavy isotope labeled peptide (proteotypic peptide, described below; internal standard) that was present in equimolar concentration with, and was cleavably coupled at a proteolytic site to, an optionally heavy isotope labeled reporter peptide R; and a heavy labeled universal reporter peptide U analyzed by amino acid analysis. The heavy isotope labeled peptide need not undergo amino acid analysis. In one embodiment, several different proteotypic peptides from a single protein, linked to separate reporter peptides R, were analyzed. In one embodiment, several different proteotypic peptides concatenated into one polypeptide, linked to a single reporter peptide R, were analyzed.

BRIEF DESCRIPTION OF THE DRAWINGS

FIG. 8 shows a naming convention.

FIG. 17 provides data from a dilution curve mixture.

FIG. 18 provides information on isomers used to generate a single injection dilution curve.

FIG. 19 shows composition of an isotopologue mixture used to generate a single injection dilution curve.

FIG. 20 provides isomer internal standards for a single injection dilution curve.

FIG. 22 shows quantitation data using two different reporter peptides R and two heavy isotope labeled proteotypic peptides for one protein using the same reporter peptide R.

FIG. 24 lists selected sequences of heavy isotope labeled polypeptides and reporters R.

FIG. 26A shows calibration curve information.

FIG. 29 shows examples of limits of detection (LOD) and limits of quantitation (LOQ) for selected peptides.

FIG. 1 shows proteotypic peptides A, B, and C from protein or polypeptide P. A proteotypic peptide is a signature peptide that fragments into a defined or predictable ion series following MS dissociation to allow specific identification and quantitation of the parent protein, whether in a purified form or from a complex mixture. It has characteristics that render it readily quantified. A signature peptide is an unambiguous identifier of a specific protein. Any protein contains an average of between 10 and 100 signature peptides. Any signature peptide meets most of the following criteria: easily detected by mass spectroscopy, predictably and stably eluted from a liquid chromatography (LC) column, enriched by reversed phase high performance liquid chromatography (RP-HPLC), good ionization, good fragmentation. A peptide that is readily quantified meets most of the following criteria: readily synthesized, ability to be highly purified (>97%), soluble in ≤20% acetonitrile, low non-specific binding, oxidation resistant, post-synthesis modification resistant, and a hydrophobicity or hydrophobicity index ≥10 and ≤40. The hydrophobicity index is described in Krokhin, Molecular and Cellular Proteomics 3 (2004) 908, which is expressly incorporated herein by reference. A peptide having a hydrophobicity index less than 10 may not be reproducibly resolved by RP-HPLC. A peptide having a hydrophobicity index greater than 40 may not be reproducibly eluted from a RP-HPLC column.

Figure 6:
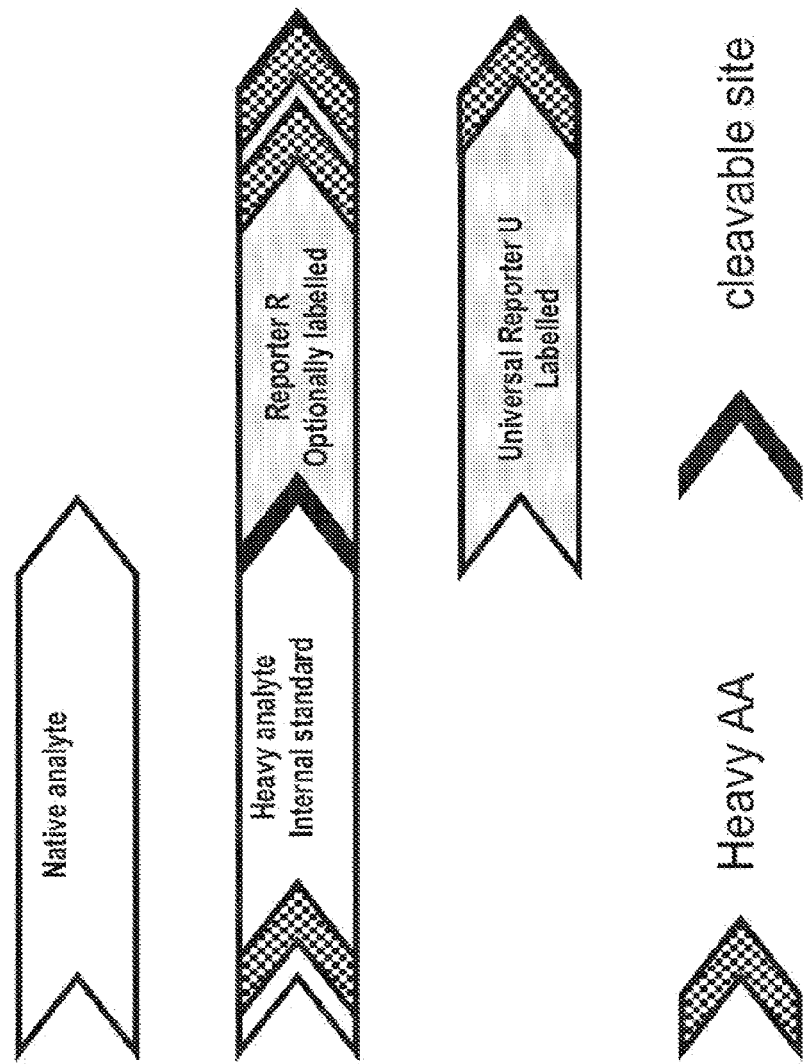
FIG. 6 shows configuration and relationship among components.
Figure 7:
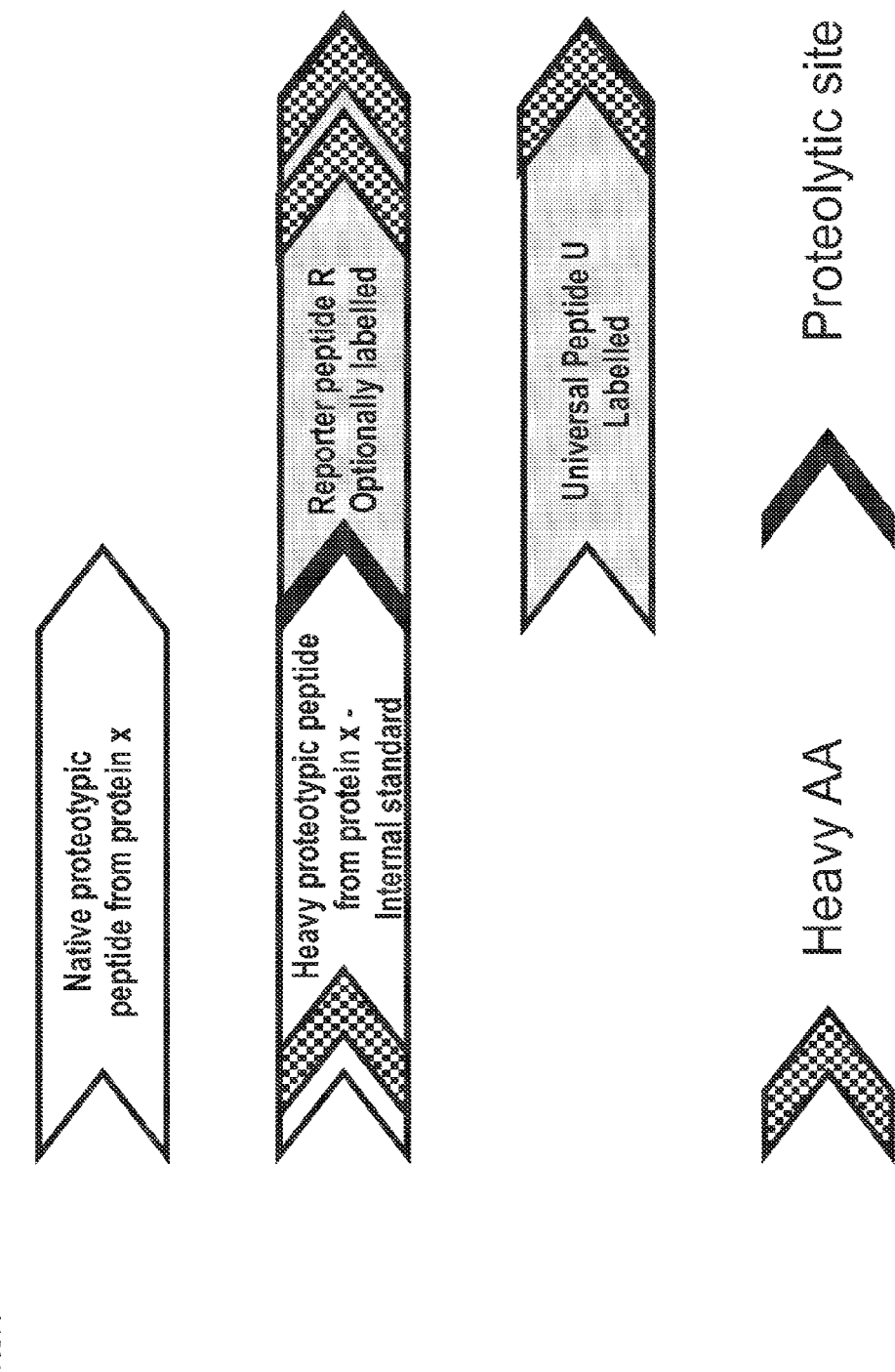
FIG. 7 shows configuration and relationship among peptide components.

The inventive method uses an internal standard that is the heavy stable isotope (labeled or modified) form of the analyte to be quantified, also referred to as a heavy analyte and shown in FIG. 6. In the embodiment using a proteotypic peptide, the internal standard is the labeled form of the proteotypic peptide, also referred to as a heavy proteotypic peptide, as shown in FIG. 7.

IDMS refers to the use of peptide modified with the heavy stable isotope (heavy isotope-labeled peptide) as internal standards to establish the concentration versus MS response relationship and to perform absolute quantitation of peptide. The heavy isotope labeled peptide has identical properties as the unlabeled peptide, except that its mass is shifted by the incorporated isotope(s). As a result of this mass shift, a known quantity of the isotope-labeled peptide can be used as an internal standard for peptide quantitation. The IDMS method results in targeted mass spectrometry (selected reaction monitoring (SRM)/multiple reaction monitoring (MRM)) quantitation of peptides in complex samples or mixtures. SRM encompasses the MS acquisition setup to quantify a list of target proteins by the quantitation of specific fragment ions from proteotypic peptides of these target proteins. Targeted assay development must be fast, have high throughput, be sensitive, specific, targeted, robust, reproducible, and cost effective; it typically uses liquid chromatography-tandem mass spectrometry (LC-MS/MS, LC/MS$^2$). However, precise quantitation of large number of peptides in targeted proteomics experiments using SRM remains challenging.

In IDMS, the native proteotypic peptide differs from the heavy proteotypic peptide only due to insertion of a heavy amino acid. A heavy amino acid contains $^{13}$C (a heavy isotope of carbon) and/or $^{15}$N (a heavy isotope of nitrogen). The insertion of a heavy amino acid results in HeavyPeptide AQUA®, which differs from the proteotypic peptide only by the difference in mass. The purity of the heavy peptide is increased to >97% using preparative high performance liquid chromatography (HPLC). The precise quantity of HeavyPeptide AQUA® is determined by amino acid analysis. The mixture of the peptide to be quantified and HeavyPeptide AQUA® as the internal standard yields two peaks in mass spectroscopy: the two peaks have the same elution time, but different masses. HeavyPeptide AQUA® is spiked into the sample to be analyzed at a know quantity, making it possible to use its quantity to calculate the quantity of the peptide to be analyzed from the peak surfaces. The method compares the surface of the corresponding MS peak from the heavy isotope labeled peptide, with the peak of the non-labeled peptide with the exact same sequence originating from the analyte (e.g., polymer, protein, peptide, or polypeptide) being quantified. The quantitation precision is directly correlated to the accuracy of the quantity of the heavy peptide added to the sample.

The following example, while used specifically with a protein analyte, illustrates the general method applicable for analytes, whether protein or non-protein. A sample (e.g., biological sample, food sample) containing numerous proteins is treated with a cleavage or digestion agent such as a protease (e.g., trypsin). Trypsin cleaves at each R amino acid and K amino acid, yielding numerous fragments, each fragment having about 13 amino acids (range 6 amino acids to 20 amino acids, up to 33 amino acids). Into this fragment-containing sample to be analyzed is introduced (spiked) one, two, or three HeavyPeptide AQUA® internal standards, and quantitation is performed as described. In embodiments using proteolytic digestion, the quantitation precision is also directly correlated to the digestion predictability and efficiency.

In one embodiment, proteins contain one, two, or three proteotypic peptide sequences, labeled as heavy or light (HeavyPeptide AQUA®, QuantPro®, or Ultimate®). The samples to be analyzed are spiked with the proteotypic peptides and quantitated by LC-MS/MS.

In IDMS, the internal standard has the same sequence as the proteotypic peptide from the protein to be quantified, but the internal standard has a different mass from the proteotypic peptide. The sequence of the internal standard is thus pre-determined by the protein sequence; it cannot be changed The internal standard must be quantified by amino acid analysis. Because the protein or polypeptide to be quantified differs with each experiment, the internal standard for this protein or polypeptide necessarily also differs with each experiment, and requires that amino acid analysis be performed with each experiment. Each quantitation requires a dilution curve that typically encompasses six points, each point requiring about one hour of MS time, prior to actual sample quantitation. The costs for amino acid analysis are relatively high and the procedure is time consuming. Each peptide sequence has specific solubility, and its non-specific binding constant varies based upon various factors that may differ with each analysis, e.g., vessel material, buffer, temperature, etc. Such variability decreases precision and reproducibility.

In contrast, with peptides as a non-limiting example, the inventive method using a modified, optimized, labeled universal reporter U, and one analyte, more than one analyte, or several concatenated analytes, increased the analytical precision of SRM where quality of internal standards is decisive to ensure precise quantification. Only this universal reporter U undergoes amino acid analysis, rather than an internal standard for each peptide to be quantified requiring amino acid analysis. Universal reporter U quantification thus need be performed only once, rather than with each experiment. The universal reporter U can be stocked and made readily available. In one embodiment, universal reporter U is labeled with a fluorophore, chemiluminescent molecule, and/or chromophore, and universal reporter U is quantified by measuring the absorbance of the fluorophore and/or chromophore and/or intensity of the chemiluminescent molecule. For peptide analytes, no amino acid analysis is required. In one embodiment, universal reporter peptide U contains one tryptophan, and universal reporter peptide U is quantified by measuring absorbance using the specific extinction factor of the tryptophan.

Figure 1:
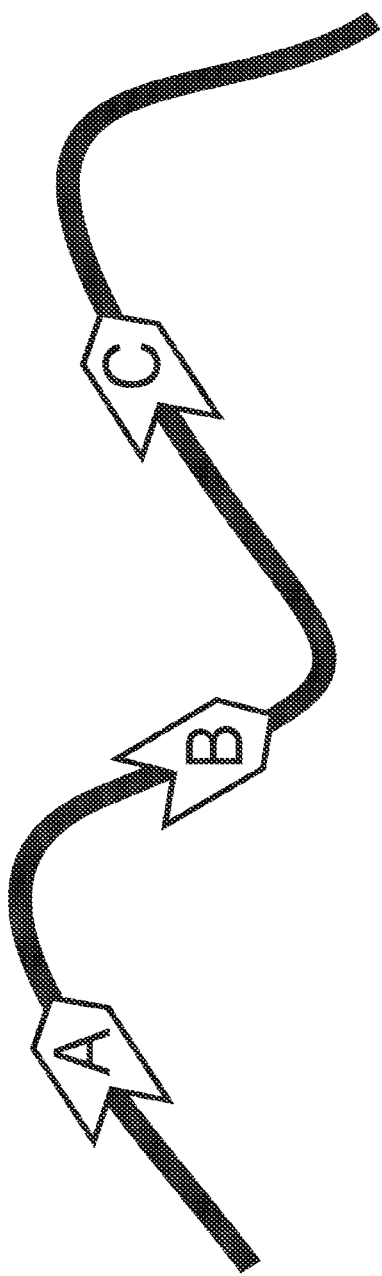
FIG. 1 shows peptides for mass spectrometry (MS) quantitation.
Figure 2:
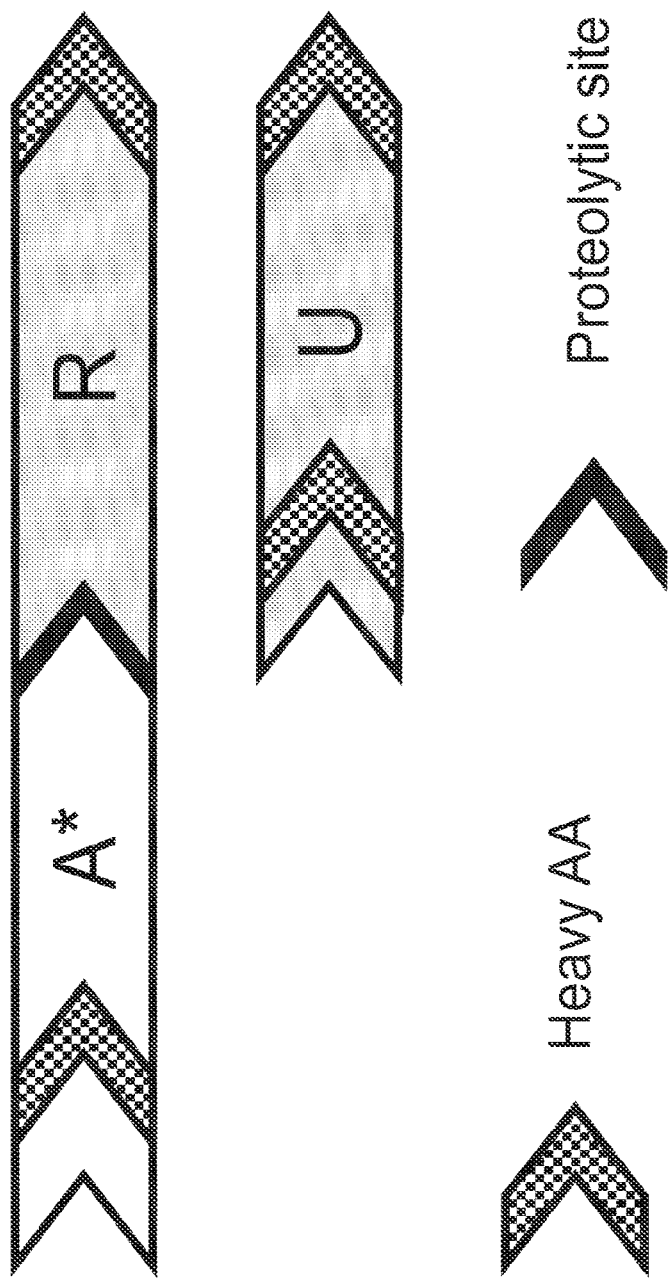
FIG. 2 shows a configuration for a peptide to be quantified linked to a reporter peptide and correlated to a universal peptide U.

As shown in FIG. 2 using a peptide analyte, in one embodiment peptide A*, the internal standard, is linked with a reporter peptide R through a cleavable site (e.g., proteolytic site) between A* and R. In this embodiment, each of peptide A* and reporter peptide R contain at least one amino acid labeled with a heavy isotope, known as a heavy amino acid. When reporter peptide R is labeled with a heavy isotope, and because universal reporter peptide U must have a different mass, universal reporter peptide U can be represented with two heavy amino acids, and reporter peptide R one heavy amino acid. However, there are other ways to obtain a difference in atomic mass; e.g., using different heavy amino acids for reporter peptide R and universal reporter peptide U to obtain a difference in atomic mass.

Peptide A* has the same sequence as proteotypic peptide A, but peptide A* has a different mass due to the presence of the heavy amino acid. Universal reporter peptide U is a peptide standard for reporter peptide R. Universal reporter peptide U is not the internal standard used to quantify the protein or polypeptide. Universal reporter peptide U has the exact same sequence as reporter peptide R but has a different atomic mass.

In the ligation between peptide A* and reporter peptide R, resulting in a polypeptide, the reporter peptide R can be C-terminal to A*, i.e., R-A*, or the reporter peptide R can be N-terminal to A*, i.e., A*-R. The nomenclature A*-R is used to represent either the A*-R polypeptide or the R-A* polypeptide. In either case when A* is a proteotypic peptide, there must be a cleavable (e.g., proteolytic) site between peptide A* and reporter peptide R in the resulting polypeptide.

The polypeptide A*-R is mixed with the sample that contains the protein or polypeptide P to be quantified. A known quantity of universal reporter peptide U is added to the sample, i.e., universal reporter peptide U is spiked into the sample. The sample is digested with a protease (e.g. trypsin) that cleaves the polypeptide bonds. As a result of protease action, polypeptide A*-R must be fully digested. In one embodiment, universal reporter peptide U is added before cleavage (e.g., proteolytic digestion). In one embodiment, universal reporter peptide U is added after cleavage (e.g., proteolytic digestion).

After digestion the concentration of peptide A* and reporter peptide R in the sample is equimolar. That is, the quantity of peptide A* is equal to the quantity of reporter peptide R. Universal reporter peptide U is used to quantify reporter peptide R using MS quantitation. The quantity of peptide A*, resulting from the proteolytic digestion of protein or polypeptide P, is used to measure the quantity of peptide A in the sample.

Figure 3:
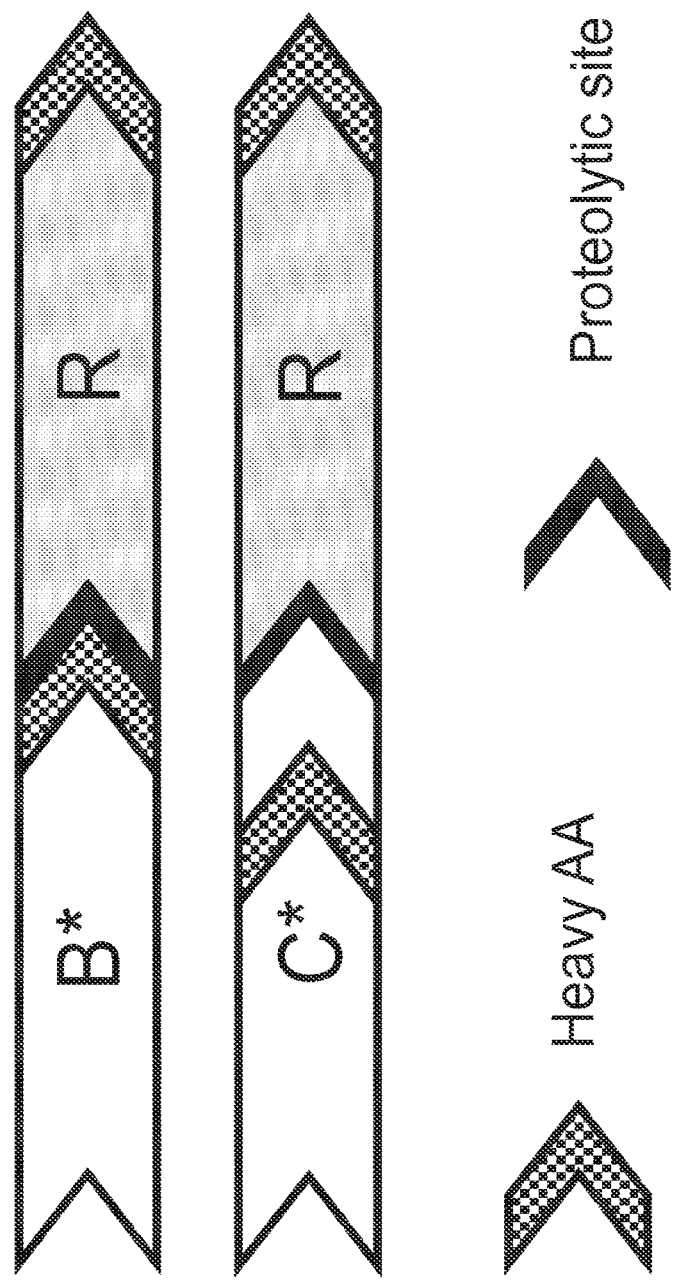
FIG. 3 shows an embodiment for quantitation of more than one peptide, each peptide linked to a separate reporter peptide R.

In the embodiment using a peptide shown in FIG. 3, the same method is applied to proteotypic peptides B and C from protein P in order to increase the specificity of the quantitation. Peptide B* has the same sequence as proteotypic peptide B but has a different atomic mass due to the presence of the heavy isotope labeled amino acid. Peptide C* has the same sequence as proteotypic peptide C but has a different atomic mass due to the presence of the heavy isotope labeled amino acid.

Using a peptide embodiment as an example, A*-R includes a cleavage or digestion site (e.g., proteolytic site) between A* and R. Polypeptide A*-R thus can be used as a pseudo-surrogate of protein or polypeptide P to monitor proteolytic digestion in a single experiment, digestion efficiency among samples and experiments, and in some cases to normalize results from different samples and/or different experiments.

Figure 5:
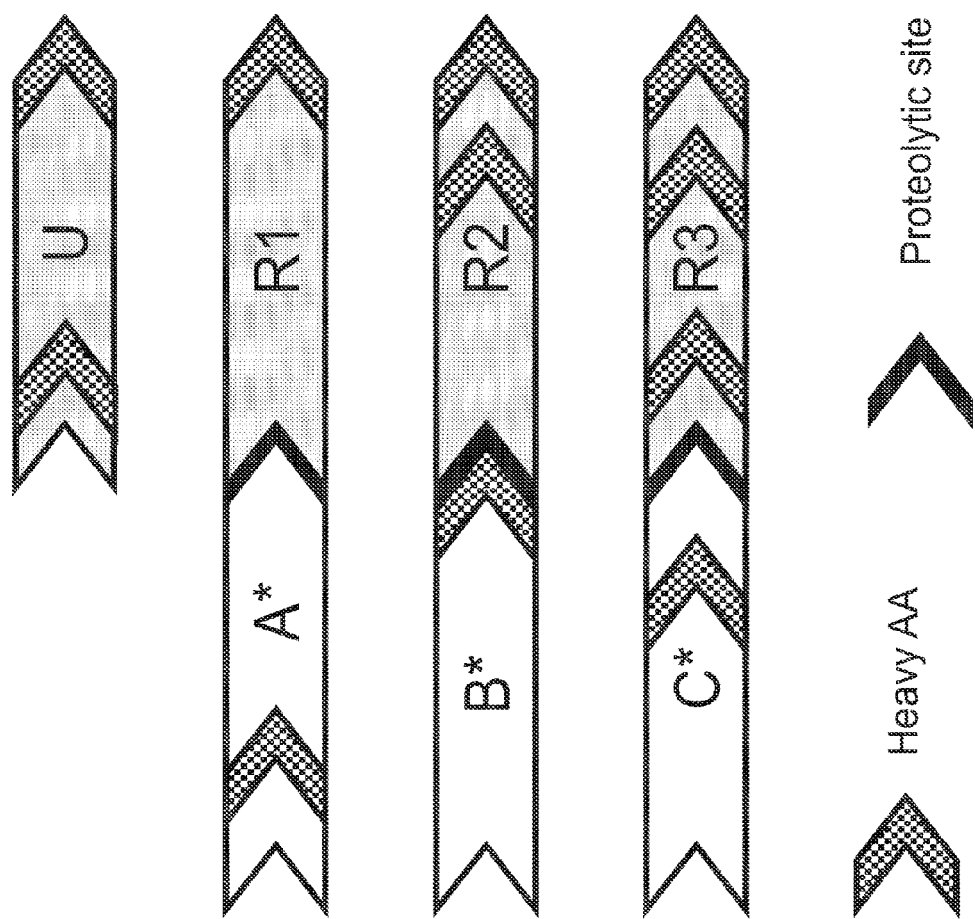
FIG. 5 shows an embodiment for simultaneous assay of more than one analyte in a sample using a single assay (multiplexing) where three proteotypic peptides, each cleavably linked to its own reporter peptide R and correlated to a single universal reporter peptide U.

In examples using peptides, reporter peptide R can be optimized for proteolytic digestion. As one example, reporter peptide R can be selected and/or modified so that it contains a specific amino acid (e.g., tryptophan) that is easily quantified by absorption measurements. As shown in FIG. 5, reporter peptide R may contain more than one heavy isotope labeled amino acid. This embodiment increases the multiplexing possibilities of the method by increasing the number of possible atomic masses for the same reporter peptide R sequence, so that multiple peptides can be quantified using universal reporter peptide U in a single experiment.

In this multiplexing embodiment, reporter peptide R is synthesized with different atomic masses, using standard methods known in the art. As shown in FIG. 5, peptides A, B, and C from protein or polypeptide P are quantified in a single experiment using heavy peptides A*, B*, and C*, respectively, and using reporter peptides R1, R2, R3. In the embodiment shown in FIG. 5, reporter peptides R1, R2, R3, and universal reporter peptide U, have the same sequence but different atomic masses. To maximize the number of mass combinations available for reporter peptide R, the sequence may be composed of, but is not limited to, one or more of the following amino acids: alanine, arginine, isoleucine, leucine, lysine, phenylalanine, valine. These amino acids have a mass shift or difference ≥4 Da. The minimum mass difference between the proteotypic peptide (e.g., A), and the internal standard (e.g., A*), should exceed the sensitivity threshold determination for MS differentiation. In one embodiment, the minimum mass difference between the proteotypic peptide and the internal standard is 4 kDa when 4 kDa is the minimum atomic mass difference that can be discriminated. The number of peptides that can be quantified simultaneously using a universal heavy peptide U is limited only by the number of mass difference combinations available within the sequence.

In another example using peptides, reporter peptide R may be designed with a low hydrophobicity index, which will increase the aqueous solubility of the polypeptide A*-R where peptide A* has a hydrophobicity index ≥40 or where peptide A* is poorly soluble. One example of a reporter peptide R having a sequence that renders it highly soluble is PVVVPR (SEQ ID NO. 1); it has a hydrophobicity index of 13.45. One example of a reporter peptide R having a sequence that renders it highly soluble is SSAAPPPPPR (SEQ ID NO. 2) with a Krokhin hydrophobicity factor of 7.57. In one example, each of reporter peptide R and universal reporter peptide U contains a chromophore and/or fluorophore used for quantification by absorbance measurement. In the embodiment where both universal reporter peptide U and reporter peptide R include a chromophore and/o fluorophore, universal reporter peptide U can be quantified by measuring the absorption of the chromophore and/or fluorophore, and not by amino acid analysis. The process of protein or polypeptide quantification by absorbance is more robust than the process of amino acid analysis. Protein or polypeptide quantification by absorbance is considered more precise than protein or polypeptide quantification by amino acid analysis. Examples of a chromophore or fluorophore and methods of assessing their absorbance are known in the art.

Figure 4:
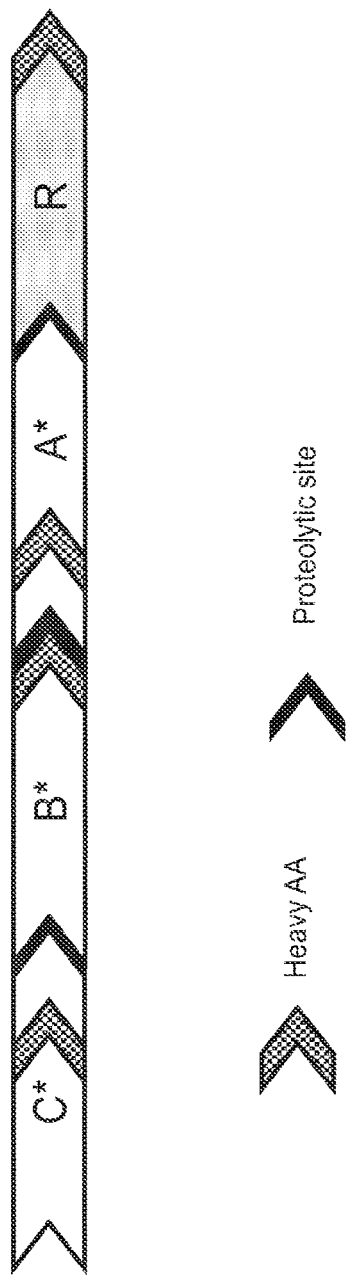
FIG. 4 shows an embodiment with three concatenated peptides linked to a single reporter peptide R.

In the embodiment shown in FIG. 4, the polypeptide contains three proteotypic peptides, each labeled with a heavy amino acid, concatenated with a single reporter peptide R also labeled with a heavy isotope amino acid, resulting in C*-B*-A*-R. Using this polypeptide C*-B*-A*-R guarantees equimolar quantities of each of peptides A*, B* and C* and thus decreases quantitation variability compared to quantitation using individual peptides. This embodiment increases the number of peptides that can be quantified with the same sequence as that of universal reporter peptide U.

In one embodiment, A*-R, or B*-A*-R, or C*-B*-A*-R can be cleaved before being introduced into the sample to be quantified.

In embodiments using proteotypic peptides, peptides A*, B*, C*, and reporter peptide R can be randomly arranged, as long as they are linked through a cleavage or digestion site (e.g., proteolytic site).

The polypeptide shown in FIG. 4 contains three heavy isotope labeled peptides (A*, B*, and C*), corresponding to target peptides A, B, and C, linked to reporter peptide R, also containing a heavy isotope label. Other embodiments are possible where R does not contain a heavy isotope label. Other embodiments are possible that contain various numbers (n) of labeled peptides corresponding to one or more target peptides, joined with one or more reporter peptides. The range for n is governed by, e.g., manufacturing feasibility, solubility, etc. as know to one skilled in the art. In one embodiment, a value of n up to 99 is possible. In one embodiment, a value of n up to 49 is possible. In one embodiment, n=4. In one embodiment, n=5. In one embodiment, n=6. In one embodiment, n=7. In one embodiment, n=8. In one embodiment, n=9. In one embodiment, n=10. In one embodiment, n=11. In one embodiment, n=12.

Universal reporter peptide U and reporter peptide R can be designed with different sequences for multiplex quantitation. The number of mass difference combinations determined by a peptide sequence is limited. When the number of peptides to be quantified exceeds the maximum number of mass difference combinations available for reporter peptide R, one can use additional sequences of universal reporter peptide U: e.g., $U^1$, $U^2$, ... $U^n$ where n is limited only by the number of peptides that can be simultaneously quantified by an instrument. As one example, the polypeptide A*-R may have the amino acid sequence TTVSKTETSQVAPA SEQ ID NO. 3, with peptide A* having the sequence TETSQVAPA SEQ ID NO. 4, and reporter peptide R having the sequence TTVSK SEQ ID NO. 5, as disclosed in WO/2003/046148.

Because the sequence of universal reporter peptide U is not restricted or limited, and because universal reporter peptide U is a product that can be readily ordered, stocked, maintained, and inventoried, its use provides flexibility to MS peptide quantitation. In one embodiment, the sequence of universal reporter peptide U can be customized to minimize non-specific binding of the peptide, polypeptide, or protein to, e.g., a vessel, tips, tubing, etc. by selecting a sequence with a low hydrophobicity index, e.g., PVVVPR SEQ ID NO. 1 which has a hydrophobicity index of 13.45 or SSAAPPPPPR (SEQ ID NO. 2), which has a hydrophobicity index of 7.57. In one embodiment, the sequence of universal reporter peptide U can be customized to maximize solubility of the polypeptide A*-R. For example, because universal reporter peptide U is used, the polypeptide A*-R need not be quantified precisely prior to MS analysis. This results in shorter manufacturing time and lower cost in producing polypeptide A*-R. Peptide A* is quantified at very low concentration, at which its solubility is guaranteed, resulting in enhanced precision and repeatability.

Because quantitation of peptide A* is performed on the same instrument used for the quantitation of reporter peptide R and within the same MS procedure, it always reflects the quantity added into the sample and is independent of eventual alteration, degradation, and partial loss of polypeptide A*-R during sample preparation, fractionation, and liquid chromatography separation prior to MS quantitation. When using the method described in WO 03/016861, A* is provided in a known concentration that is too high for use without dilution; thus, it is typically diluted 1000 to 10,000. If the sequence of A* is relatively hydrophobic and prone to non-specific binding, as is the case for β-amyloid peptides, a significant quantity of the standard will be lost during dilution. This decreases the method's precision. Because the sequence of universal reporter peptide U can be designed and optimized to decrease non-specific binding, the dilution of universal reporter peptide U is not prone to significant non-specific binding. Universal reporter peptide U is included in the sample to be quantified, and quantitation of reporter peptide R is performed in the diluted sample, thus non-specific binding of the standard (e.g., β-amyloid peptide) will not decrease the method's precision.

The polypeptide A*-R is a pseudo-surrogate of protein P and can be used to monitor cleavage (e.g., proteolytic digestion). It can be used to compare sample-to-sample, and/or experiment-to-experiment, digestion efficiency. It can be used to normalize results from sample-to-sample, and/or from experiment-to-experiment.

In one embodiment, the inventive method is adapted to MS quantitation of analytes, including but not limited to peptides, polypeptides, and proteins, using a proteotypic peptide that is coupled, through a cleavable site, to a reporter peptide R or other moiety. This is shown schematically in FIG. 6 for any analyte, and in FIG. 7 for a peptide analyte. The heavy proteotypic peptide contains the same amino acid sequence, but a different atomic mass, as the native proteotypic peptide. The heavy proteotypic peptide is in equimolar concentration with the reporter peptide R. In one embodiment, reporter peptide R is labeled with a heavy isotope. In one embodiment, reporter peptide R is not labeled with a heavy isotope. Universal reporter peptide U has the same sequence as reporter peptide R. Universal reporter peptide U has a different mass than reporter peptide R because it contains a heavy isotope label. Only universal reporter peptide U is quantified. After cleavage (e.g., proteolytic digestion), the heavy proteotypic peptide and the reporter peptide R are released at equimolar concentration into the sample. The quantity of the reporter peptide R is determined using the quantity of heavy universal reporter peptide U.

Universal reporter peptide U is sequence independent and is used as a quantitation standard and a cleavage or digestion standard. Universal reporter peptide U has a peptide sequence that is identical to reporter peptide R but is independent from the protein to be assayed. Because the sequence of universal reporter peptide U and reporter peptide R is identical, the atomic mass difference between universal reporter peptide U and reporter peptide R is obtained using a heavy labeled reporter peptide R and a heavy labeled universal reporter peptide U. The atomic mass difference is obtained by using different heavy labels in reporter peptide R and universal reporter peptide U, or by using an additional heavy amino acid in reporter peptide R or universal reporter peptide U. Reporter peptide R may have a lower atomic mass or a higher atomic mass than universal reporter peptide U.

As represented in FIG. 8, a convenient convention for naming components is as follows: proteotypic peptides are named as letters, e.g., A, B, C; heavy isotope labeled proteotypic peptides are named as letters with an asterisk indicating a heavy isotope label, e.g., A*, B*, C*; R is a reporter; U is a universal reporter; amino acid bearing the heavy isotope label indicated by either conventional amino acid one- or three-letter naming in bold font, e.g., either R or Arg indicates the amino acid arginine with a heavy isotope label; one composition of concatenated peptides and universal reporter, commercially available under the trademark HeavyPeptide IGNIS™, is A*B*C*R.

In one embodiment, the sequence of universal reporter peptide U is optimized and/or customized to be compatible with the properties of the proteotypic peptide by optimizing chromatographic ionization and fragmentation properties. As one example, universal reporter peptide U is modified to enhance ionization and/or desolvation by introducing additional charge or hydrophobic properties. As one example, universal reporter peptide U is modified to enhance fragmentation by introducing an aspartate-proline (DP) group that contains a highly scissile bond that fragments in tandem MS at lower collisions energies than other dipeptide linkages. As one example, universal reporter peptide U is modified to have a similar retention time on liquid chromatography as the proteotypic peptide by choosing a reporter peptide with a similar hydrophobicity factor to the proteotypic peptide. Thus, universal reporter peptide U can be optimized by design. For example, the number of mass combinations for the identical peptide sequence can be optimized to increase the multiplexing capacity, yielding up to 100 proteins capable of being quantified in a single assay. Yet because the peptide sequences are identical, only one dilution curve is required to quantify universal reporter peptide U. By increasing the number of identical sequences with different masses, the number of proteins that can be quantified in a single experiment increases, without concomitant increase in instrumentation use and resources.

In one embodiment, the universal reporter peptide U was optimized for low specific binding, high solubility, high MS signal intensity, and/or desired liquid chromatography retention time. In one embodiment, its peptide sequence was modified to change its chromatographic retention properties; this is one example of internal modification. In one embodiment, its structure was modified by attaching tags to change its chromatographic retention properties; this is one example of external modification. In one embodiment, its structure was modified by attaching tags that themselves had been modified to change its chromatographic retention properties; this is another example of external modification.

In one embodiment, a universal polymer is used, where polymer is broadly defined as a joined group of monomers. The monomers either need not be peptides, or need not be entirely peptides. In one embodiment, polysaccharides (i.e., glycan monomers) are used as universal polymers ($U^{polymer}$). A polysaccharide is a combination of two or more monosaccharides linked by glycosidic bonds. Examples of polysaccharides include starch, cellulose, and glycogen. Their structures and synthesis are know in the art. In one embodiment, deoxyribonucleic acid (DNA) or ribonucleic acid (RNA) are used as universal polymers ($U^{polymer}$). Their structures and synthesis are known in the art. Methods to detect and quantify nucleotides are well established, e.g., PCR, quantitative PCR. Nucleotides attached to an analyte can by used as a unique identifier (i.e., "barcode") of the analyte and for quantitation purposes using PCR, quantitative PCR, or isotopic dilution.

In one example, one of the following peptide sequences shown in the table below, currently used as retention time calibrator peptides, was used as universal reporter peptide U. These peptides exhibited sufficient ionization and had defined elution properties. The following table below shows their sequence, hydrophobicity, and chromatograph behavior on a Hypersil Gold $C_{18}$ column.

| Peptide | SEQ ID No. | Hydrophobicity Factor | Retention Time (min) |
|---|---|---|---|
| SSAAPPPPPR | 2 | 7.57 | 4.77 |
| GISNEGQNASIK | 6 | 15.50 | 6.62 |
| HVLTSIGEK | 7 | 15.52 | 7.22 |
| DIPVPKPK | 8 | 17.65 | 7.67 |
| IGDYAGIK | 9 | 19.15 | 8.18 |
| TASEFDSAIAQDK | 10 | 25.88 | 9.01 |
| SAAGAFGPELSR | 11 | 25.24 | 9.41 |
| ELGQSGVDTYLQTK | 12 | 28.37 | 9.63 |
| SFANQPLEVVYSK | 13 | 34.96 | 10.67 |
| GLILVGGYGTR | 14 | 32.18 | 10.79 |
| GILFVGSGVSGGEEGAR | 15 | 34.52 | 10.86 |
| LTILEELR | 16 | 37.30 | 11.87 |
| NGFILDGFPR | 17 | 40.42 | 12.16 |
| ELASGLSFPVGFK | 18 | 41.19 | 12.21 |
| LSSEAPALFQFDLK | 19 | 46.66 | 12.85 |

Hydrophobicity was determined using calculations done with algorithms described in Spicer. et al (2007). Sequence-specific retention calculator. A family of peptide retention time prediction algorithms in reversed-phase HPLC: applicability to various chromatographic conditions and columns. Anal Chem. 79(22):8762-8.

In one embodiment, the heavy isotope label is incorporated in the C-terminal amino acid. For example, using the peptide SSAAPPPPPR SEQ ID NO. 2, this embodiment can be represented as SSAAPPPPPR*, where the terminal R contains the heavy isotope label.

In one embodiment, the heavy isotope is incorporated in the peptide at a position other than the C-terminus. One or more of the following amino acids may be labeled with a heavy isotope: alanine, arginine, isoleucine, leucine, lysine, phenylalanine, valine. These amino acids have a mass shift or difference >4 Da. Additionally, multiple amino acids within the peptide can be labeled, and the same amino acid may be labeled with different isotopes, such as $^{13}C_6$-arginine (R) and $^{13}C_6^{15}N_4$-arginine which would introduce a 6 Da and 10 Da mass shift, respectively. For example, using the peptide SSAAPPPPPR SEQ ID NO. 2 where * indicates the amino acid containing the position of the heavy isotope label, the following positions are possible: S*SAAPPPPPR, SS*AAPPPPPR, SSA*APPPPPR, SSAA*PPPPPR, SSAAP*PPPPR, SSAAPP*PPPR, SSAAPPP*PPR, SSAAPPPP*PR, SSAAPPPPP*R, SSAAPPPPPR*, S*SAAPPPPPR*, SS*AAPPPPPR*, SSA*APPPPPR*, SSAA*PPPPPR*, SSAAP*PPPPR*, SSAAPP*PPPR*, SSAAPPP*PPR*, SSAAPPPP*PR*, SSAAPPPPP*R*, SSAAPPPPPR (with respect to SSAAPPPPPR, double labeling permits higher multiplexing; the quantitation is performed at the MS/MS level using fragments from the parent ion). This embodiment, where the heavy peptide is located at a position other than the C-terminus, permits higher multiplexing with the same reporter sequence.

For multiplexed assays, custom peptides are combined together into complex targeted assays. Each custom peptide has a different corresponding universal reporter U that elutes similarly to the custom peptide. This permits many peptides to be easily multiplexed and quantified across an LC gradient without cross contamination. For example, a multiplex analysis array contains any number of different universal peptides U having the same amino acid sequence, but a different atomic mass due to the presence of a heavy isotope, and a number of reporter peptides R, each reporter peptide R cleavably linked to a different isotopically labeled proteotypic peptide to be quantified in a sample. The universal peptides U have substantially similar chromatography retention time as the custom peptide. In one embodiment, the heavy isotope label in the universal reporter peptide U is moved to different amino acids. This embodiment permits higher multiplex arrays using the same universal reporter peptide U amino acid sequence.

In one embodiment, the universal reporter peptide U is customized for a specific mass spectrometer and/or specific use for identification, characterization, and quantitation of disease biomarkers (proteomics, metabolomics, pharmacoproteomics) discovery, confirmation, validation, and early clinical diagnosis and disease progression monitoring. For example, a 4-10 amino acid reporter peptide will fragment into fewer product ions in a mass spectrometer, yielding greater fragment ion intensities overall than an 11-25 amino acid reporter peptide. The more intense product ions would give better sensitivity for a triple quadrupole mass spectrometer. Alternatively, a larger 11-25 amino acid peptide could ionize at a higher charge state and be seen and measured more readily with a high mass accuracy mass spectrometer. Proteomics has advanced from identification (qualitative proteomics) to quantitation by incorporating an internal standard in the assay. An internal standard is required because the resulting peak height or peak surface in mass spectroscopy results from a complex function of parameters (e.g., peptide quantity, peptide ionization, peptide fragmentation, ion suppression, etc.). There is no algorithm able to evaluate the response factor, which is the correlation between the peak surface and quantity of peptide, and therefore to measure the quantity of a peptide from the surface of the mass spectroscopy peak. When a known quantity of the internal standard is added to the peptide to be analyzed, the quantity of the peptide is determined by comparing its peak surface with the internal standard peak surface.

One embodiment is a described peptide modified with a tag. Such a tag, used to modify the peptide, differs from the heavy isotope label that is required or is optional to modify universal reporter U and reporter R, respectively. The tag, however, may be a heavy isotope, as subsequently described in the first example.

One example of such a tag is a heavy isotope. One example of such a tag is an isotopic tag. Such tags include forms of the same chemical structure with each tag having an incrementally heavier mass by 5 Da. Upon peptide fragmentation, the tag breaks to release a different specific reporter peptide that has a different weight.

One example of such a tag is a different isotope of the same peptide. This example uses as a tag an element that naturally has multiple isotopes, and where the isotopes have a different mass. For example, chlorine may be used because chlorine has two natural isotopes that differ by 2 Da.

One example of such a tag is a mass defect tag. This example uses as a tag an element that has a known mass defect such as bromine or fluorine. Use of a mass defect tag shifts the reporter peptide to a region of the mass chromatogram in which most isotopes are not observed, sometimes referred to as a mass quiet space. This example is useful to enhance sensitivity and specificity of detection in a mass region with many other background ions.

One example of such a tag is a retention time tag. Use of a retention time tag shifts the reporter peptide to a region of the mass chromatogram in which most peptides are not observed, sometimes referred to as a chromatographic quiet space. This example is useful to enhance gradient efficiency and utility for enhanced separation. As one example, a sample with early elution from a chromatography column upon application of a solvent or solvent gradient consumes less time and resources, which enhances efficiency. In use, this embodiment permits one to determine both the custom peptide and the universal reporter peptide U by using focused chromatographic conditions in short liquid chromatography analyses, i.e., runtimes less than one minute. As one example, a sample with late elution from a chromatography column upon application of a solvent or solvent gradient would be expected to have reduced cross contamination because there would be fewer eluting peptides in this region of the gradient. In all cases, instrument duty cycle is not wasted, and sensitivity and quantitative accuracy are not affected during critical gradient times. Use of such a focused system requires verification with a universal reporter peptide U that is demonstrated to efficiently and predictably elute under these conditions.

As one example of customization, the universal reporter peptide U is customized for use in stable isotope labeling with amino acids in cell culture (SILAC). Stable isotope-labeled amino acids are fed to live cells and the labeled amino acids are incorporated into polypeptides. The universal peptide is designed to quantify peptides from structural proteins, chaperones, or housekeeping enzymes to quantify and normalize protein quantities between samples. SILAC and its variations, known to one skilled in the art, uses mass spectrometry to quantitate and compare proteins among samples, and sample normalization and measurement of biological variation with structural proteins, chaperones, or housekeeping enzymes allows large numbers of samples to be processed and compared. In one embodiment, the universal reporter peptide U is customized for use with isobaric labeling using either tandem mass tags (TMT) or isobaric tags for relative and absolute quantitation (iTRAQ) by labeling a set of universal reports for quantitation of peptides from commonly observed proteins in cell and tissue lysates, serum and plasma, and formalin-fixed paraffin embedded tissue slices. TMT and iTRAQ have the general structure M-F-N-R where M=mass reporter region, F=cleavable linker region, N=mass normalization region, and R=protein reactive group. Isotopes substituted at various positions in M and N cause each tag to have a different molecular mass in the M region with a corresponding mass change in the N region, so that the set of tags have the same overall molecular weight. Only when the TMT undergo a second or third fragmentation (such as in tandem mass spectrometry MS/MS, or sequential mass spectrometry MS/MS/MS, $MS^3$) are they distinguishable, with backbone fragmentation yielding sequence and tag fragmentation yielding mass reporter ions needed to quantitate the peptides. iTRAQ and TMT covalently label amine groups in protein digests and a cysteine reactive TMT labels thiols of cysteines, resulting in individual digests with unique mass tags. The labeled digests are then pooled and fragmented into peptide backbone and reporter ions. The peptide backbone ions are used to identify the protein from which they came. The reporter ions are used to quantify this protein in each of the combined samples. SILAC, TMT, and iTRAQ mass spectroscopy methods used in biomarker discovery to generate candidate markers are used on instrumentation that include LTQ Velos (Thermo Scientific) and LTQ Orbitrap Velos (Thermo Scientific) hybrid mass spectrometer. The candidate markers are then further evaluated and applied in target analysis using selected reaction monitoring (SRM) to target quantitation of peptide markers in many samples. For confirmation and validation, the universal reporter peptide U is customized for use, as explained below, with the markers that were previously identified, for absolute quantitation with synthetic stable-isotope-labeled peptide standards (HeavyPeptide AQUA and its variations, Thermo Scientific) using existing discovery data to automate the preliminary selection for targeted analysis (Pinpoint software, Thermo Scientific; TSQ Vantage triple stage quadrupole mass spectrometer (Thermo Scientific)). The data are entered into a integrated data management system for clinical applications.

One embodiment is a universal reporter peptide U synthesized to provide it with similar (e.g., ±10% to 20%) properties (e.g., retention time, ionization, optimal fragmentation energy, limit of detection, digestion efficiency, etc.) to a custom peptide. In a method using this embodiment, the universal reporter peptide U is used to assess digestion efficiency. In use, this embodiment permits one to assess the proteotypic peptide and both the undigested and digested custom peptide and the universal reporter peptide U. The efficiency of digestion of the custom and universal peptide to the individual peptides is then used to correct the level of proteotypic peptide quantified, allowing more accurate absolute quantitation of the protein of interest and more accurate quantification between samples by correcting for digest efficiency between samples.

One embodiment is a set of universal peptides U. This set of universal peptides U co-elutes in a predictable manner. The peptides in the set may or may not share a common sequence. The peptides in the set have stable isotopes incorporated at unique positions to enable specific quantitation of each.

One embodiment is universal reporter U that is not limited to a peptide or that does not include a peptide component at all. This embodiment uses a universal polymer $U^{polymer}$. One example of such a non-peptide-limiting universal reporter U is sequence of natural and non-natural amino acids. One example of such a non-peptide-limiting universal reporter U is a deoxyribonucleic acid (DNA) sequence. One example of such a non-peptide-limiting universal reporter U is a locked nucleic acid (LNA) sequence. One example of such a non-peptide-limiting universal reporter U is a peptide nucleic acid (PNA). One example of such a non-peptide-limiting universal reporter U is a threose nucleic acid (TNA). As known to one skilled in the art, a PNA is an artificially synthesized polymer. Its structure is similar to the structure of deoxyribonucleic acid (DNA) and ribonucleic acid (RNA) but, unlike DNA having a deoxyribose triphosphate structure from which bases are attached, or RNA having a ribose triphosphate structure from which bases are attached, PNA has a repeating N-(2-aminoethyl) structure linked by peptide bonds from which bases are attached by methylene carbonyl bonds. As known to one skilled in the art, a TNA has a repeating threose structure linked by phosphodiester bonds. As known to one skilled in the art, a LNA is a modified ribonucleic acid (RNA) in which ribose contains an additional bond between its 2' oxygen and its 4' carbon, enhancing base stacking and affecting nucleic acid hybridization by increasing melting temperature $T_m$).

This embodiment adds to a sample an isotopically labeled proteotypic analyte coupled to a reporter analyte R through a cleavable site. Cleavage or digestion at the cleavable site decouples the reporter analyte R from the proteotypic analyte resulting in equimolar concentrations of each of the proteotypic analyte and the reporter analyte R in the sample. Mass spectroscopy analysis is performed without amino acid analysis to determine a concentration of the reporter analyte R using a quantity of a universal polymer $U^{polymer}$ added to the sample. The universal polymer $U^{polymer}$ has the same amino acid or monomer sequence, but a different atomic mass, as reporter analyte R due to the presence of a stable isotope label in universal polymer $U^{polymer}$.

One embodiment is a universal peptide compound, composition, formulation, and/or kit.

Figure 15:
FIG. 15 schematically shows a reporter sequence R positioned in the N-terminal.

In one embodiment, a kit contains a composition of concatenated peptides and a universal reporter sequence LVALVR (SEQ ID NO. 48) having a purity of about 80%, that is, a relatively low purity. While the analytical HPLC is relatively low, the fact that the universal reporter sequence is positioned in the N-terminal region, as shown in FIG. 15, is favorable to a stoichiometry closer to 1:1, which provided a precise method. This was due to synthesis from C— to N— and a capping agent used during synthesis. In this embodiment, the kit contained the following components:

5 aliquots of 0.5 nmol HeavyPeptide IGNIS CCC™ (Thermo Fisher Scientific) (polypeptide of N-terminal reporter peptide R and C-terminal heavy isotope labeled proteotypic peptide (A*);

5 aliquots of dilution curve isotopologues mixture, composition shown in FIG. 19;

5 aliquots of universal reporter R bracketing mixture, composition shown in FIG. 20.

Mixtures, as known to the skilled person, are the product of a mechanical blending or mixing of chemical substances (e.g., elements, compounds) without chemical bonding or other chemical change, so that each component retains its own chemical properties and composition.

As shown in FIG. 15, HeavyPeptide IGNIS™ AAA analytical HPLC purity >80% with an N-terminal reporter R position was more favorable to a 1:1 stoichiometry between the reporter R and the proteotypic sequence. Its standard length was ≤26 amino acids, including the 6 amino acids from reporter R. Optionally, additional light amino acids and modifications (S-carboxymethylation of cysteine (CAM), phosphorylation of serine, threonine, and/or tyrosine, etc.) can be added, as known to one skilled in the art.

In one embodiment, the heavy proteotypic peptide-reporter peptide R can be formulated dry. In one embodiment, the heavy proteotypic peptide-reporter peptide R can be formulated in solution. The heavy proteotypic peptide-reporter peptide R is stabilized and solubilization is facilitated by formulating it in a matrix with a non-reducing sugar (e.g., monosaccharides, oligosaccharides, polysaccharides and derivatives, sorbitol, mannitol, trehalose, etc.), or any matrix that facilitates reconstitution of the peptide while stabilizing the peptide at ambient temperature (e.g., about 19° C. to about 22° C.) using methods known to one skilled in the art. In this form, it is stable at atomole or femtomole quantities. In one embodiment, the heavy proteotypic peptide-reporter peptide R is formulated as a tablet that could be transported and stored at ambient temperatures and would be easily transferred to vials with the need for liquid measurement. This format eliminates concerns about peptide binding non-specifically to a tube wall or solvent evaporation resulting in changes in peptide concentration. This embodiment reduces the number of manipulations required and, hence, decreases error. This embodiment facilitates automation.

In one embodiment, the heavy proteotypic peptide-reporter peptide R is used in food control applications. Universal peptides are used to detect proteins from food allergens, such as almond, egg, gliadin/gluten, hazelnut, lupine, casein, β-lactoglobulin (BLG), total milk, mustard, peanut, sesame, shellfish, soy, and walnut residues, and/or contaminants such as *Salmonella, E. coli*, viruses, protozoan parasites, prions, and other zoonotic diseases, mycotoxins, and aflatoxins. Universal peptides are used in MS-based tests to detect the target allergen or toxin in ingredients, liquids, clean-in-place rinses, finished foods, and/or on environmental surfaces.

In one embodiment, the heavy proteotypic peptide-reporter peptide R is used in biobanking. Investigators realize that proper biosample collection, processing, storage, and tracking is critical for biomarker related studies. Investigators are concerned that information stored in biobanks will be inaccurate and incomplete, and thus of questionable usefulness to research, leading to spurious links between proteins, genes, and metabolite biomarkers. The addition of a quality control step will quality the condition of any sample used prior to studies on that sample. Quality control is based on incorporating precise and known quantities of isotopic peptide standards to a biological sample prior to final storage. These peptides have different proteolytic degradation kinetics, are labeled with stable heavy isotopes, and are quantifiable with existing MS technology. Upon request for a biobanked sample, the quantity of each peptide standard is measured by MS and used to evaluate the sample quality. Formulation of the heavy peptide-reporter peptide R is stabilized. Solubilization is facilitated by formulating it with a non-reducing sugar (e.g., sorbitol, mannitol, etc.) using methods known to one skilled in the art. In this form, the quality control sample is stable at attomole or femtomole quantities.

As one example, when the protein or polypeptide to be quantified is represented as A, the internal standard is represented as A*, with * denoting the labeled form; when the protein or polypeptide to be quantified is represented as B, the internal standard is represented as B*, etc. In one embodiment, the internal standard can be a non-proteotypic peptide, e.g., a β-amyloid peptide can be used as an internal standard to quantify β-amyloid peptide in a biological sample. For example, the following β-amyloid peptides and peptide fragments may be used; the bolded amino acids indicate mutations in the β-amyloid peptide sequence:

```
SEQ ID NO. 20 (1-40) peptide:
Asp-Ala-Glu-Phe-Arg-His-Asp-Ser-Gly-Tyr-Glu-Val- His-His-Gln-Lys-Leu-Val-Phe-Phe-Ala-Glu-Asp-Val- Gly-Ser-Asn-Lys-Gly-Ala-Ile-Ile-Gly-Leu-Met-Val- Gly-Gly-Val-Val SEQ ID NO. 21 (1-42) peptide:
Asp-Ala-Glu-Phe-Arg-His-Asp-Ser-Gly-Tyr-Glu-Val- His-His-Gln-Lys-Leu-Val-Phe-Phe-Ala-Glu-Asp-Val- Gly-Ser-Asn-Lys-Gly-Ala-Ile-Ile-Gly-Leu-Met-Val- Gly-Gly-Val-Val-Ile-Ala SEQ ID NO. 22 (1-43) peptide:
Asp-Ala-Glu-Phe-Arg-His-Asp-Ser-Gly-Tyr-Glu-Val- His-His-Gln-Lys-Leu-Val-Phe-Phe-Ala-Glu-Asp-Val- Gly-Ser-Asn-Lys-Gly-Ala-Ile-Ile-Gly-Leu-Met-Val- Gly-Gly-Val-Val-Ile-Ala-Thr SEQ ID NO. 23 (1-46) peptide:
Asp-Ala-Glu-Phe-Arg-His-Asp-Ser-Gly-Tyr-Glu-Val- His-His-Gln-Lys-Leu-Val-Phe-Phe-Ala-Glu-Asp-Val- Gly-Ser-Asn-Lys-Gly-Ala-Ile-Ile-Gly-Leu-Met-Val- Gly-Gly-Val-Val-Ile-Ala-Thr-Val-Ile-Val SEQ ID NO. 24 (1-40 F4W) peptide:
Asp-Ala-Glu-Trp-Arg-His-Asp-Ser-Gly-Tyr-Glu-Val- His-His-Gln-Lys-Leu-Val-Phe-Phe-Ala-Glu-Asp-Val- Gly-Ser-Asn-Lys-Gly-Ala-Ile-Ile-Gly-Leu-Met-Val- Gly-Gly-Val-Val SEQ ID NO. 25 (1-40 Y10W) peptide:
Asp-Ala-Glu-Phe-Arg-His-Asp-Ser-Gly-Trp-Glu-Val- His-His-Gln-Lys-Leu-Val-Phe-Phe-Ala-Glu-Asp-Val- Gly-Ser-Asn-Lys-Gly-Ala-Ile-Ile-Gly-Leu-Met-Val- Gly-Gly-Val-Val SEQ ID NO. 26 (1-40 D23N) peptide:
Asp-Ala-Glu-Phe-Arg-His-Asp-Ser-Gly-Tyr-Glu-Val- His-His-Gln-Lys-Leu-Val-Phe-Phe-Ala-Glu-Asn-Val- Gly-Ser-Asn-Lys-Gly-Ala-Ile-Ile-Gly-Leu-Met-Val- Gly-Gly-Val-Val SEQ ID NO. 27 (1-42 M35V) peptide:
Asp-Ala-Glu-Phe-Arg-His-Asp-Ser-Gly-Tyr-Glu-Val- His-His-Gln-Lys-Leu-Val-Phe-Phe-Ala-Glu-Asp-Val- Gly-Ser-Asn-Lys-Gly-Ala-Ile-Ile-Gly-Leu-Val-Val- Gly-Gly-Val-Val-Ile-Ala SEQ ID NO. 28 (1-42 R5G) peptide:
Asp-Ala-Glu-Phe-Gly-His-Asp-Ser-Gly-Tyr-Glu-Val- His-His-Gln-Lys-Leu-Val-Phe-Phe-Ala-Glu-Asp-Val- Gly-Ser-Asn-Lys-Gly-Ala-Ile-Ile-Gly-Leu-Met-Val- Gly-Gly-Val-Val-Ile-Ala SEQ ID NO. 29 (1-42 Y10A) peptide:
Asp-Ala-Glu-Phe-Arg-His-Asp-Ser-Gly-Ala-Glu-Val- His-His-Gln-Lys-Leu-Val-Phe-Phe-Ala-Glu-Asp-Val- Gly-Ser-Asn-Lys-Gly-Ala-Ile-Ile-Gly-Leu-Met-Val- Gly-Gly-Val-Val-Ile-Ala SEQ ID NO. 30 (1-42 F4W) peptide:
Asp-Ala-Glu-Trp-Arg-His-Asp-Ser-Gly-Tyr-Glu-Val- His-His-Gln-Lys-Leu-Val-Phe-Phe-Ala-Glu-Asp-Val- Gly-Ser-Asn-Lys-Gly-Ala-Ile-Ile-Gly-Leu-Met-Val- Gly-Gly-Val-Val-Ile-Ala SEQ ID NO. 31 (1-42 H6A) peptide:
Asp-Ala-Glu-Phe-Arg-Ala-Asp-Ser-Gly-Tyr-Glu-Val- His-His-Gln-Lys-Leu-Val-Phe-Phe-Ala-Glu-Asp-Val-
```

-continued

Gly-Ser-Asn-Lys-Gly-Ala-Ile-Ile-Gly-Leu-Met-Val-

Gly-Gly-Val-Val-Ile-Ala

SEQ ID NO. 32 (1-42 H13A) peptide:
Asp-Ala-Glu-Phe-Arg-His-Asp-Ser-Gly-Tyr-Glu-Val-

Ala-His-Gln-Lys-Leu-Val-Phe-Phe-Ala-Glu-Asp-Val-

Gly-Ser-Asn-Lys-Gly-Ala-Ile-Ile-Gly-Leu-Met-Val-

Gly-Gly-Val-Val-Ile-Ala

SEQ ID NO. 33 (1-42 H14A) peptide:
Asp-Ala-Glu-Phe-Arg-His-Asp-Ser-Gly-Tyr-Glu-Val- His-Ala-Gln-Lys-Leu-Val-Phe-Phe-Ala-Glu-Asp-Val- Gly-Ser-Asn-Lys-Gly-Ala-Ile-Ile-Gly-Leu-Met-Val- Gly-Gly-Val-Val-Ile-Ala SEQ ID NO. 34 (1-11) peptide fragment:
Asp-Ala-Glu-Phe-Arg-His-Asp-Ser-Gly-Tyr-Glu SEQ ID NO. 35 (1-16) peptide fragment:
Asp-Ala-Glu-Phe-Arg-His-Asp-Ser-Gly-Tyr-Glu-Val- His-His-Gln-Lys SEQ ID NO. 36 (1-28) peptide fragment:
Asp-Ala-Glu-Phe-Arg-His-Asp-Ser-Gly-Tyr-Glu-Val- His-His-Gln-Lys-Leu-Val-Phe-Phe-Ala-Glu-Asp-Val- Gly-Ser-Asn-Lys SEQ ID NO. 37 (1-38) peptide fragment:
Asp-Ala-Glu-Phe-Arg-His-Asp-Ser-Gly-Tyr-Glu-Val- His-His-Gln-Lys-Leu-Val-Phe-Phe-Ala-Glu-Asp-Val- Gly-Ser-Asn-Lys-Gly-Ala-Ile-Ile-Gly-Leu-Met-Val- Gly-Gly SEQ ID NO. 38 (11-22) peptide fragment:
Glu-Val-His-His-Gln-Lys-Leu-Val-Phe-Phe-Ala-Glu SEQ ID NO. 39 (11-42) peptide fragment:
Glu-Val-His-His-Gln-Lys-Leu-Val-Phe-Phe-Ala-Glu- Asp-Val-Gly-Ser-Asn-Lys-Gly-Ala-Ile- SEQ ID NO. 40 (11-40) peptide fragment:
Glu-Val-His-His-Gln-Lys-Leu-Val-Phe-Phe-Ala-Glu- Asp-Val-Gly-Ser-Asn-Lys-Gly-Ala-Ile-Ile-Gly-Leu- Met-Val-Gly-Gly-Val-Val SEQ ID NO. 41 (12-28) peptide fragment:
Val-His-His-Gln-Lys-Leu-Val-Phe-Phe-Ala-Glu-Asp- Val-Gly-Ser-Asn-Lys SEQ ID NO. 42 (17-40) peptide fragment:
Leu-Val-Phe-Phe-Ala-Glu-Asp-Val-Gly-Ser-Asn-Lys- Gly-Ala-Ile-Ile-Gly-Leu-Met-Val-Gly-Gly-Val-Val SEQ ID NO. 43 (17-42) peptide fragment:
Leu-Val-Phe-Phe-Ala-Glu-Asp-Val-Gly-Ser-Asn-Lys- Gly-Ala-Ile-Ile-Gly-Leu-Met-Val-Gly-Gly-Val-Val- Ile-Ala SEQ ID NO. 44 (22-35) peptide fragment:
Glu-Asp-Val-Gly-Ser-Asn-Lys-Gly-Ala-Ile-Ile-Gly- Leu-Met SEQ ID NO. 45 (25-35) peptide fragment:
Gly-Ser-Asn-Lys-Gly-Ala-Ile-Ile-Gly-Leu-Met (1-40)peptide.

EXAMPLE 1

Stable isotope labeled peptides containing a universal reporter peptide U and several peptides concatenated was applied to detect and quantify protein biomarkers in clinical samples, with a focus on markers of lung cancer.

To assess the recovery of the sample preparation method, heavy isotopically labeled synthetic polypeptide standards (comprising up to three proteotypic peptides and a universal reporter U) of human plasma proteins (LDH, NSE, and Myo) were spiked in samples before and after proteolysis. HPLC-MS analyses were performed on a triple quadrupole instrument (TSQ Vantage, ThermoFisher Scientific) in SRM mode. A set of concatenated reference peptides was synthesized based on a list of candidates previously identified. Synthetic polypeptides were obtained from ThermoFisher Scientific (Ulm Germany).

The reporter peptide R was designed with a tryptic cleavage site at the C-terminus. The calibration curves for the universal reporter peptides U were established using dilution series. The relative response factor of each peptide compared to the reporter was readily determined after trypsin treatment exploiting the 1:1 stoichiometry.

A panel of proteins indicative of lung cancer was selected to demonstrate proof-of-principle. For precise quantification of specific proteins, three synthetic concatenated proteotypic polypeptides were generated and analyzed. Plasma samples from lung cancer patients and controls were analyzed.

The concatenated synthetic polypeptides containing a universal reporter enabled precise determination of the quantities of targeted proteins present in the sample using concomitantly multiple reference peptides. This quantification approach was readily implemented in a large scale targeted proteomics workflow.

EXAMPLE 2

Stable isotope labeled peptides containing a universal reporter peptide U and several peptides concatenated were used to detect and quantify protein biomarkers in clinical samples, with a focus on markers of bladder cancer.

Figure 23:
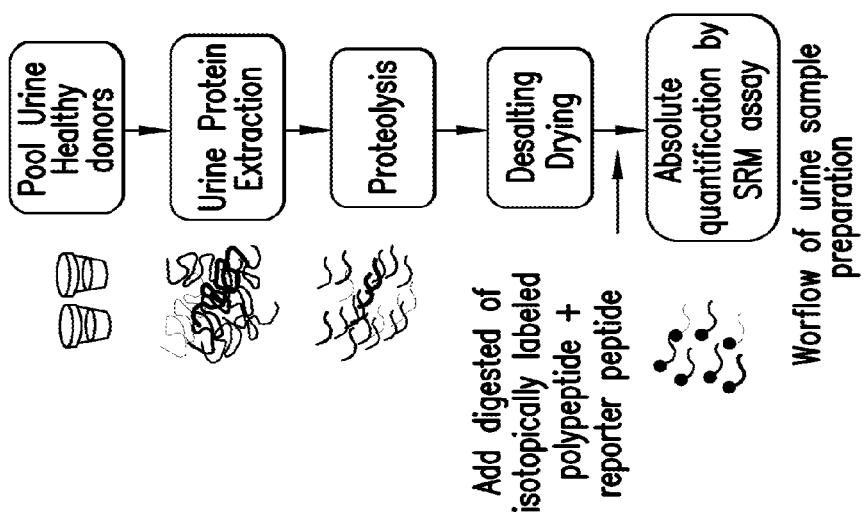
FIG. 23 show one embodiment of sample preparation.
Figure 25:
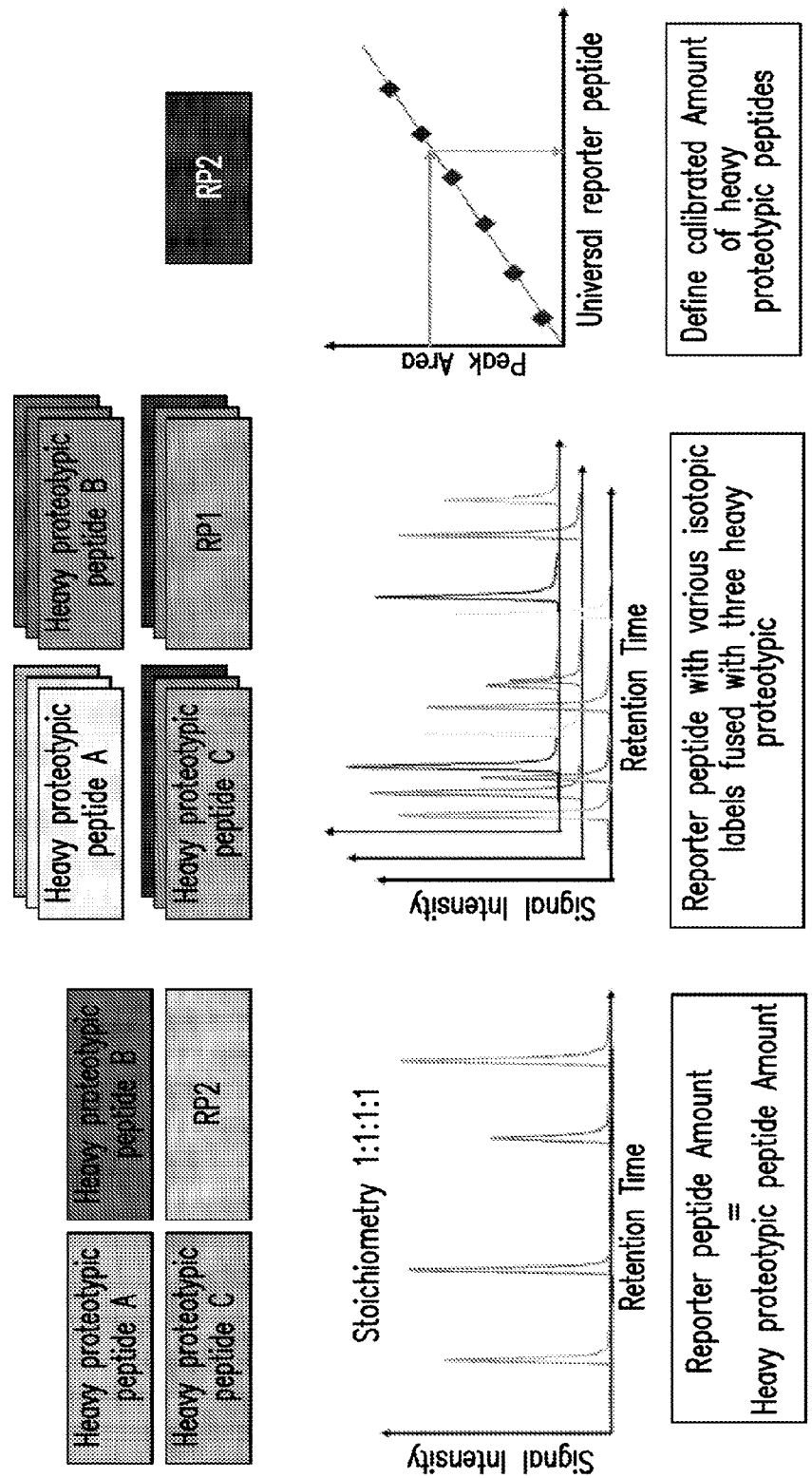
FIG. 25 illustrates quantitation using concatenated heavy isotope labeled proteotypic peptides A-B-C-reporter peptide R2.

Exogenous proteins from yeast (*Saccharomyces cerevisiae*) (ADH, enolase, and carboxypeptidase) and human (LDH, NSE, Myo) were added as internal standards in urine samples, which may be prepared as shown in FIG. 23. The isotopically labeled synthetic polypeptide standards, which were proteotypic peptides of the protein of interest and a universal reporter peptide U, were spiked before proteolysis. Urine samples were prepared by protein precipitation, reduction/alkylation, trypsin proteolysis, and desalting using C18 cartridges. A second set of isotopically labeled synthetic peptides was added after proteolysis.

LC-MS/MS analyses were performed on RP-HPLC (Dionex) coupled with a triple quadrupole instrument (TSQ Vantage, ThermoFisher Scientific) operated in SRM mode. Several transitions were monitored for each targeted peptide. Isotopically labeled synthetic polypeptides were obtained from ThermoFisher Scientific (Ulm Germany).

To establish the methodology, stable isotope-labeled dipeptides containing a universal reporter U were synthesized. The reporter peptide R was designed with a tryptic cleavage or digestion site at the C-terminus. The calibration curves for the universal reporter peptides U were established using dilution series. In parallel, the relative response factor of each peptide compared to the reporter was determined after trypsin treatment exploiting the 1:1 stoichiometry. LC-MS analyses were performed in SRM mode.

To evaluate the methodology, precise quantities of reference polypeptides were spiked into the urine samples, digested with trypsin, and analyzed by LC-SRM to quantify the targeted human proteins. Preliminary results included analysis of insulin-like growth factor binding protein 7 in urine samples using two individual synthetic stable isotope-labeled peptides tagged with a universal reporter U: reporter-HEVTGVWLVSPLSK (SEQ ID NO. 46) and reporter-ITWDALHEIPVK (SEQ ID NO. 47). Dilution curves were generated in pooled urine samples to precisely determine the quantity of corresponding protein: the actual concentrations obtained were 1.49 ng/ml and 1.69 ng/ml, for the two peptides respectively.

EXAMPLE 3

To further evidence the method's utility, large synthetic polypeptides were produced, resulting from concatenation of multiple peptides representing each of the proteins of interest.
Three proteotypic peptides per protein with adequate mass spectrometric properties (precursor m/z, ionization efficiency, retention time, MS/MS spectra) were selected to construct the concatenated standards. These reference polypeptides, all containing a universal reporter, allowed measurement of the precise quantity of multiple reference peptides in one LC-MS run.

EXAMPLE 4

The inventive method decreased mass spectrometry usage to generate a calibration curve, resulting in savings in both instrument usage, operator time, and processing efficiency. In preparing a calibration curve, different peptide concentrations are injected in the LC-MS system. A typical calibration curve requires six peptide injections at different peptide concentrations. Each injection is performed in triplicate (three replicates). The total LC-MS analyses to generate a calibration curve is thus at least 18 analyses.

The peptide LVALV*R* SEQ ID NO. 48 was injected (* indicates a heavy isotope labeled amino acid). The following peptides isomers of SEQ ID NO. 48 were synthesized: LVALVR*, LV*ALV*R*, LVA*L*V*R*, LV*A*L*V*R*, L*V*A*L*V*R* and LVA*LVR (other combination are possible) and provided in equimolar concentration. Two mixtures of these synthesized peptides were prepared. Each mixture had a different concentration of heavy isotope: one mixture had a three fold or three times dilution of each isomer; the other mixture had a five fold or five times dilution between of each isomer. The final mixtures containing the isomers at different concentrations were injected into the LC-MS system. A single injection, with three replicates, was sufficient to generate a complete calibration curve. This method thus further decreased the time needed to generate the calibration curve, and also improved the coefficients of variation among the three replicates.

EXAMPLE 5

Isotopically-Labeled Peptides as Internal Standards

Table 1 lists targeted human urine and yeast proteins, and three selected proteotypic peptides to design HeavyPeptide IGNIS™. As shown in Table 1, ten HeavyPeptide IGNIS™ were designed that corresponded to 30 proteotypic peptides of nine proteins (seven human proteins, three yeast proteins). Stable isotope-labeled amino acids of each HeavyPeptide IGNIS™ (purity >95%, lyophilized in sorbitol) were selected to have a mass change sufficient for MS analysis, with the endogenous peptides and the corresponding individual synthetic stable isotope labeled peptides with C-terminal $^{15}$N- and $^{13}$C-labeled arginine or lysine residue (purity, lyophilized, >99 atom % isotopic enrichment); Table 2 lists the full sequence of the HeavyPeptide IGNIS™ identifying the stable isotope amino acids.

The proteotypic peptides were selected from proteomics shotgun experiments. The reported number of observations was used as a surrogate indicator for the abundance of proteins in a specific proteome. The uniqueness of the peptide reporter was verified by blasting the amino acid sequence, LVALVR, against the UniProt database; this sequence is not associated with a protein.

Calibration Curve of the Peptide Reporter

The calibration curve was performed by mixing the universal reporter peptide U solution (purity >97%) with various isotope label (R for heavy arginine ($^{13}C_6$, $^{15}N_4$); A for heavy alanine ($^{13}C_3$, $^{15}N$); L for heavy leucine ($^{13}C_6$, $^{15}N$); V for heavy valine ($^{13}C_4$, $^{15}N$)). Five µL of LVALVR (0.5 fmol/µL), 15 µL LVALVR (0.5 fmol/µL), 4.5 µL LVALVR (5 fmol/µL), 13.5 µL LVALVR (5 fmol/µL), 40.5 µL LVALVR (5 fmol/µL), 12.2 µL LVALVR (50 fmol/µL), 36.5 µL LVALVR (50 fmol/µL), 109.4 µL LVALVR (50 fmol/µL), and 13.6 µL of 0.1% (v/v) formic acid (in water) were mixed to obtain a final volume of 250 µL. Concentrations of these peptides in solution are 10.0 atmol/µL, 30.0 atmol/µL, 90.0 atmol/µL, 270.0 atmol/µL, 810.0 atmol/µL, 2.4 fmol/µL, 7.3 fmol/µL and 21.9 fmol/µL, respectively. Analysis of the calibration curve was performed in triplicate by one LC-SRM run on the TSQ-platform. The two most intense transitions derived from the SRM assay were monitored for the reporter peptide.

Figure 9A:
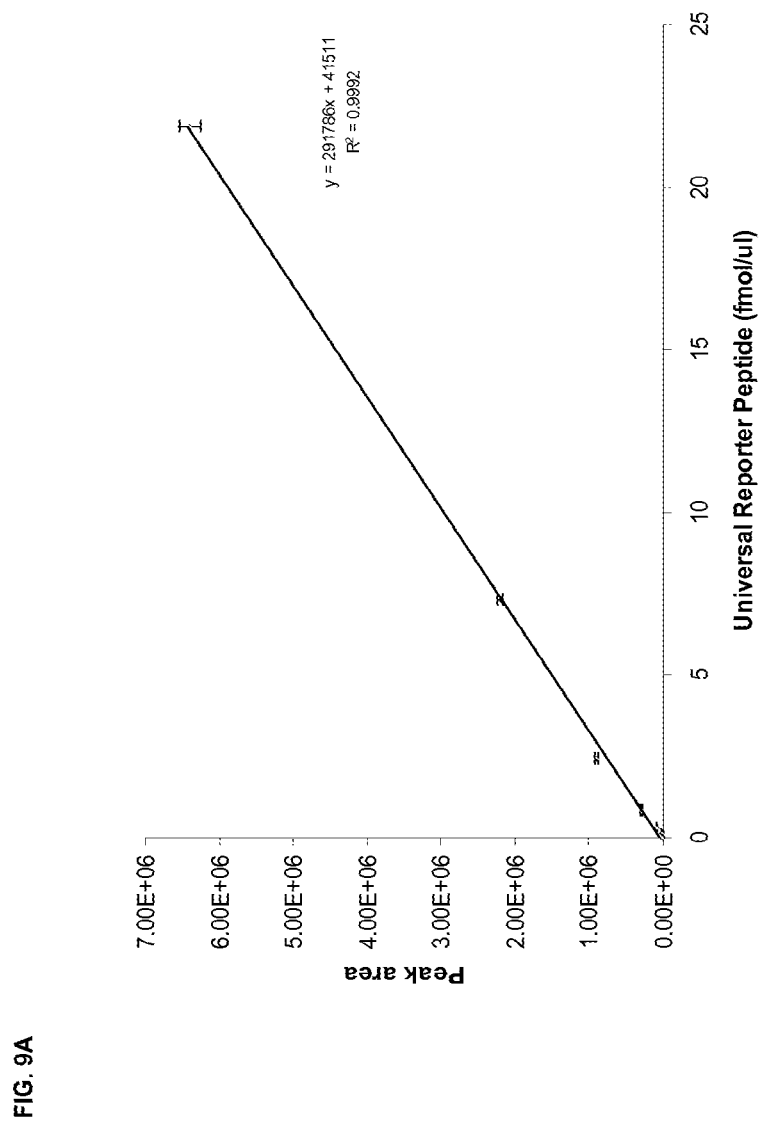
FIG. 9A shows results of a dilution series of one universal reporter peptide U using a linear scale.
Figure 9B:
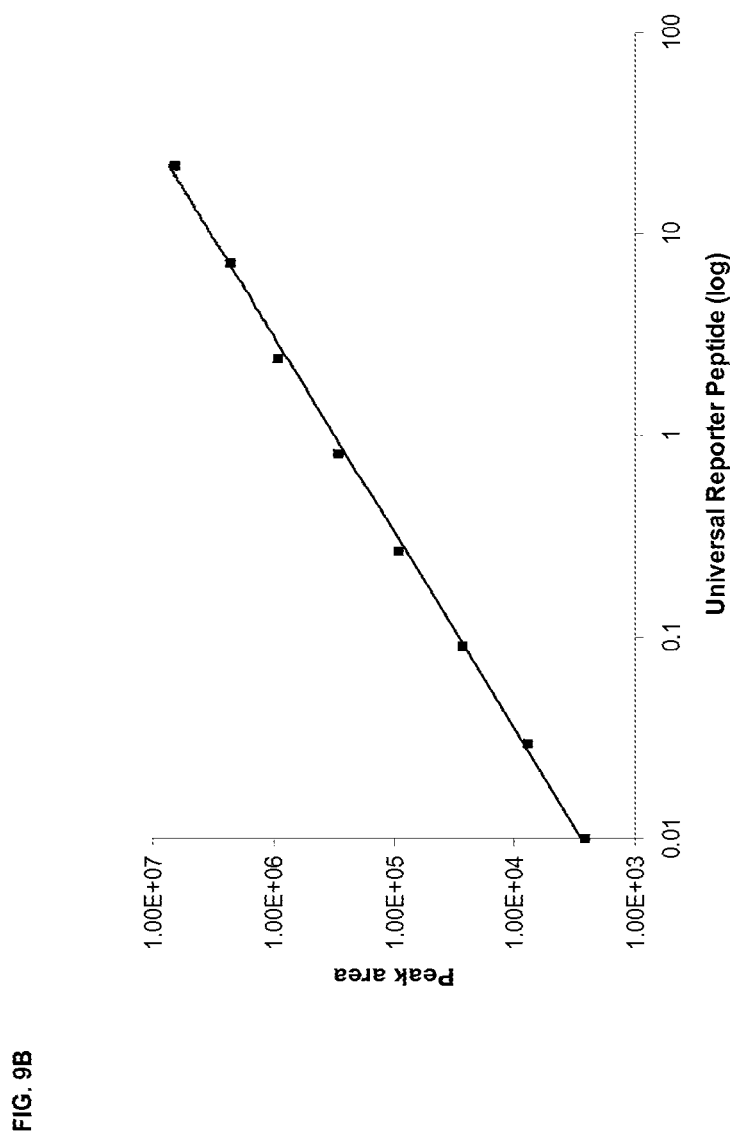
FIG. 9B shows results of a dilution series of one universal reporter peptide U using a logarithmic scale.

The results of the "dilution series" of the universal reporter peptide U=LVALVR are shown in FIG. 9. Various isotopic labels, ranging from 0.01 fmol (injected)-21.9 fmol (injected) are shown in linear (FIG. 9A) and logarithmic scales (FIG. 9B). The dilution series was measured in one single LC-MS run. Peak area ratios were determined from the mean of two SRM transitions. Each data point corresponds to the dilution series that was measured in triplicate. A linear standard curve was observed ($r^2$>0.999) between 10.0 atmol/µL and 21.9 fmol/µL.

Proteolysis of HeavyPeptide IGNIS™

Each HeavyPeptide IGNIS™ was solubilized with acetonitrile (ACN)/water (15/85) (vol/vol) to obtain a final protein concentration of 5 pmol/µL, and then sonicated for 20 minutes. HeavyPeptide IGNIS™ were individually digested by trypsin 1:20 (w/w) (Promega, Madison Wis.) for 3.5 hr at 38° C. under agitation (1400 rpm). The kinetic digestion was monitored by reaction mixture extraction every 15 minutes. To stop the digestion, all samples were diluted in 0.1% v/v formic acid to obtain a final peptide concentration of 50 fmol/µL for analysis on LC-MS (in SRM mode).

Figure 10:
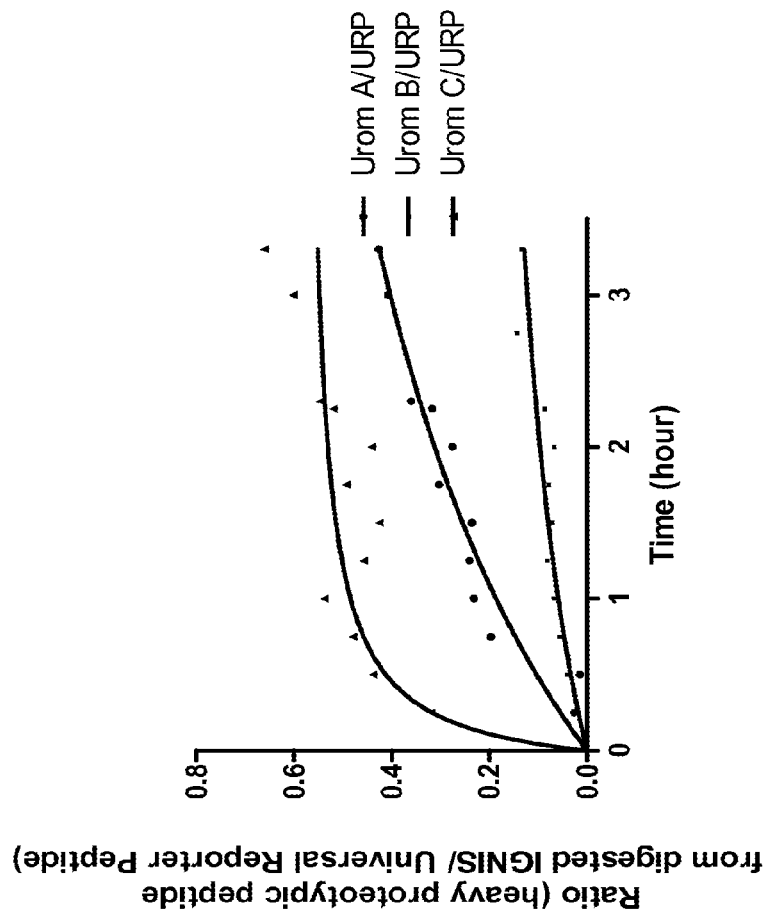
FIG. 10 shows proteolysis efficiency of an exemplary heavy isotope labeled peptide.

For quantitative measurements on TSQ-platform, all HeavyPeptide IGNIS™ digestion kinetic points were stoichiometrically supplemented with the corresponding individual synthetic stable isotope-labeled peptides with C-terminal $^{15}$N/$^{13}$C-labeled arginine or lysine residue (AquaUltimate) and the universal reporter peptide U=LVALVR. The two most intense transitions observed from the SRM assay were monitored for all peptides. FIG. 10 shows proteolysis efficiency of the HeavyPeptide IGNIS™ UROM. Proteolytic kinetics of HeavyPeptide IGNIS™ UROM was established by nonlinear regression of each heavy proteotypic peptide (UROM A, UROM B, and UROM C) from digested HeavyPeptide IGNIS™ UROM/universal reporter peptide U area ratio versus time of the proteolysis. The last points of kinetic were used to define the precise quantity of each HeavyPeptide IGNIS™.

Urine Collection and Sample Treatment

Spot midstream urine samples were collected from ten non-smoking healthy volunteers, five females and five males, age range 30-40 years. There was no history of renal dysfunction in any of the subjects or drug administration during the sample collection. Urine was centrifuged at 1 000 g relative centrifuge force (rcf) per 20 minutes at room temperature (about 19° C.-22° C.). The supernatants 1 000 g were pooled together, portioned into aliquots in 50 Falcon™ tubes and stored at −80° C.

The quantity of urinary protein was estimated by a pyrogallol assay. Samples corresponding to 250 μg of urinary protein were precipitated with 100% stock solutions of acetonitrile (for HPLC) at a ratio 1:5 (v/v). Samples were incubated at room temperature overnight. After precipitation, urine samples were centrifuged at 14,000 g for 30 minutes at 4° C. The pellet was washed once with the acetonitrile, air-dried. and resuspended with 250 μL 8 M urea and 0.1 M ammonium bicarbonate. The samples were reduced with 20 mM dithiothreitol in 50 mM ammonium bicarbonate at 37° C., centrifuged at 800 rpm for 30 minutes, then alkylated with 80 mM iodoacetamide in 50 mM ammonium bicarbonate at 37° C. and centrifuged at 800 rpm for 30 min. Volume samples were adjusted at 2 M urea with 100 mM BA. Samples were then digested with trypsin (Promega, Madison Wis.) using a ratio of 1:20 (w/w) at 37° C. overnight. Digestion was halted by adding formic acid to obtain a pH 2-3. Sep-Pak C18 reverse phase cartridges, 100 mg (Waters, Milford Mass.) were used to clean and desalt the samples after protein digestion. The peptides were eluted using 1 mL of 50% acetonitrile and 0.1% formic acid, dried, and stored at −20° C. until LC-MS analysis.

Calibration Curve of HeavyPeptide IGNIS™ and AquaUltimate in Urine Samples

Figure 11:
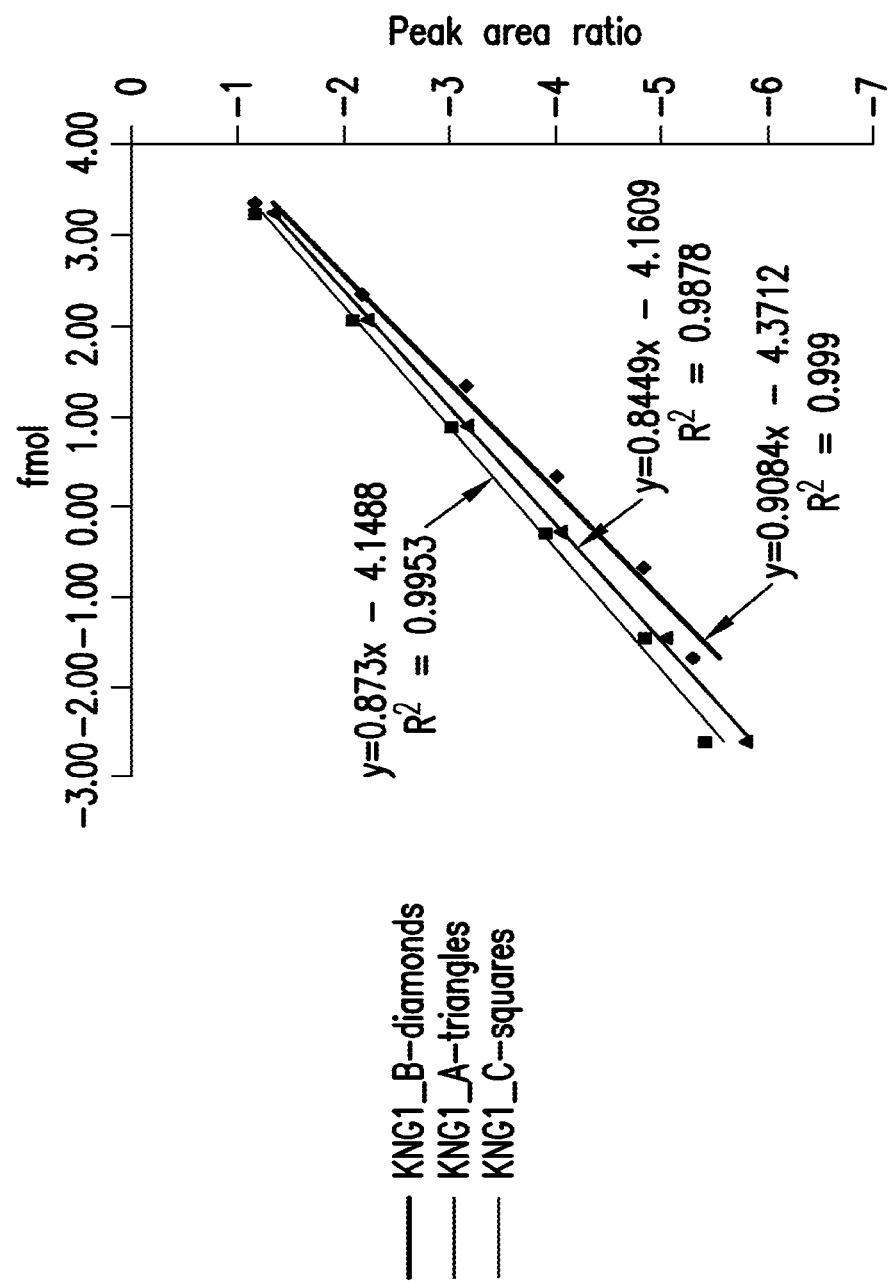
FIG. 11 shows data for an exemplary heavy isotope labeled peptide.

Dilution curves of the heavy proteotypic peptides from digested HeavyPeptide IGNIS™ were performed in a mixture of digested pooled urine sample (1 ug/mL urine proteins), containing three digested exogenous yeast proteins (carboxypeptidase Y, enolase 1, and alcohol dehydrogenase 1) at 100 ng/mL individually. Each dilution series corresponded to three data points spanning a concentration ranging from 0.002 fmol/uL to 40 fmol/uL. Protein levels of spiked digested yeast proteins and human urine proteins were determined by iSRM using the heavy proteotypic peptides from digested HeavyPeptide IGNIS™. FIG. 11 shows a dilution curve of the heavy proteotypic peptides from the digested HeavyPeptide IGNIS™ KNG1 from 0.002 fmol/μL to 40 fmol/μL on a logarithmic scale. Peak area ratios were determined from the mean to two SRM transitions. Each data point corresponded to the dilution series that was measured in triplicate. FIG. 11 and Table 3 show data for the HeavyPeptide IGNIS™ Kininogen 1 (KNG 1).

LC-MS Conditions

Urinary and yeast tryptic peptides were analyzed on a TSQ Vantage Triple Quadrupole Mass Spectrometers (ThermoFisher, San Jose Calif.). Instruments were equipped with a nanoelectrospray ion source. Chromatographic separations of peptides were performed on an Ultimate 3000 (Dionex, Netherlands) high performance liquid chromatographer operated in the nano-flow mode. Samples were loaded on a Trap column (Acclaim PepMap C18, 3 μm, 100 Å, 0.075×20 mm, Dionex) and separated on an analytical column (Acclaim PepMap® RSLC C18, 2 μm, 100 Å, 0.075×150 mm, Dionex) coupled with a PicoTip™ electrospray emitter (30 μm) (New Objective, Woburn Mass.) maintained at 1.2 kV. The column temperature was fixed at 35° C. Peptides were separated with a linear gradient of acetonitrile/water, containing 0.1% formic acid, at a flow rate of 300 nL/min. A gradient from 2% to 35% acetonitrile in 33 minutes was used. One μL of each sample was injected. The mass spectrometer was operated with intelligent-selected reaction monitoring (i-SRM). For acquisitions, the mass selection window of Q1 and Q3 were 0.7 unit mass resolution. An acquisition time window of 2 min was set around the elution time of the peptide. Argon was used as the collision gas at a nominal pressure of 1.5 mTorr. Collision energies for each transition were calculated according to the following equations: CE=0.033*(m/z)+1.8 and CE=0.038*(m/z)+2.3 (CE, collision energy and m/z, mass to charge ratio) for doubly and triply charged precursor ions, respectively. For the i-SRM acquisition, two primary and six secondary fragment ions were selected per peptide, based on the full MS/MS spectrum stored in a database. The scan time for the triggered SRM measurements was 200 ms. Dynamic exclusion for the triggering of the data-dependent SRM was enabled with a threshold intensity of 100 counts, with a repeat count of three cycles and a dynamic exclusion of 20 seconds. The i-SRM data were processed using Pinpoint software (Thermo Fisher, San Jose Calif.).

EXAMPLE 6

Table 4 lists identifications and characterizations for selected human and yeast HeavyPeptide IGNIS™ peptides used as disclosed. The peptides were in a lyophilized formulation, purity >95%. The universal reporter peptide U was LVALVR, with a mass difference (delta mass) versus the natural sequence=16. Table 5 lists commercially available peptides having the same sequence but having a different mass due to a difference in heavy labeled amino acid, that may be used as additional peptides in the disclosed method.

EXAMPLE 7

Sensitivity limits included both limits of detection (LOD), and limits of quantitation (LOQ). Variability in LOD and LOQ is due to multiple factors, including but not limited to different liquid chromatography equipment and conditions, material, etc.). The common source is nonspecific binding of the peptide to the tubing, column, etc. The LOD and LOQ are traditionally determined by injecting more and more diluted peptides into the system. The lower the concentration, the higher the chance to lose part or all the peptide.

The dilution series of Example 5 was used to assess sensitivity limits of MS equipment. Specifically, the following sequences were included in the mixture: LVALVR, LVALVR, LVALVR, LVALVR, LVALVR, and LVALV. The mixture contained a blend of different isomers, termed isotopologues, each having a slight mass shift, and each present in a different concentration, such that the entire calibration curve was generated in one single LC analysis or run.

Figure 12:
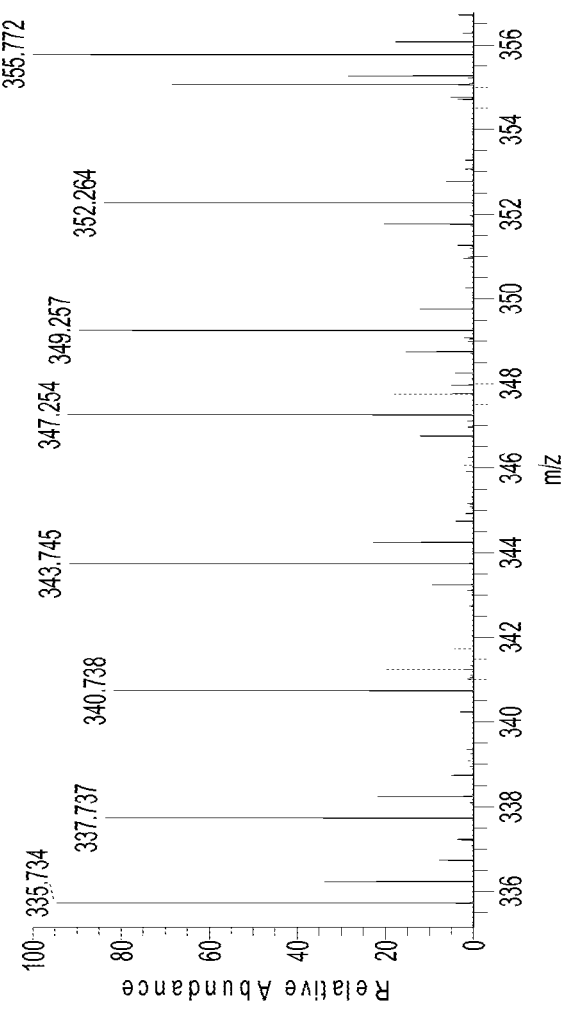
FIG. 12 shows a spectrograph of isotopologues.

In one evaluation of quantification performance, the following results were obtained from a peptide composition that was a blend or mixture of eight peptides and each peptide in the composition had the identical amino acid sequence but different amino acids in the peptide were labeled or modified with a stable heavy isotope. Each isomer in the blend had a mass shift, and each isomer in the blend was present in a different concentration. The dilution spanned a 3.3 logarithmic range, specifically, from 10 amol to 20 fmol. For data acquisition the resolution was 70,000; the maximum injection time was 250 ms, and the automatic gain control (AGC) target values were 1E5, 5E5, 3E6. The results are shown in FIG. 12 and in the following table.

| m/z $[M + 2H]^{2+}$ | Peptide | Quantity |
| --- | --- | --- |
| 335.73 | LVALVR | 10 amol |
| 337.74 | LVALVR | 30 amol |
| 340.74 | LVALVR | 90 amol |
| 343.74 | LVALVR | 270 amol |
| 347.25 | LVALVR | 810 amol |
| 349.26 | LVALVR | 2.4 fmol |
| 352.26 | LVALVR | 7.3 fmol |
| 355.77 | LVALVR | 21.9 fmol |

Figure 16:
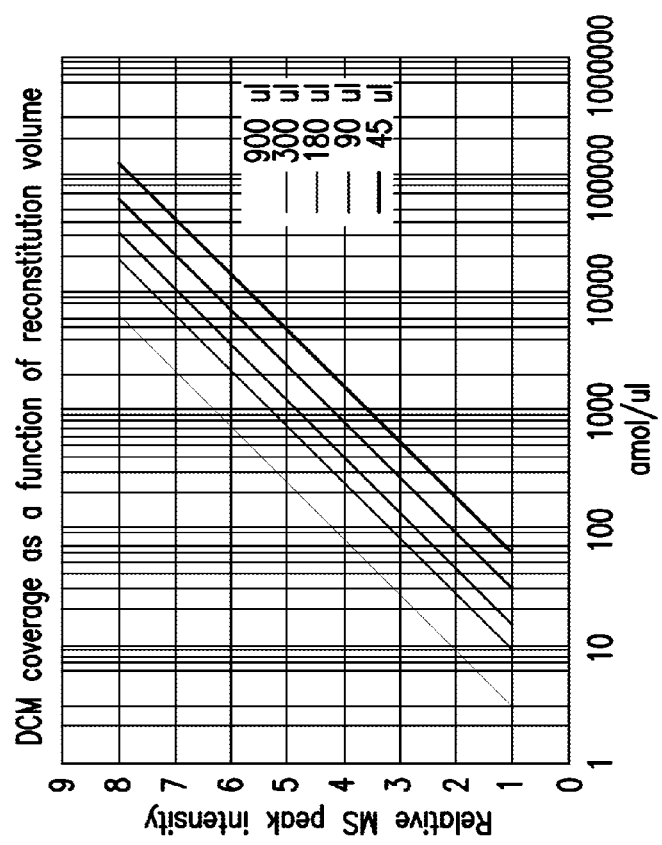
FIG. 16 shows data evidencing a single injection dilution curve generation by mass spectrometry.
Figure 21:
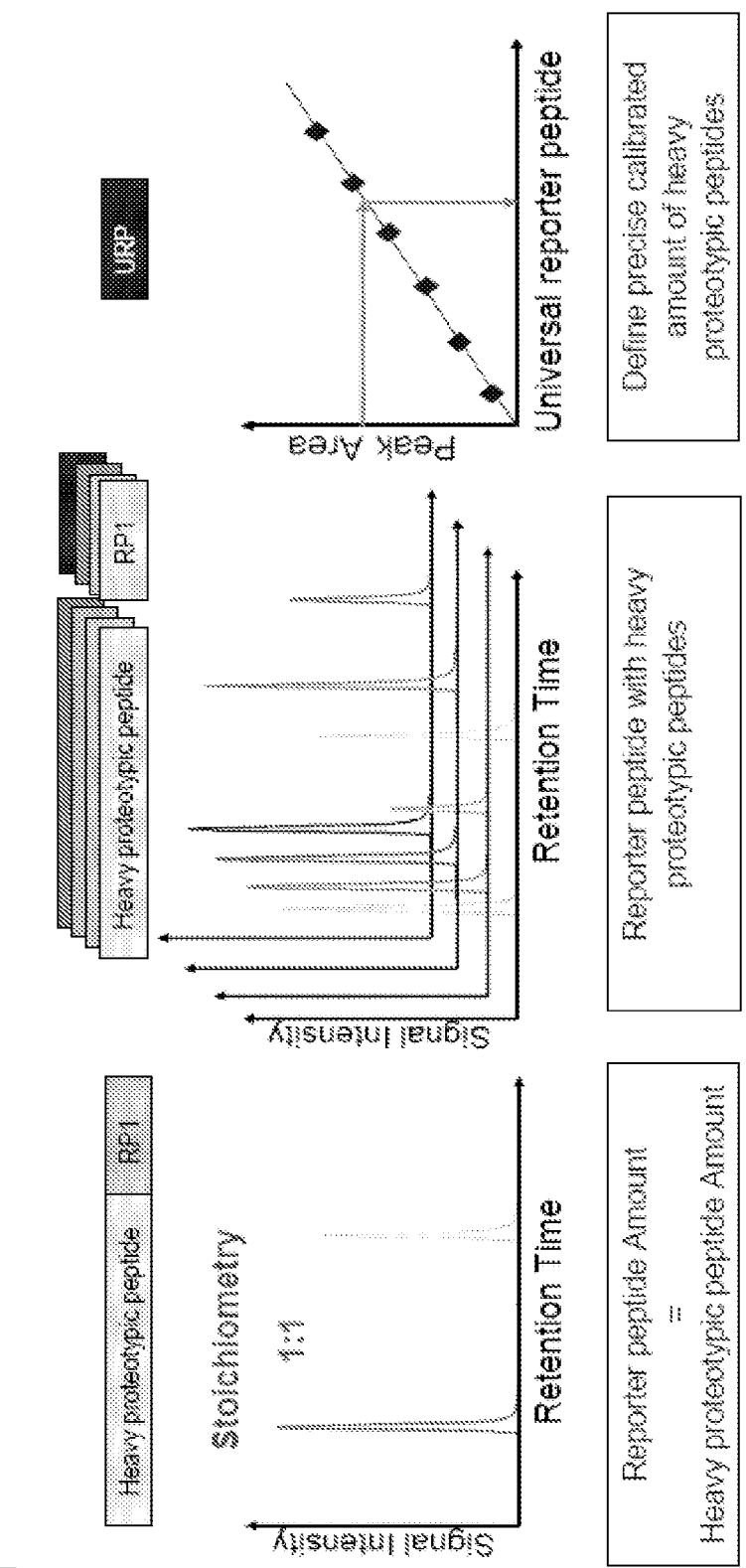
FIG. 21 illustrates quantitation using a heavy isotope labeled proteotypic peptide-reporter peptide R1.

Data supporting use of a dilution curve mixture or blend for single injection dilution curve generation are shown in FIG. 16. The distribution of medium and low abundant protein spread from 1 pmol per 100 µl sample to <1 amol per 100 µl sample. To cover 80% of the medium-to-low abundance proteins, the dilution curve mixture (DCM) should cover up to 0.1 pmol per 100 µl of the final sample. The DCM is lyophilized so it can be reconstituted in any buffer, including complex matrices such as plasma, urine, other body fluid, or cell extract. Reconstituting the DCM in 900 µl, compatible with the volume of a standard vial, provides 3 amol per 1 µl for the lowest concentrated isomer. FIG. 17, providing data from a dilution curve mixture, gives the concentration per µl for the lowest concentrated and highest concentrated isomer mixtures or blends. Each peptide had >97% purity. To prepare the dilution curve mixture, 45 µl of the isomer mixture or blend in 50 mM sorbitol was lyophilized in standard glass vials. Information on the isomers, including sequences and concentrations, used to generate the dilution curve mixture is provided in FIG. 18. In one embodiment, the isotopologue mixture or blend contains the isomers listed in FIG. 19 and the sequences listed in FIG. 20 as internal standards bracketing controls.

Figure 13A:
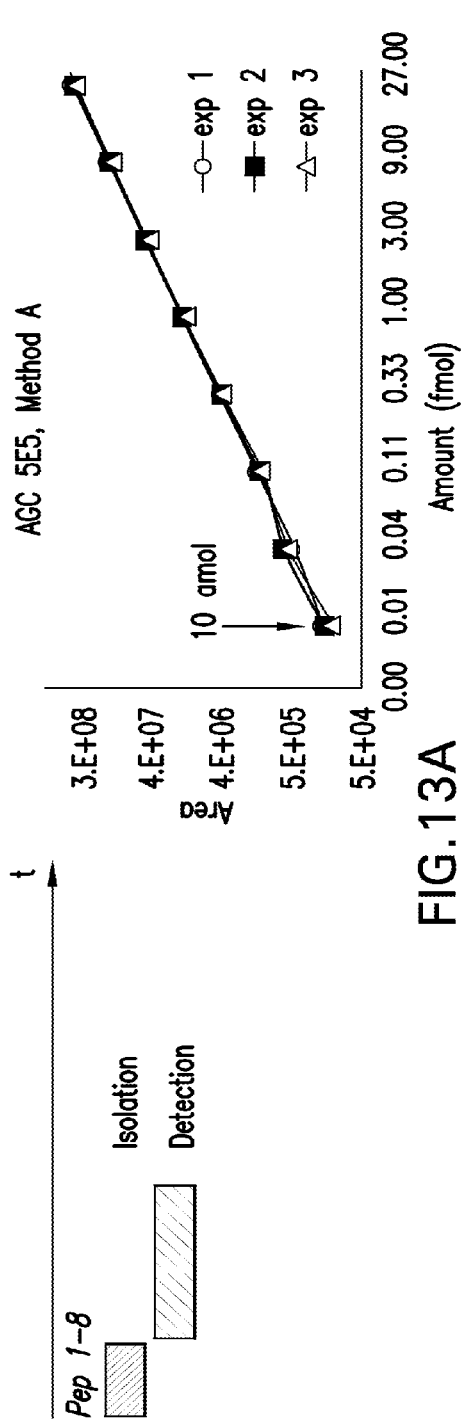
FIG. 13A shows results of secondary ion mass (SIM) method A.
Figure 13B:
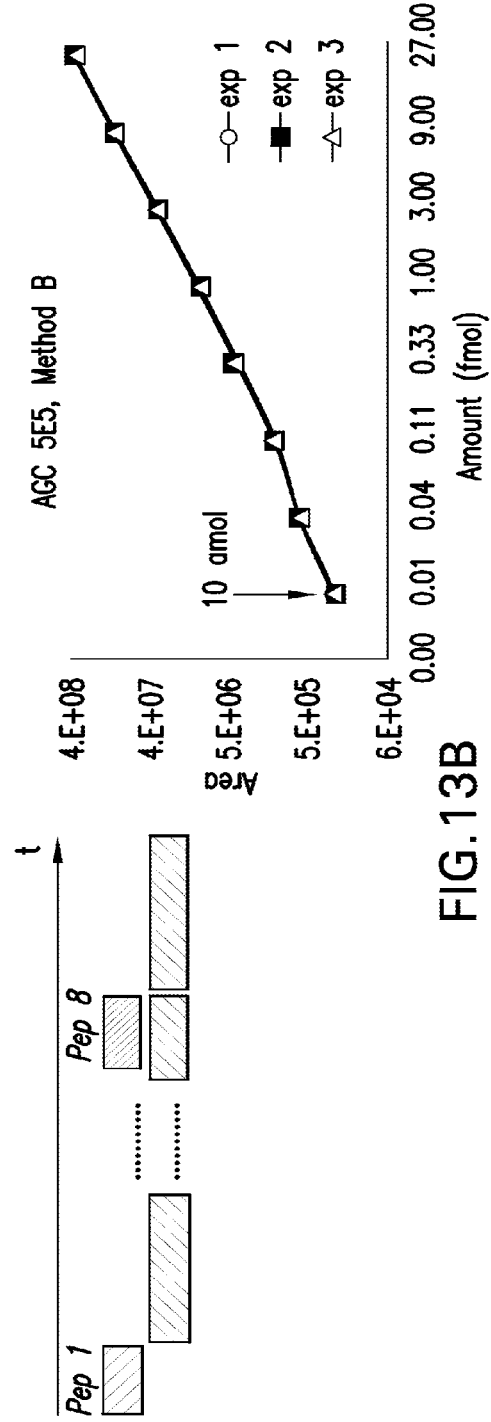
FIG. 13B shows results of secondary ion mass (SIM) method B.
Figure 13C:
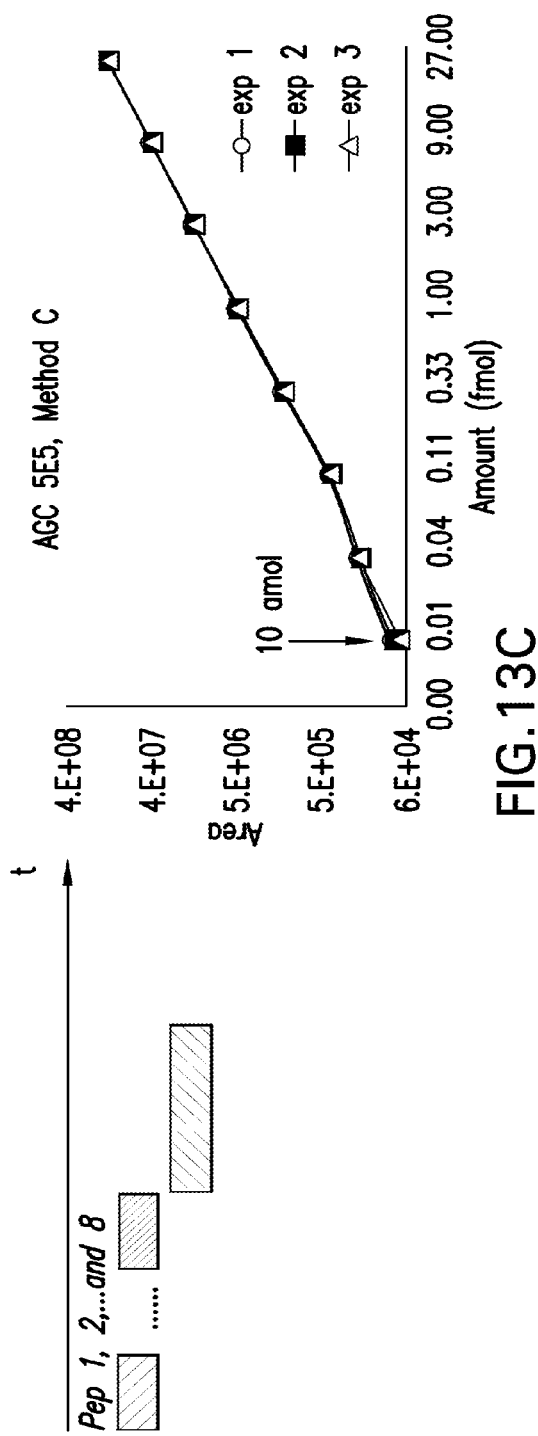
FIG. 13C shows results of secondary ion mass (SIM) method C.

Various secondary ion mass (SIM) methods were evaluated as further described with results shown in FIGS. 13A, 13B, and 13C. Method A used one isolation window (30 m/z), a cycle time of about 0.3 s, and one detection scan; the results are shown in FIG. 13A. Method B used eight isolation windows (2 m/z), a cycle time of about 3.2 s, and eight detection scans; the results are shown in FIG. 13B. Method C used eight isolation windows (2 m/z), a cycle time of about 1.7 s, and one detection scan; the results are shown in FIG. 13C.

The results showed that the method resulted in enhanced sensitivity. The LOQ were in the 10 amol range. The intra-scan linearity exceeded a 3.5 logarithmic range, from 10 amol to 25 fmol.

This method avoided the loss of peptide problem (e.g., nonspecific binding to the column, etc.) because all the isomer mixtures, having the same peptide sequence, co-eluted. The concentration of the most abundant isomer was higher than the concentration of the most diluted isomer, decreasing the loss of the less abundant isomer by non-specific binding. The concentration of isomer at the highest concentration of peptide was 1000, 3000, or 10000 times higher than the concentration of isomer at the lowest concentration of peptide. The risk of losing the isomer with the lowest concentration was very low. This mixture was ideal to compare LOD and LOQ from instrument to instrument, brand to brand, and/or day to day on same instrument, and resulted in more robust quantitative MS.

EXAMPLE 8

Figure 14:
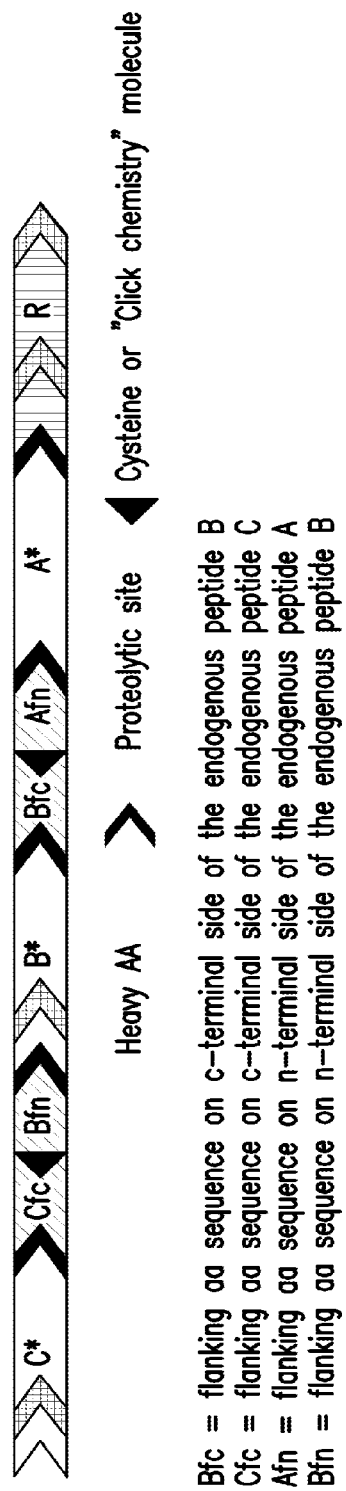
FIG. 14 schematically shows use of flanking amino acid sequences in generating a universal reporter R.

Production of a relatively long universal reporter (Heavy-Peptide IGNIS™) (≥40 amino acids), was facilitated using linkers and chemical ligation. Because it is challenging to synthesize and purify such relatively long peptides, it is often easier to synthesize and purify shorter peptides and assemble these fragments into the final polypeptides. The assembly is done through chemical ligation or using "Click Chemistry", defined as using reactions that are high yielding, wide in scope, creating only byproducts that can be removed without chromatography, are stereospecific, are simple to perform, and can be conducted in easily removable or benign solvents. In both cases a sequence "linker" is added between one or more of the proteotypic peptide as the necessary molecule for the chemical ligation (Cys) or the "click Chemistry" molecule. The linker may be an amino acid sequence, poly(ethylene)glycol (PEG), or any other molecule that can be synthesized as a polymer, as is known to one skilled in the art. When the linker is an amino acid sequence, in one embodiment, the natural flanking regions on the endogenous peptide analyzed are used as a surrogate of protease digestion efficiency, as shown schematically in FIG. 14.

EXAMPLE 9

Stable heavy isotope labeled proteins containing a reporter were synthesized. Two different patterns of isotopically labeled universal reporters U were used. Linear standard curves were obtained ($r^2=0.999$) by monitoring the three most intense selected reaction monitoring (SRM) transitions. The relative response factor of each peptide, compared to the reporter R, was determined after proteolysis (1:1 stoichiometry). The results are shown in FIG. 22 with two different reporters R and two heavy proteotypic peptides for one protein using the same reporter R.

EXAMPLE 10

Figure 26B:
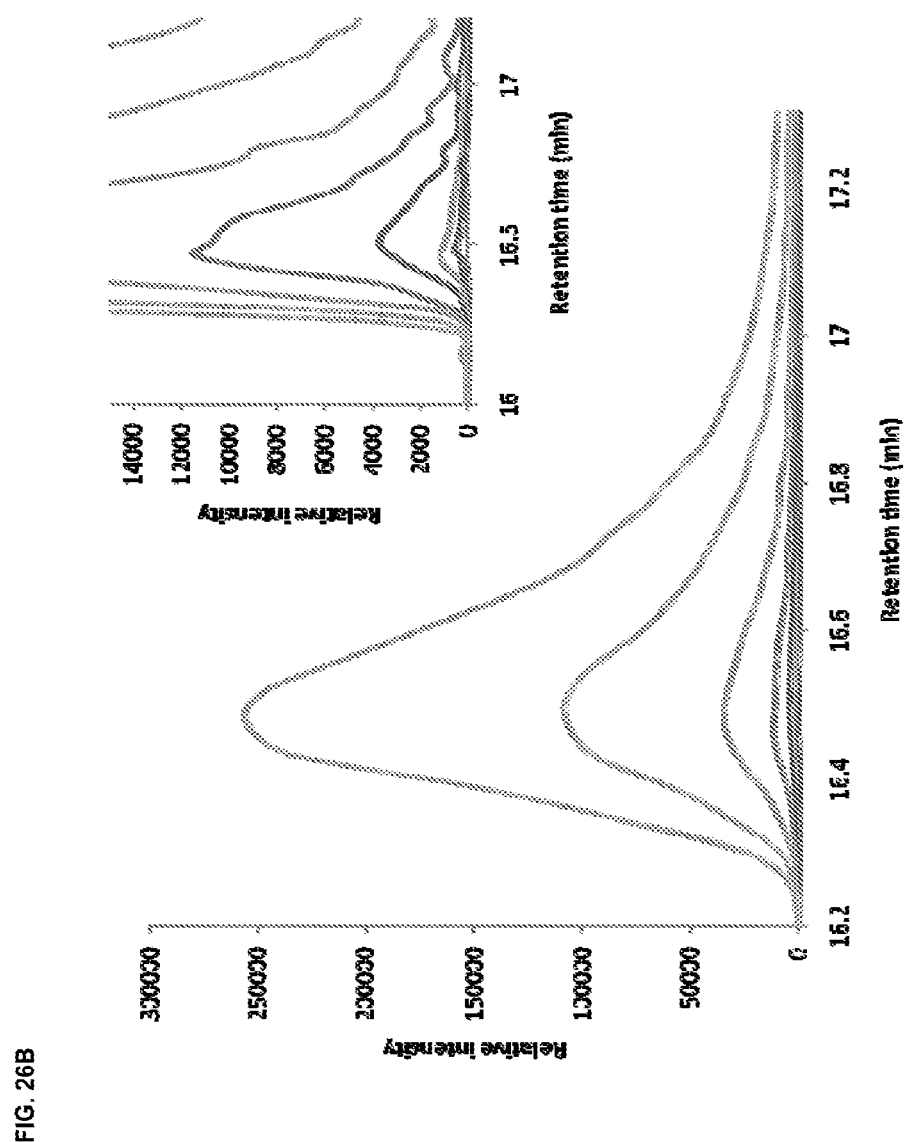
FIG. 26B shows calibration curve data.
Figure 27A:
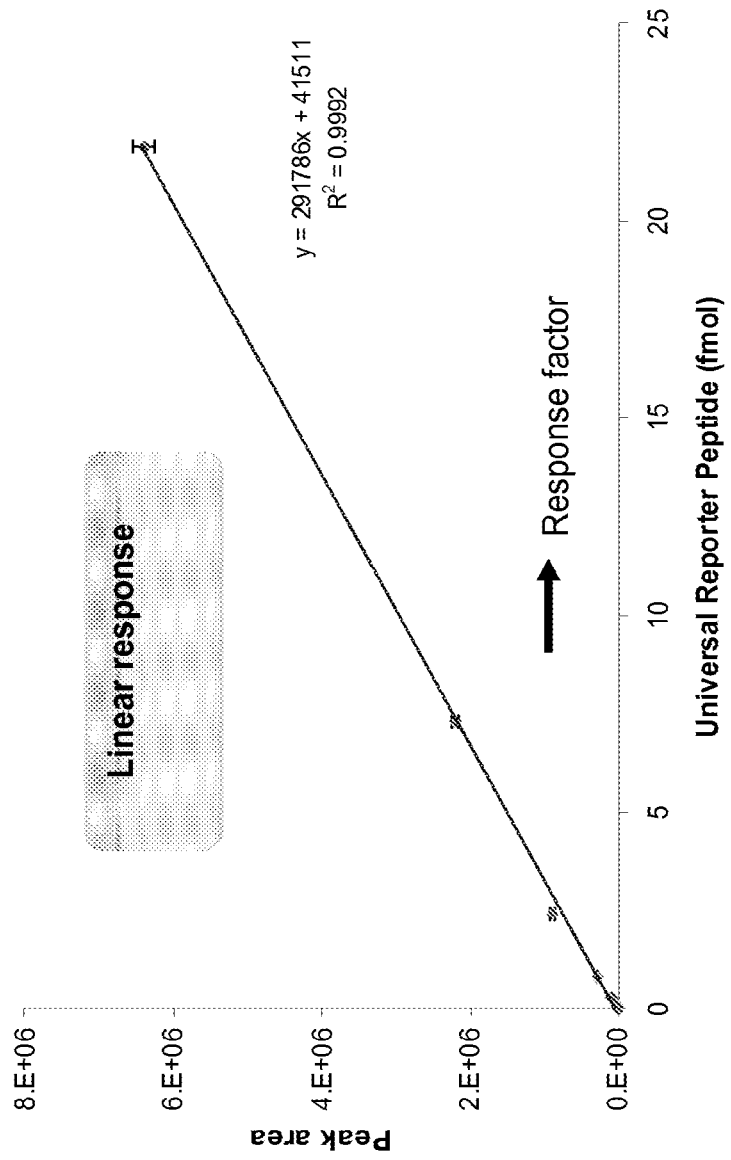
FIG. 27A is a graph of FIG. 26B data showing linear response.
Figure 27B:
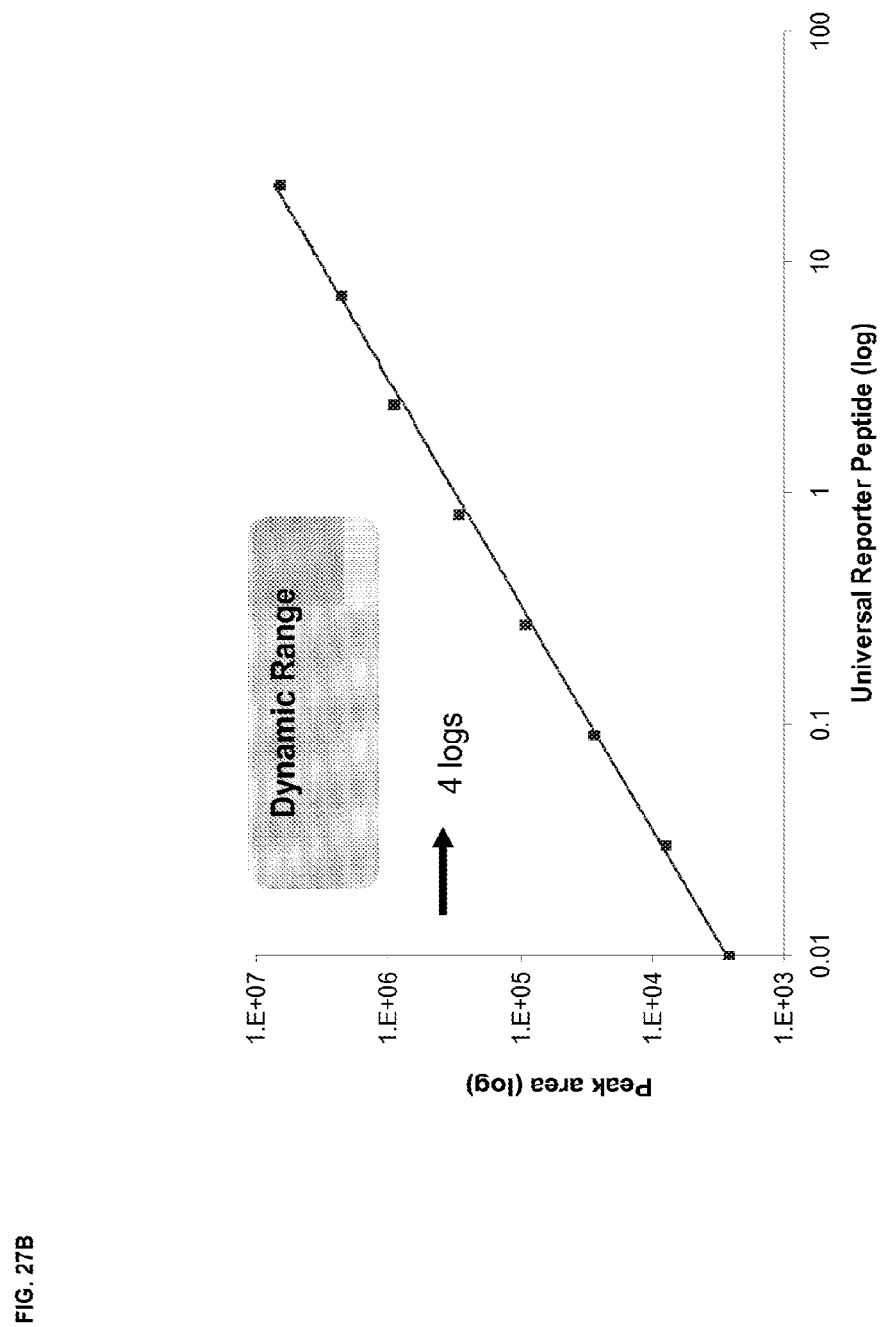
FIG. 27B is a graph of FIG. 26B data showing dynamic range.

Data for a dilution series to generate a calibration curve using a universal peptide U are shown in FIG. 26A and FIG. 26B, respectively. The universal peptide U was LVALVR SEQ ID NO. 48; various heavy isotope labels in quantities ranging from 10 amol to 20 fmol were injected. FIG. 27 is a graph of these data with linear (FIG. 27A) and logarithmic (FIG. 27B) scales. The dilution series was measured in one single LC-MS analysis or run. Peak area ratios were determined from the mean of three SRM transitions in triplicate measurements.

EXAMPLE 11

Figure 28A:
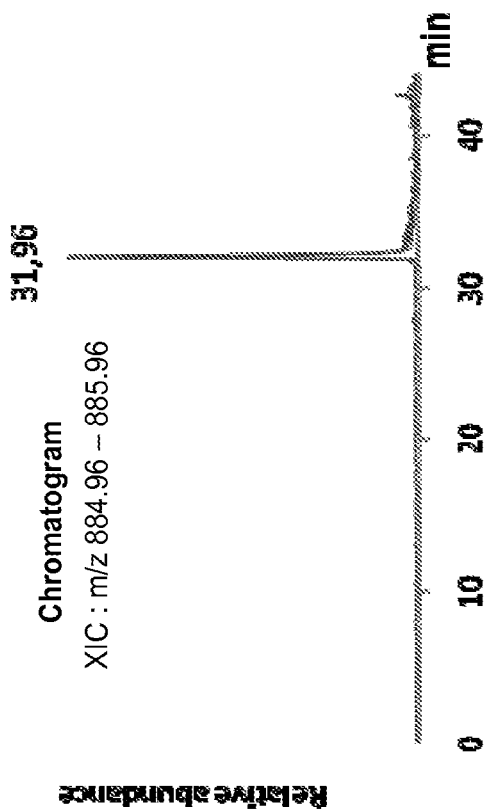
FIG. 28A shows quality control chromatography data for one sequence.
Figure 28B:
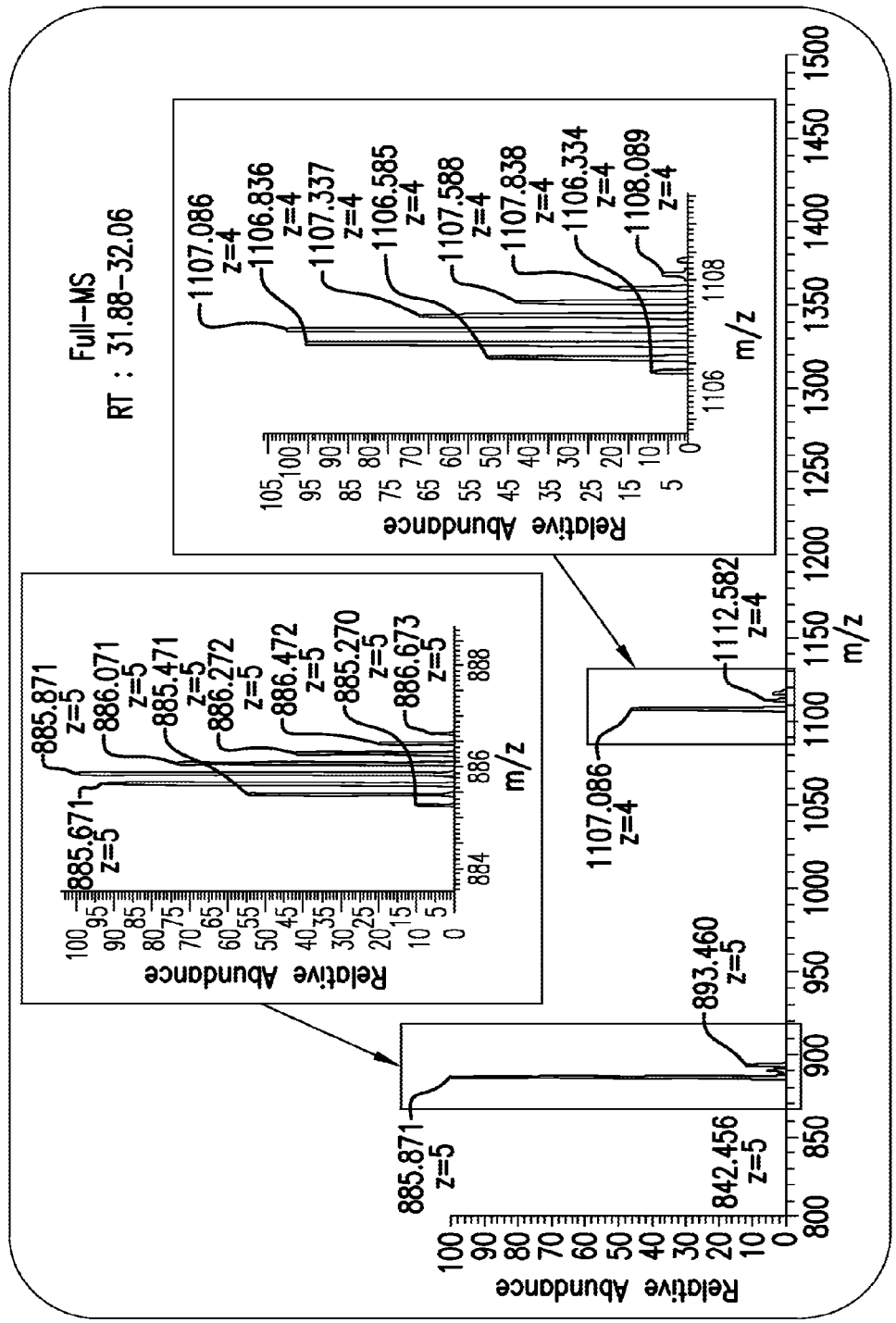
FIG. 28B shows quality control mass spectrometry data for one sequence.
Figure 30:
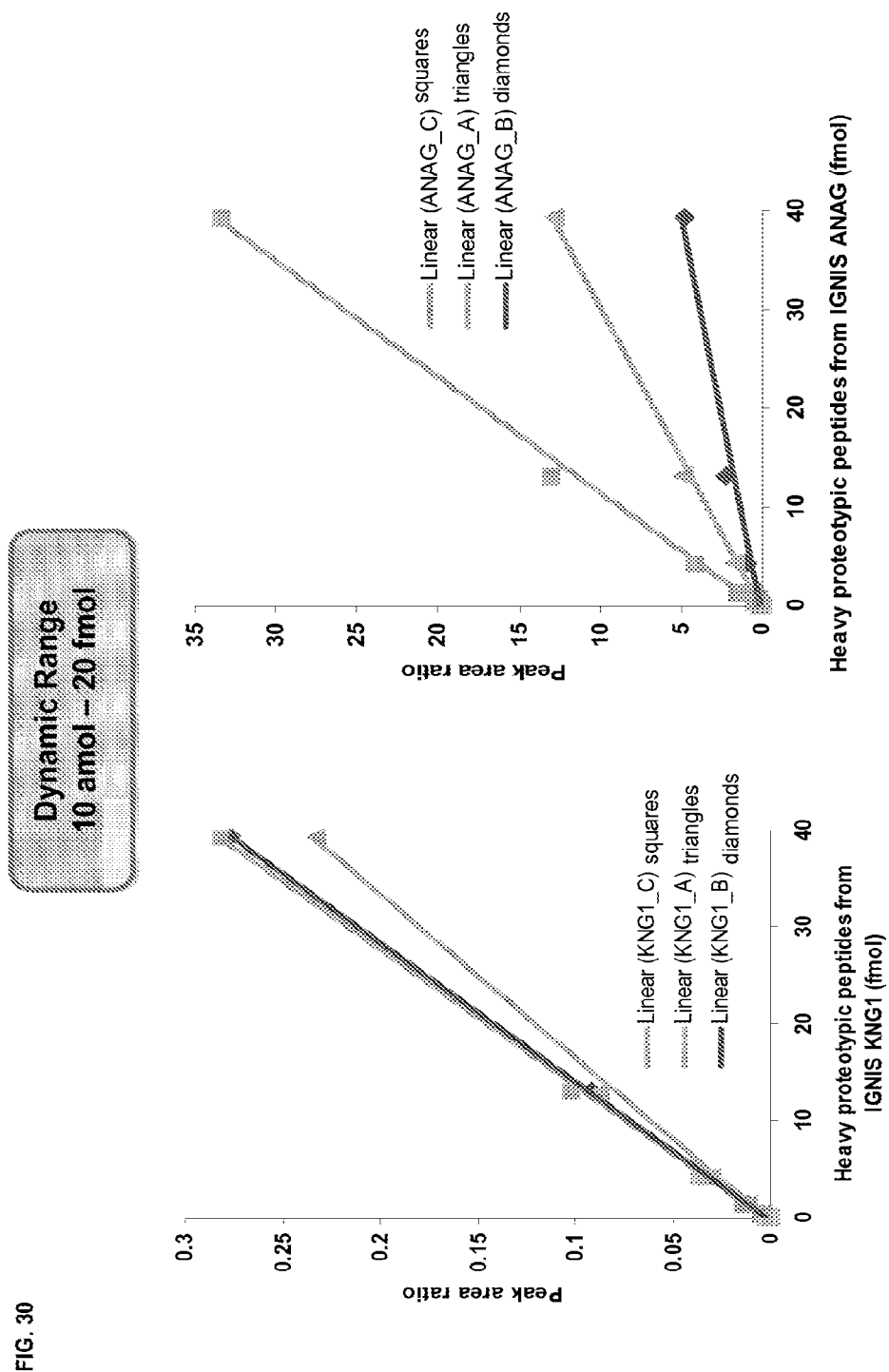
FIG. 30 shows quantitative analysis for selected peptides.
Figure 31:
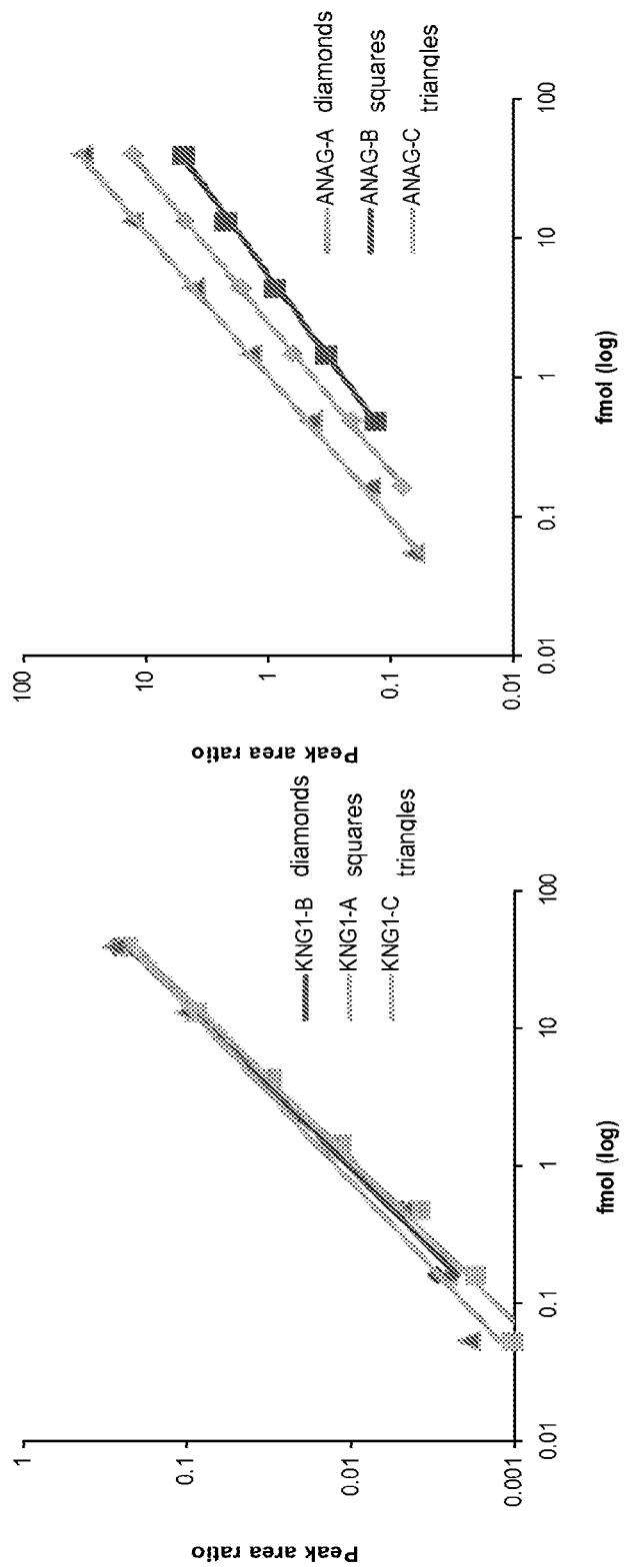
FIG. 31 shows quantitative analysis for selected peptides.

Quality control of the non-digested heavy labeled peptides was performed using uromodulin (UROM) DWVSVVTPA*RDSTIQVV*ENGESSQGRSGSV*ID QSRLVALVR* (SEQ ID NO. 53). Results are shown in FIGS. 28-31. The chromatogram and full MS spectra are shown in FIG. 28. The results of a typical example demonstrating the limits of detection (LOD) and limits of quantitation (LOQ) using the digested peptides indicated, and the corresponding protein quantities measured in urine by i-SRM experiments, are shown in FIG. 29. Calibration curves for the indicated protein in pooled urine samples are shown in FIG. 30 in linear scale, and FIG. 31 in logarithmic scale.

Sensitivity limits include both limits of detection (LOD) and limits of quantitation (LOQ). The inventive method and kit have application for use with next generation mass spectrometers using specific data acquisition methods, specific data processing methods, related instrumentation, etc.

Data processing allows peptides and related isoforms to be grouped, using specific m/z values for precursors and product ions to differentiate signals from each isoform. Such grouping permits relative and absolute quantitation.

In one embodiment, a data processing system is used to analyze and determine relative and/or absolute quantities of targeted and non-targeted biopolymers in a biological sample. The method is based on identifying, grouping, and targeting a series of biopolymers related by sequence and/or composition. The targets contain identical sets and orders of amino acid residues that differ by heavy isotopic labeling, side chain modifications, and/or N- or C-terminal modifications resulting in distinct analytical targets separated by m/z values easily distinguished by a mass spectrometer. For related targets, the m/z values are grouped based on, e.g., injection time, dwell time, automatic gain control (AGC) value, and/or charge density in the curved linear ion trap (C-trap). The data acquisition, processing, and reporting schemes can be performed for precursor and/or product ions (MSn) to determine a quantified response for the endogenous as well as the labeled biopolymers; the product ions are labeled using conventional terms defined in classical mass spectrometry (e.g., b-, y-, c-, z-, etc.), as know to the skilled person, to define the specific position of cleavage and site of charge retention. Data acquisition can include determining the targeted biopolymer sequences, differentiating factors, data acquisition strategies, and data processing approaches that can quantify targeted biopolymers using relative and/or absolute quantities for one sample or across a number of samples.

Figure 32:
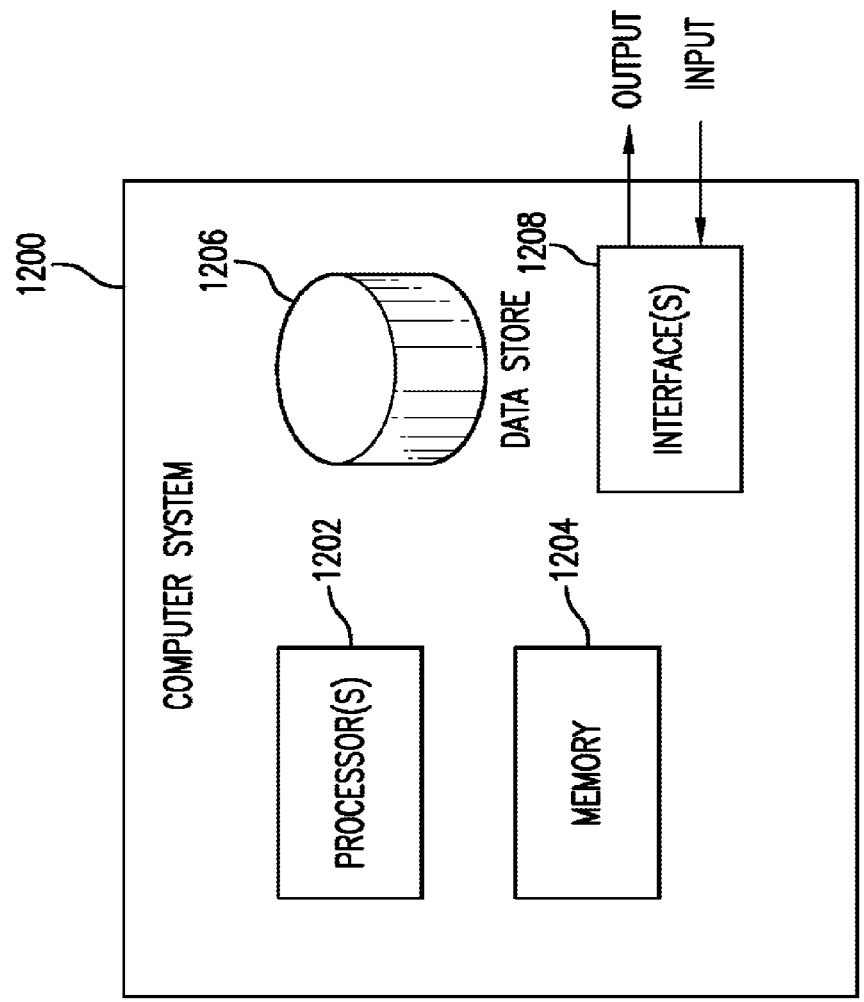
FIG. 32 shows an exemplary computer system.

FIG. 32 schematically illustrates a computer system 1200 that can be used with the method. The computer system 1200 can be a laptop, desktop, server, handheld device (e.g., personal digital assistant (PDA), smart phone, etc.), programmable consumer or industrial electronic device. As shown, the computer system 1200 includes a processor 1202, which can be any various available microprocessors, e.g., the processor 1202 can be implemented as dual microprocessors, multi-core and other multiprocessor architectures.

The computer system 1200 includes memory 1204, which can include volatile memory and/or nonvolatile memory. Nonvolatile memory can include read only memory (ROM) for storage of basic routines for transfer of information, such as during computer boot or start-up. Volatile memory can include random access memory (RAM). The computer system can include storage media 1206, including but not limited to magnetic or optical disk drives, flash memory, and memory sticks.

The computer system 1200 incorporates one or more interfaces 1208, including ports (e.g., serial, parallel, PCM-CIA, USB, and FireWire) or interface cards (e.g., sound, video, network, etc.) or the like. In embodiments, an interface 1208 supports wired or wireless communications. Input is received from any number of input devices (e.g., keyboard, mouse, joystick, microphone, trackball, stylus, touch screen, scanner, camera, satellite dish, another computer system, etc.). The computer system 1200 outputs data through an output device, such as a display (e.g. CRT, LCD, plasma, etc.), speakers, printer, another computer or any other suitable output device.

Figure 33:
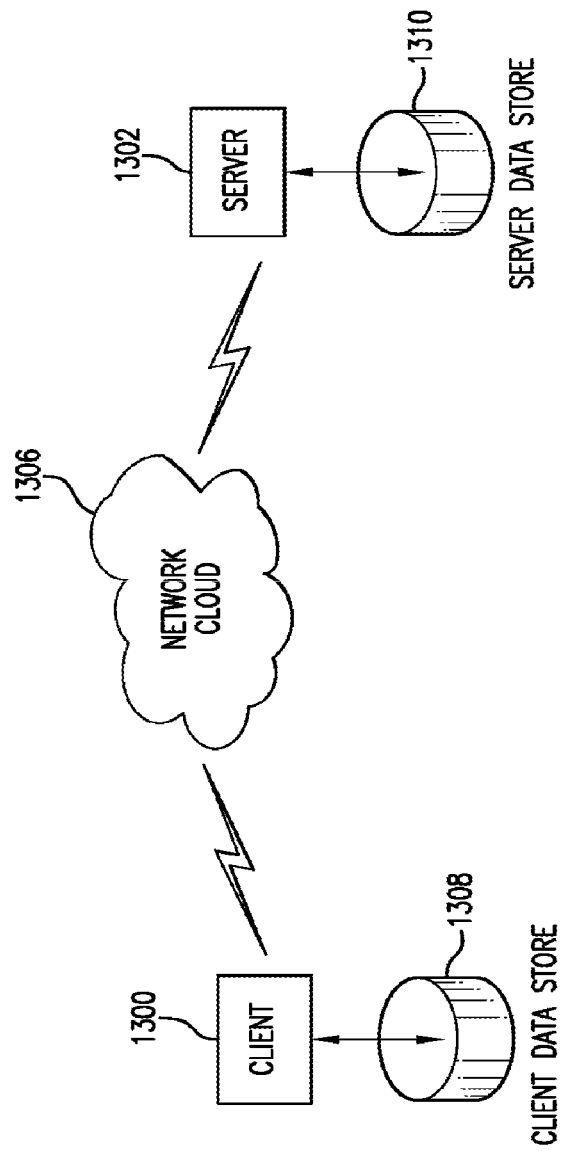
FIG. 33 shows an exemplary computing environment.

FIG. 33 schematically shows an exemplary computing environment for the disclosed systems and methods. The environment includes one or more clients 1300, where a client 1300 may be hardware (e.g., personal computer, laptop, handheld device, or other computing devices) or software (e.g., processes or threads). The environment also includes one or more servers 1302, where a server 1302 is software (e.g., thread or process) or hardware (e.g., computing devices), that provides a specific kind of service to a client 1300. The environment can support either a two-tier client server model as well as the multi-tier model (e.g., client, middle tier server, data server and other models).

The environment also includes a communication framework 1306 that enables communications between clients and servers. In one embodiment, clients correspond to local area network devices and servers are incorporated in a cloud computing system. A cloud is comprised of a collection of network accessible hardware and/or software resources. The environment can include client data stores 1308 that maintain local data and server data stores 1310 that store information local to the servers 1302.

In one embodiment, the method groups the following two sets of peptides into a sample for data analysis: a set of exogenous polypeptides related by identical amino acid sequences containing different numbers of heavy labeled isotopes, and a set of endogenous polypeptides related by the same amino acid sequences as defined by the exogenous group and lacking heavy labeled isotope addition. The method then calculates a quantity of each of the exogenous polypeptides and the endogenous polypeptides by processing the data using a processor. The processor automatically groups peptides containing identical amino acid sequences into groups differentiated by heavy labeled isotope inclusion, side chain modifications, and/or terminal modifications. For a sample, it determines a response for each exogenous polypeptide target, and correlates the response for each exogenous peptide as a function of a known quantity that generates a mathematical response linking a measured mass spectrometry signal and a quantity applied to the mass spectrometer; it determines the response for each endogenous polypeptide target, and calculates an estimated endogenous polypeptide target based on the mathematical expression correlated by the exogenous polypeptide analog. The steps are repeated for the remaining samples based on the correlated mathematical expression relating measured signal and/or AUC to an amount or quantity. Specifically, the measured ion intensity for the specified peptide amount on column or analyzed is plotted, generating generally linear results and permitting the linear response of the mass spectrometer for the targeted peptide to be calculated. The method then determines the endogenous amount by measuring the ion intensity or AUC, depending upon how the exogenous signal was measured. The amount is then entered into the linear equation as defined by the exogenous peptides to determine the amount on the column.

As disclosed, using the inventive universal reporter peptides, peptide sequences to be analyzed by MS methods are concatenated into a polypeptide analog. These concatenated subunits represent an isotopically labeled endogenous targeted peptide, labeled A* or A, belonging to a targeted protein, and the reporter peptide R that may or may not be isotopically labeled. Because the peptides are synthesized at a 1:1 ratio, upon enzymatic digestion, the signals can be referenced and absolute quantitation can be performed. Reporter peptide R has a different sequence than the endogenous peptides. Reporter peptide R contains the exact same sequence as the universal peptide U, which is differentiated from R by changing the number of isotopic labels from R. For example, with reporter peptide R having sequence TASEFDSAIAQDK where amino acid K is isotopically labeled, universal peptide U sequence could be TASEFDSAIAQDK where amino acids F and K are isotopically labeled.

For each of (i) the isotopically labeled endogenous targeted peptide A* or A, (ii) reporter peptide R, and (iii) universal peptide U, there are at least two m/z values that are targeted and that can be acquired using different mass spectral strategies. Each of the isoform pairs, or multiples, co-eluted.

The co-eluted isoform pairs, or multiples, were grouped for data acquisition using, in one embodiment, Q Exactive®, a bench-top high resolution quadrupole FT (Fourier transform)-MS system. Q Exactive® is based on existing high performance quadrupole and Exactive® bench-top Orbitrap technologies (Thermo Fisher Scientific) for ion detection, with an ion source interface (SRIG) lens, a quadrupole mass filer, and an improved high energy collision dissociation (HCD) cell with the Orbitrap analyzer; it also contains a higher scanning speed through optimization of parallel operation, multiplexed detection, and transient processing. Its ion source interface is a hybrid FT-MS fitted with a progressive stacked ring ion guide (SRIG) that provides better signal with less noise. Its quadrupole mass filter enables precursor ion selection before the curved linear ion trap (C-trap) cell, using four hyperbolic rods, $r_0$=4 mm. Fragmentation for true MS/MS operation is conducted in HCD cell, followed by C-trap ion injection into the Orbitrap for high resolution accurate mass detection; resolving power of the mass filter is 0.4 Da for ions <m/z 400, allowing highly specific precursor selection. The following table provides isolation widths at variable mass ranges:

| 50 < m/z < 400 | any isolation widths between 0.4 amu and full scan |
| 400 < m/z < 700 | any isolation widths between 0.7 amu and full scan |
| 700 < m/z < 1000 | any isolation widths between 1.0 amu and full scan |
| 1000 < m/z < 2000 | any isolation widths between 2.0 amu and full scan |
| >2000 m/z | no precursor ion isolation |

There is multiplexed detection; more than one, and up to 10, isolated precursor ions are collected before Orbitrap detection, significantly enhancing the duty cycle. The multiple secondary ion mass (SIM) mode enhances the duty cycle by a factor of N−1×transient acquisition time (N=number of precursors in one multiplex experiment). There is enhanced FT transient processing using an algorithm that enhances the resolving power by a factor of 1.8, yielding higher resolutions at higher acquisition speeds. The following table shows respective resolving power settings:

| Transient length (ms) | Resolving Power at m/z 200 | actual scan speed (Hz) |
|---|---|---|
| 64 | 17.500 | 12 |
| 128 | 35.000 | 7 |
| 256 | 70.000 | 3 |
| 512 | 140.000 | 1.5 |

The transfer optics and HCD collision cell are incorporated into a combination C-Trap and HCD collisions cell, providing an enhanced duty cycle for HCD MS/MS scans and improved low mass ion transmission to the Orbitrap. HCD transmission for ITraq and TMT tags are improved, resulting in improved S/N and quantitation in proteomic assays.

Using Q Exactive®, the quadrupole mass filter passes ions through towards the HCD cell and C-trap cell and can be set to filter discrete mass ranges. One setting passes a very narrow mass window (1 Da or 2 Da) centered on the individual mass isoform sequentially, and collecting in the C-trap cell prior to detection. One setting passes one limited mass range (10 Da) centered around the average mass value for the isoform grouping. One setting passes one larger mass range (>10 Da) to quantitate multiple groups simultaneously. One setting passes one extremely large mass range (200 Da-1000 Da) simulating a full scan MS analysis.

The HCD cell can be operated in high or low vacuum (relative) to either create low energy or high energy data collection. The C-trap collects, focuses, and injects into the orbitrap; the orbitrap is used for FT detection. FT detection simultaneously detects all ions in the orbitrap regardless of m/z value, it thus detects and quantitates the targeted peptides and their heavy labeled analogs. The quadrupole mass filter enables the Q Exactive® to pass a discrete mass range from the ion source region to the HCD cell, C-trap cell, and orbitrap mass spectrometer. The filtered mass window ranges from 0.4 Da to 4 Da, 10 Da, 50 Da, 100 Da, 200 Da, 500 Da, and larger, depending on the desired filtering window. By filtering the mass range transmitted from the source to the detector, the instrument increases detection capabilities by reducing background matrix ions from the orbitrap, thus increasing the charge density attributed to the targeted peptides.

The method of collecting targeted mass windows can be sequential, but detection and measuring ion abundance are simultaneous. This is distinguished from ion traps, triple quads, and TOF systems that do not collect discrete mass ranges prior to detection and do not have simultaneous detections. The latter instruments collect ions over either discrete mass ranges or detect over discrete mass ranges, but not both.

The method of ion accumulation is key to normalize the spectrum and relate ions of different abundance values. Targeted ions, both unlabeled and labeled analogs, are grouped in the instrument method editor prior to detection. This grouping links all aspects of data acquisition such as detection times, scheduled acquisition, automatic gain control, maximum ion fill times, etc., for improved evaluation. Setting the automatic gain control better normalizes the resulting data and provide a way to assign absolute quantities based on the spiked in levels of the synthetic peptides.

The method permits ion collection using low and/or high energy to collect and quantitate precursors ions or product ions. MS-level (low energy) is used for precursor detection and/or quantitation. MSn-level (high energy) (MSn denoting MS/MS, MS$^3$, etc.) is applicable to both endogenous and exogenous targets for quantitation and is used for product ion detection and measurement. Reducing the gas pressure in the HCD cell, and changing the voltage, activates ions passed through the quadrupole mass filter. If the mass filter is set to pass 2 Da windows centered around each independent member of a targeted group, the resulting product ions are independently formed. The user has the option to measure the tandem MS data independently, or to collect all product ions from the group and perform simultaneous detection. The mass filter can be set to pass wider mass ranges to simultaneously activate all ions as well as collect and measure ion abundance values.

Applicants incorporate by reference the material contained in the accompanying computer readable Sequence Listing entitled "078672_4.txt", which was created on Jul. 6, 2011 and is 32,125 bytes in size.

TABLE 1

| Heavy Peptide IGNIS ™ Name | Protein Name | Organism | Swissprot ID | Selected proteotypic peptides (PI, PII, PIII) | | |
|---|---|---|---|---|---|---|
| | | | | PI | PII | PIII |
| | uromodulin | human | P07911 | DWVSVVTPAR (SEQ ID NO. 49) | DSTIQVVENGESSQGR (SEQ ID NO. 50) | SGSVIDQSR (SEQ ID NO. 51) |
| TRFE | serotransferrin | human | P02787 | DGAGDVAFVK (SEQ ID NO. 54) | SASDLTWDNLK (SEQ ID NO. 55) | EGYYGYTGAFR (SEQ ID NO. 56) |
| LG3BP* | galectin-3-binding protein | human | Q08380 | LADGGATNQGR (SEQ ID NO. 58) | SDLAVPSELALLK (SEQ ID NO. 59) | ELSEALGQIFDSQR (SEQ ID NO. 60) |
| CD44 | CD44 antigen | human | P16070 | FAGVFHVEK (SEQ ID NO. 62) | YGFIEGHVVIPR (SEQ ID NO. 63) | ALSIGFETCR (SEQ ID NO. 64) |
| CATD | cathepsin d | human | P07339 | LVDQNIFSFYLSR (SEQ ID NO. 66) | VSTLPAITLK (SEQ ID NO. 67) | YSQAVPAVTEGPIPEVLK (SEQ ID NO. 68) |
| KNG1 | kininogen-1 | human | P01042 | TVGSDTFYSFK (SEQ ID NO. 70) | YFIDFVAR (SEQ ID NO. 71) | YNSQNQSNNQFVLYR (SEQ ID NO. 72) |
| ANAG | alpha-N-acetyl-glucosaminidase | human | P54802 | LLLTSAPSLATSPAFR (SEQ ID NO. 74) | YDLLDLTR (SEQ ID NO. 75) | SDVFEAWR (SEQ ID NO. 76) |
| ENO1 | enolase 1 | yeast | P00924 | NVNDVIAPAFVK (SEQ ID NO. 78) | LGANAILGVSLAASR (SEQ ID NO. 79) | TAGIQIVADDLTVTNPK (SEQ ID NO. 80) |
| CBPY | carboxypeptidase Y | yeast | P00729 | YDEEFASQK (SEQ ID NO. 82) | HFTYLR (SEQ ID NO. 83) | AWTDVLPWK (SEQ ID NO. 84) |
| ADH1 | alcohol dehydrogenase 1 | yeast | P00330 | GVIFYESHGK (SEQ ID NO. 86) | SIGGEVFIDFTK (SEQ ID NO. 87) | VVGLSTLPEIYEK (SEQ ID NO. 88) |

*no analysis performed

TABLE 2

| Heavy Peptide IGNIS™ name | Full sequence of isotopically labeled polypeptide + reporter peptide | PI | PII | PIII |
|---|---|---|---|---|
| UROM | DWVSVVTPARDSTIQVVENGESSQGRSGSVIDQSRLVALVR (SEQ ID NO. 53) | DWVSVVTPAR (SEQ ID NO. 49) | DSTIQVVENGESSQGR (SEQ ID NO. 50) | SGSVIDQSR (SEQ ID NO. 51) |
| TRFE | DGAGDVAFVKSASDLTWDNLKEGYYGYTGAFRLVALVR (SEQ ID NO. 57) | DGAGDVAFVK (SEQ ID NO. 54) | SASDLTWDNLK (SEQ ID NO. 55) | EGYYGYTGAFR (SEQ ID NO. 56) |
| LG3BP | LADGGATNQGRSDLAVPSELALLKELSEALGQIFDSQRLVALVR (SEQ ID NO. 61) | LADGGATNQGR (SEQ ID NO. 58) | SDLAVPSELALLK (SEQ ID NO. 59) | ELSEALGQIFDSQR (SEQ ID NO. 60) |
| CD44 | FAGVFHVEKYGFIEGHVVIPRALSIGFETCRLVALVR (SEQ ID NO. 65) | FAGVFHVEK (SEQ ID NO. 62) | YGFEGHVVIPR (SEQ ID NO. 63) | ALSIGFETCR (SEQ ID NO. 64) |
| CATD | LVDQNIFSFYLSRVSTLPAITLKYSQAVPAVTEGPIPEVLKLVALVR (SEQ ID NO. 69) | LVDQNIFSFYLSR (SEQ ID NO. 66) | VSTLPAITLK (SEQ ID NO. 67) | YSQAVPAVTEGPIPEVLK (SEQ ID NO. 68) |
| KNG1 | TVGSDTFYSFKYFIDFVARYNSQNQSNNQFVLYRLVALVR (SEQ ID NO. 73) | TVGSDTFYSFK (SEQ ID NO. 70) | YFIDFVAR (SEQ ID NO. 71) | YNSQNQSNNQFVLYR (SEQ ID NO. 72) |
| ANAG | LLLTSAPSLATSPAFRYDLLDLTRSDVFEAWRLVALVR (SEQ ID NO. 77) | LLLTSAPSLATSPAFR (SEQ ID NO. 74) | YDLLDLTR (SEQ ID NO. 75) | SDVFEAWR (SEQ ID NO. 76) |
| ENO1 | NVNDVIAPAFVKLGANAILGVSLAASRTAGIQIVADDLTVTNPKLVALVR (SEQ ID NO. 81) | NVNDVIAPAFVK (SEQ ID NO. 78) | LGANAILGVSLAASR (SEQ ID NO. 79) | TAGIQIVADDLTVTNPK (SEQ ID NO. 80) |
| CBPY | YDEEFASQKHFTYLRAWTDVLPWKLVALVR (SEQ ID NO. 85) | YDEEFASQK (SEQ ID NO. 82) | HFTYLR (SEQ ID NO. 83) | AWTDVLPWK (SEQ ID NO. 84) |
| ADH1 | GVIFYESHGKSIGGEVFIDFTKVVGLSTLPEIYEKLVALVR (SEQ ID NO. 89) | GVIFYESHGK (SEQ ID NO. 86) | SIGGEVFIDFTK (SEQ ID NO. 87) | VVGLSTLPEIYEK (SEQ ID NO. 88) |

TABLE 3

| Protein name | MM (Da) | Heavy proteotypic peptide sequence from HeavyPeptide IGNIS™ | Limit of detection fmol/μL peptide | Limit of detection Protein (ng/mL) | Limit of quantification fmol/μL peptide | Limit of quantification Protein (ng/mL) | Actual concentration measured fmol/μl of peptide | Actual concentration measured Protein (ng/mL) |
|---|---|---|---|---|---|---|---|---|
| Kininogen-1 (KNG1) (SEQ ID NO. 73) | 71,957 | TVGSDTFYSFK (SEQ ID NO. 70) | 0.02 | 1.30 | 0.05 | 3.89 | 197.65 | 14.22 |
| | | YFIDEVAR (SEQ ID NO. 71) | 0.05 | 3.89 | 0.16 | 11.66 | 223.71 | 16.10 |
| | | YNSQNQSNNQFVLYR (SEQ ID NO. 72) | 0.02 | 1.30 | 0.05 | 3.89 | 185.12 | 13.32 |

TABLE 4

Characterization of selected human and yeast HeavyPeptide IGNIS ™

| Name of universal reporter U | Proteotypic peptides (PI, PII, PIII) (order can be changed) | | | LVALVR Reporter R | Delta Mass vs. U | Natural sequence | Full sequence HeavyPeptide IGNIS ™ |
|---|---|---|---|---|---|---|---|
| | PI | PII | PIII | | | | |
| UROM | DWVSVVT PA*R (SEQ ID NO. 49) 11 | DSTIQVV *ENGESS QGR (SEQ ID NO. 50) 17 | SGSV*ID QSR (SEQ ID NO. 51) 10 | LVALVR* (SEQ ID NO. 52) 7 | Tot 45 | 10 | -6 | DWVSVVTPA*RDSTI QVV*ENGESSQGRSG SV*IDQSRLVALVR* (SEQ ID NO. 53) |
| TRFE | DGAGDVA *FVK (SEQ ID NO. 54) 11 | SA*SDLT WDNLK (SEQ ID NO. 55) 12 | EGYYGYT GA*FR (SEQ ID NO. 56) 12 | LV*ALV* R* (SEQ ID NO. 52) 9 | 22 44 | 6 | | DGAGDVA*FVKSA*S DLTWDNLKEGYYGYT GA*FRLV*ALV*R* (SEQ ID NO. 57) |
| LG3BP | LADGGA* TNQGR (SEQ ID NO. 58) 12 | SDLAVPS ELA*LLK (SEQ ID NO. 59) 14 | ELSEA*L GQIFDSQ R (SEQ ID NO. 60) 15 | LVA*L*V *R* (SEQ ID NO. 52) 10 | 51 | 27 | 11 | LADGGA*TNQGRSDL AVPSELA*LLKELSE A*LGQIFDSQRLVA* L*V*R* (SEQ ID NO. 61) |
| CD44 | FA*GVFH VEK (SEQ ID NO. 62) 10 | YGFIEGH VV*IPR (SEQ ID NO. 63) 13 | A*LSIGF ETCR (SEQ ID NO. 64) 11 | LV*A*L* V*R* (SEQ ID NO. 52) 11 | 45 | 33 | 17 | FA*GVFHVEKYGFIE GHVV*IPRA*LSIGF ETCRLV*A*L*V*R* (SEQ ID NO. 65) |
| CATD | LV*DQNI FSFYLSR (SEQ ID NO. 66) 14 | VSTLPA* ITLK (SEQ ID NO. 67) 11 | YSQAVPA *VTEGPI PEVLK (SEQ ID NO. 68) 19 | L*V*A*L *V*R* (SEQ ID NO. 52) 12 | 56 | 40 | 24 | LV*DQNIFSFYLSRV STLPA*ITLKYSQAV PA*VTEGPIPEVLKL *V*A*L*V*R* (SEQ ID NO. 69) |
| KNG1 | TV*GSDT FYSFK (SEQ ID NO. 70) 13 | YFIDFVA *R (SEQ ID NO. 71) 10 | YNSQNQS NNQFV*L YR (SEQ ID NO. 72) 17 | LVA*LVR (SEQ ID NO. 52) 7 | 47 | 4 | -12 | TV*GSDTFYSFKYFI DFVA*RYNSQNQSNN QFV*LYRLVA*LVR (SEQ ID NO. 73) |
| ANAG | LLLTSAP SLATSPA *FR (SEQ ID NO. 74) 17 | YDLLDL* TR (SEQ ID NO. 75) 9 | SDV*FEA WR (SEQ ID NO. 76) 9 | LVALVR (SEQ ID NO. 52) 6 | 41 | 0 | -16 | LLLTSAPSLATSPA* FRYDLLDL*TRSDV* FEAWRLVALVR (SEQ ID NO. 77) |
| ENO1_V2 | NVNDVIA PA*FVK (SEQ ID NO. 78) 13 | LGANAIL GVSLAA* SR (SEQ ID NO. 79) 16 | TAGIQIV A*DDLTV TNPK (SEQ ID NO. 80) 18 | L*VA*L* VR (SEQ ID NO. 52) 9 | 56 | 20 | 4 | NVNDVIAPA*FVKLG ANAILGVSLAA*SRT AGIQIVA*DDLTVTN PKL*VA*L*VR (SEQ ID NO. 81) |
| CBPY_V2 | YDEEFA* SQK (SEQ ID NO. 82) 10 | HFTYL*R (SEQ ID NO. 83) 8 | A*WTDVL PWK (SEQ ID NO. 84) 10 | L*VALV* R (SEQ ID NO. 52) 8 | 36 | 13 | -3 | YDEEFA*SQKHFTYL *R*A*WTDVLPWKL* VALV*R (SEQ ID NO. 85) |
| ADH1_V2 | GV*IFYE SHGK* (SEQ ID NO. 86) 12 | SIGGEV* FIDFTK (SEQ ID NO. 87) 14 | V*VGLST LPEIYEK* (SEQ ID NO. 88) 15 | LVA*LVR (SEQ ID NO. 52) 7 | 48 | 4 | -12 | GV*IFYESHGK*SIG GEV*FIDFTK*V*VG LSTLPEIYEK*LVA* LVR (SEQ ID NO. 89) |

TABLE 5

| Aqua Ultimate peptides (>97%) with labeled 13C, 15N | Name | SEQ ID NO. |
|---|---|---|
| LGANAILGVSLAASR* | ENO1_A | 79 |
| TAGIQIVADDLTVTNPK* | ENO1_B | 80 |
| YDEEFASQK* | CBPY_A | 82 |
| HFTYLR* | CBPY_B | 83 |
| GVIFYESHGK* | ADH1_A | 86 |
| DWVSVVTPAR* | UROM_A | 49 |
| DSTIQVVENGESSQGR* | UROM_B | 50 |
| SGSVIDQSR* | UROM_C | 51 |
| DGAGDVAFVK* | TRFE_A | 54 |
| SASDLTWDNLK* | TRFE_B | 55 |
| EGYYGYTGAFR* | TRFE_C | 56 |
| LADGGATNQGR* | LG3BP_A | 58 |
| SDLAVPSELALLK* | LG3BP_B | 59 |
| ELSEALGQIFDSQR* | LG3BP_C | 60 |
| FAGVFHVEK* | CD44_A | 62 |
| YGFIEGHVVIPR* | CD44_B | 63 |
| ALSIGFETCR* | CD44_C | 64 |
| LVDQNIFSFYLSR* | CATD_A | 66 |
| VSTLPAITLK* | CATD_B | 67 |
| YSQAVPAVTEGPIPEVLK* | CATD_C | 68 |
| TVGSDTFYSFK* | KNG1_A | 70 |
| YFIDFVAR* | KNG1_B | 71 |
| YNSQNQSNNQFVLYR* | KNG1_C | 72 |
| LLLTSAPSLATSPAFR* | ANAG_A | 74 |
| YDLLDLTR* | ANAG_B | 75 |
| SDVFEAWR* | ANAG_C | 76 |

The embodiments shown and described in the specification are only specific embodiments of the inventor who is skilled in the art and is not limiting in any way. Therefore, various changes, modifications, or alterations to those embodiments may be made without departing from the spirit of the invention in the scope of the following claims.

What is claimed is:

1. A method of assessing sensitivity limits of MS equipment, the method comprising generating a dilution curve in a single injection into a liquid chromatograph/mass spectrometer by injecting into a first liquid chromatography (LC) column coupled to a mass spectroscopy detection system a single peptide composition, the single peptide composition comprising a composition comprising at least a first set of a plurality of peptide isotopologues, where each peptide isotopologue of the first set has the same amino acid sequence; each peptide isotopologue of the first set has a different mass; and each peptide isotopologue of the first set is present at a different concentration;

analyzing each peptide in the co-eluted peptide composition by mass spectroscopy;

generating from the single peptide composition injection into the LC column at least a first dilution curve from the analysis; and using results of the at least first dilution curve to assess sensitivity of the MS equipment.

2. The method of claim 1 where sensitivity is assessed by determining at least one of limits of detection (LOD) or limits of quantitation (LOQ).

3. The method of claim 1 where concentration range of the peptide isotopologues in a set span at least 3 logarithmic range.

4. The method of claim 1 where the assessed sensitivity limits are used to compare at least one of limits of detection (LOD) or limits of quantitation (LOQ) from at least one of instrument to instrument, brand to brand, or day to day on the same instrument.

* * * * *

SEQUENCE LISTING

<160> NUMBER OF SEQ ID NOS: 92

<210> SEQ ID NO 1
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Pro Val Val Val Pro Arg
1               5

<210> SEQ ID NO 2
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Ser Ser Ala Ala Pro Pro Pro Pro Arg
1               5                   10

<210> SEQ ID NO 3
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 3

Thr Thr Val Ser Lys Thr Glu Thr Ser Gln Val Ala Pro Ala
1               5                   10

<210> SEQ ID NO 4
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Thr Glu Thr Ser Gln Val Ala Pro Ala
1               5

<210> SEQ ID NO 5
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Thr Thr Val Ser Lys
1               5

<210> SEQ ID NO 6
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gly Ile Ser Asn Glu Gly Gln Asn Ala Ser Ile Lys
1               5                   10

<210> SEQ ID NO 7
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

His Val Leu Thr Ser Ile Gly Glu Lys
1               5

<210> SEQ ID NO 8
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Asp Ile Pro Val Pro Lys Pro Lys
```

-continued

<210> SEQ ID NO 9
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Ile Gly Asp Tyr Ala Gly Ile Lys
1               5

<210> SEQ ID NO 10
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Thr Ala Ser Glu Phe Asp Ser Ala Ile Ala Gln Asp Lys
1               5                   10

<210> SEQ ID NO 11
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Ser Ala Ala Gly Ala Phe Gly Pro Glu Leu Ser Arg
1               5                   10

<210> SEQ ID NO 12
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Glu Leu Gly Gln Ser Gly Val Asp Thr Tyr Leu Gln Thr Lys
1               5                   10

<210> SEQ ID NO 13
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Ser Phe Ala Asn Gln Pro Leu Glu Val Val Tyr Ser Lys
1               5                   10

<210> SEQ ID NO 14

```
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Gly Leu Ile Leu Val Gly Gly Tyr Gly Thr Arg
1               5                   10

<210> SEQ ID NO 15
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Gly Ile Leu Phe Val Gly Ser Gly Val Ser Gly Glu Glu Gly Ala
1               5                   10                  15

Arg

<210> SEQ ID NO 16
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Leu Thr Ile Leu Glu Glu Leu Arg
1               5

<210> SEQ ID NO 17
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Asn Gly Phe Ile Leu Asp Gly Phe Pro Arg
1               5                   10

<210> SEQ ID NO 18
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Glu Leu Ala Ser Gly Leu Ser Phe Pro Val Gly Phe Lys
1               5                   10

<210> SEQ ID NO 19
<211> LENGTH: 14
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Leu Ser Ser Glu Ala Pro Ala Leu Phe Gln Phe Asp Leu Lys
1               5                   10

<210> SEQ ID NO 20
<211> LENGTH: 40
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
            35                  40

<210> SEQ ID NO 21
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
            35                  40

<210> SEQ ID NO 22
<211> LENGTH: 43
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr
            35                  40

<210> SEQ ID NO 23
<211> LENGTH: 46
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 23

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr Val Ile Val
        35                  40                  45

<210> SEQ ID NO 24
<211> LENGTH: 40
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Asp Ala Glu Trp Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 25
<211> LENGTH: 40
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Asp Ala Glu Phe Arg His Asp Ser Gly Trp Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 26
<211> LENGTH: 40
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Asp Ala Glu Phe Arg His Asp Ser Gly Tyr Glu Val His His Gln Lys
1               5                   10                  15

Leu Val Phe Phe Ala Glu Asn Val Gly Ser Asn Lys Gly Ala Ile Ile
            20                  25                  30

Gly Leu Met Val Gly Gly Val Val
        35                  40
```

<210> SEQ ID NO 27
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 27

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Val Val Gly Gly Val Val Ile Ala
        35                  40
```

<210> SEQ ID NO 28
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 28

```
Asp Ala Glu Phe Gly His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40
```

<210> SEQ ID NO 29
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 29

```
Asp Ala Glu Phe Arg His Asp Ser Gly Ala Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40
```

<210> SEQ ID NO 30
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 30

```
Asp Ala Glu Trp Arg His Asp Ser Gly Tyr Glu Val His His Gln Lys
1               5                   10                  15

Leu Val Phe Phe Ala Glu Asp Val Gly Ser Asn Lys Gly Ala Ile Ile
```

-continued

```
            20                  25                  30

Gly Leu Met Val Gly Gly Val Val Ile Ala
        35                  40

<210> SEQ ID NO 31
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Asp Ala Glu Phe Arg Ala Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 32
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Asp Ala Glu Phe Arg His Asp Ser Gly Tyr Glu Val Ala His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 33
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Asp Ala Glu Phe Arg His Asp Ser Gly Tyr Glu Val His Ala Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 34
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34
```

```
Asp Ala Glu Phe Arg His Asp Ser Gly Tyr Glu
1               5                   10
```

<210> SEQ ID NO 35
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

```
Asp Ala Glu Phe Arg His Asp Ser Gly Tyr Glu Val His His Gln Lys
1               5                   10                  15
```

<210> SEQ ID NO 36
<211> LENGTH: 28
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys
            20                  25
```

<210> SEQ ID NO 37
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly
        35
```

<210> SEQ ID NO 38
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

```
Glu Val His His Gln Lys Leu Val Phe Phe Ala Glu
1               5                   10
```

<210> SEQ ID NO 39
<211> LENGTH: 21
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 39

Glu Val His His Gln Lys Leu Val Phe Phe Ala Glu Asp Val Gly Ser
1               5                   10                  15

Asn Lys Gly Ala Ile
            20

<210> SEQ ID NO 40
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Glu Val His His Gln Lys Leu Val Phe Phe Ala Glu Asp Val Gly Ser
1               5                   10                  15

Asn Lys Gly Ala Ile Ile Gly Leu Met Val Gly Gly Val Val
            20                  25                  30

<210> SEQ ID NO 41
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Val His His Gln Lys Leu Val Phe Phe Ala Glu Asp Val Gly Ser Asn
1               5                   10                  15

Lys

<210> SEQ ID NO 42
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Leu Val Phe Phe Ala Glu Asp Val Gly Ser Asn Lys Gly Ala Ile Ile
1               5                   10                  15

Gly Leu Met Val Gly Gly Val Val
            20

<210> SEQ ID NO 43
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Leu Val Phe Phe Ala Glu Asp Val Gly Ser Asn Lys Gly Ala Ile Ile
1               5                   10                  15
```

```
Gly Leu Met Val Gly Gly Val Val Ile Ala
            20                  25

<210> SEQ ID NO 44
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Glu Asp Val Gly Ser Asn Lys Gly Ala Ile Ile Gly Leu Met
1               5                   10

<210> SEQ ID NO 45
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Gly Ser Asn Lys Gly Ala Ile Ile Gly Leu Met
1               5                   10

<210> SEQ ID NO 46
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

His Glu Val Thr Gly Trp Val Leu Val Ser Pro Leu Ser Lys
1               5                   10

<210> SEQ ID NO 47
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Ile Thr Val Val Asp Ala Leu His Glu Ile Pro Val Lys
1               5                   10

<210> SEQ ID NO 48
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Leu Val Ala Leu Val Arg
1               5
```

```
<210> SEQ ID NO 49
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Asp Trp Val Ser Val Val Thr Pro Ala Arg
1               5                   10

<210> SEQ ID NO 50
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Asp Ser Thr Ile Gln Val Val Glu Asn Gly Glu Ser Ser Gln Gly Arg
1               5                   10                  15

<210> SEQ ID NO 51
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Ser Gly Ser Val Ile Asp Gln Ser Arg
1               5

<210> SEQ ID NO 52
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Leu Val Ala Leu Val Arg
1               5

<210> SEQ ID NO 53
<211> LENGTH: 41
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Asp Trp Val Ser Val Val Thr Pro Ala Arg Asp Ser Thr Ile Gln Val
1               5                   10                  15

Val Glu Asn Gly Glu Ser Ser Gln Gly Arg Ser Gly Ser Val Ile Asp
            20                  25                  30

Gln Ser Arg Leu Val Ala Leu Val Arg
```

<210> SEQ ID NO 54
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 54

Asp Gly Ala Gly Asp Val Ala Phe Val Lys
1               5                   10

<210> SEQ ID NO 55
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 55

Ser Ala Ser Asp Leu Thr Trp Asp Asn Leu Lys
1               5                   10

<210> SEQ ID NO 56
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 56

Glu Gly Tyr Tyr Gly Tyr Thr Gly Ala Phe Arg
1               5                   10

<210> SEQ ID NO 57
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 57

Asp Gly Ala Gly Asp Val Ala Phe Val Lys Ser Ala Ser Asp Leu Thr
1               5                   10                  15

Trp Asp Asn Leu Lys Glu Gly Tyr Tyr Gly Tyr Thr Gly Ala Phe Arg
            20                  25                  30

Leu Val Ala Leu Val Arg
        35

<210> SEQ ID NO 58
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 58

```
Leu Ala Asp Gly Gly Ala Thr Asn Gln Gly Arg
1               5                   10

<210> SEQ ID NO 59
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Ser Asp Leu Ala Val Pro Ser Glu Leu Ala Leu Leu Lys
1               5                   10

<210> SEQ ID NO 60
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Glu Leu Ser Glu Ala Leu Gly Gln Ile Phe Asp Ser Gln Arg
1               5                   10

<210> SEQ ID NO 61
<211> LENGTH: 44
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 61

Leu Ala Asp Gly Gly Ala Thr Asn Gln Gly Arg Ser Asp Leu Ala Val
1               5                   10                  15

Pro Ser Glu Leu Ala Leu Leu Lys Glu Leu Ser Glu Ala Leu Gly Gln
            20                  25                  30

Ile Phe Asp Ser Gln Arg Leu Val Ala Leu Val Arg
        35                  40

<210> SEQ ID NO 62
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Phe Ala Gly Val Phe His Val Glu Lys
1               5

<210> SEQ ID NO 63
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 63

Tyr Gly Phe Ile Glu Gly His Val Val Ile Pro Arg
1               5                   10

<210> SEQ ID NO 64
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Ala Leu Ser Ile Gly Phe Glu Thr Cys Arg
1               5                   10

<210> SEQ ID NO 65
<211> LENGTH: 37
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 65

Phe Ala Gly Val Phe His Val Glu Lys Tyr Gly Phe Ile Glu Gly His
1               5                   10                  15

Val Val Ile Pro Arg Ala Leu Ser Ile Gly Phe Glu Thr Cys Arg Leu
            20                  25                  30

Val Ala Leu Val Arg
        35

<210> SEQ ID NO 66
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Leu Val Asp Gln Asn Ile Phe Ser Phe Tyr Leu Ser Arg
1               5                   10

<210> SEQ ID NO 67
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Val Ser Thr Leu Pro Ala Ile Thr Leu Lys
1               5                   10

<210> SEQ ID NO 68
<211> LENGTH: 18
<212> TYPE: PRT
<213> ORGANISM: Artificial Sequence
<220> FEATURE:
<221> NAME/KEY: source
```

<223> OTHER INFORMATION: /note="Description of Artificial Sequence:
     Synthetic peptide"

<400> SEQUENCE: 68

Tyr Ser Gln Ala Val Pro Ala Val Thr Glu Gly Pro Ile Pro Glu Val
1               5                   10                  15

Leu Lys

<210> SEQ ID NO 69
<211> LENGTH: 47
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 69

Leu Val Asp Gln Asn Ile Phe Ser Phe Tyr Leu Ser Arg Val Ser Thr
1               5                   10                  15

Leu Pro Ala Ile Thr Leu Lys Tyr Ser Gln Ala Val Pro Ala Val Thr
            20                  25                  30

Glu Gly Pro Ile Pro Glu Val Leu Lys Leu Val Ala Leu Val Arg
        35                  40                  45

<210> SEQ ID NO 70
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 70

Thr Val Gly Ser Asp Thr Phe Tyr Ser Phe Lys
1               5                   10

<210> SEQ ID NO 71
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 71

Tyr Phe Ile Asp Phe Val Ala Arg
1               5

<210> SEQ ID NO 72
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 72

Tyr Asn Ser Gln Asn Gln Ser Asn Asn Gln Phe Val Leu Tyr Arg
1               5                   10                  15

<210> SEQ ID NO 73
<211> LENGTH: 40

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

Thr Val Gly Ser Asp Thr Phe Tyr Ser Phe Lys Tyr Phe Ile Asp Phe
1               5                   10                  15

Val Ala Arg Tyr Asn Ser Gln Asn Gln Ser Asn Asn Gln Phe Val Leu
            20                  25                  30

Tyr Arg Leu Val Ala Leu Val Arg
        35                  40

<210> SEQ ID NO 74
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Leu Leu Leu Thr Ser Ala Pro Ser Leu Ala Thr Ser Pro Ala Phe Arg
1               5                   10                  15

<210> SEQ ID NO 75
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Tyr Asp Leu Leu Asp Leu Thr Arg
1               5

<210> SEQ ID NO 76
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Ser Asp Val Phe Glu Ala Trp Arg
1               5

<210> SEQ ID NO 77
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 77

Leu Leu Leu Thr Ser Ala Pro Ser Leu Ala Thr Ser Pro Ala Phe Arg
1               5                   10                  15

Tyr Asp Leu Leu Asp Leu Thr Arg Ser Asp Val Phe Glu Ala Trp Arg
```

Leu Val Ala Leu Val Arg
        35

<210> SEQ ID NO 78
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Asn Val Asn Asp Val Ile Ala Pro Ala Phe Val Lys
1               5                   10

<210> SEQ ID NO 79
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Leu Gly Ala Asn Ala Ile Leu Gly Val Ser Leu Ala Ala Ser Arg
1               5                   10                  15

<210> SEQ ID NO 80
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Thr Ala Gly Ile Gln Ile Val Ala Asp Asp Leu Thr Val Thr Asn Pro
1               5                   10                  15

Lys

<210> SEQ ID NO 81
<211> LENGTH: 50
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

Asn Val Asn Asp Val Ile Ala Pro Ala Phe Val Lys Leu Gly Ala Asn
1               5                   10                  15

Ala Ile Leu Gly Val Ser Leu Ala Ala Ser Arg Thr Ala Gly Ile Gln
            20                  25                  30

Ile Val Ala Asp Asp Leu Thr Val Thr Asn Pro Lys Leu Val Ala Leu
        35                  40                  45

Val Arg
    50

<210> SEQ ID NO 82
<211> LENGTH: 9

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82

Tyr Asp Glu Glu Phe Ala Ser Gln Lys
1               5

<210> SEQ ID NO 83
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

His Phe Thr Tyr Leu Arg
1               5

<210> SEQ ID NO 84
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 84

Ala Trp Thr Asp Val Leu Pro Trp Lys
1               5

<210> SEQ ID NO 85
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

Tyr Asp Glu Glu Phe Ala Ser Gln Lys His Phe Thr Tyr Leu Arg Ala
1               5                   10                  15

Trp Thr Asp Val Leu Pro Trp Lys Leu Val Ala Leu Val Arg
            20                  25                  30

<210> SEQ ID NO 86
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

Gly Val Ile Phe Tyr Glu Ser His Gly Lys
1               5                   10

<210> SEQ ID NO 87
<211> LENGTH: 12
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 87

Ser Ile Gly Gly Glu Val Phe Ile Asp Phe Thr Lys
1               5                   10

<210> SEQ ID NO 88
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

Val Val Gly Leu Ser Thr Leu Pro Glu Ile Tyr Glu Lys
1               5                   10

<210> SEQ ID NO 89
<211> LENGTH: 41
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 89

Gly Val Ile Phe Tyr Glu Ser His Gly Lys Ser Ile Gly Gly Glu Val
1               5                   10                  15

Phe Ile Asp Phe Thr Lys Val Val Gly Leu Ser Thr Leu Pro Glu Ile
                20                  25                  30

Tyr Glu Lys Leu Val Ala Leu Val Arg
            35                  40

<210> SEQ ID NO 90
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 90

Glu Val Gly Val Gly Phe Ala Thr Arg
1               5

<210> SEQ ID NO 91
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 91

His Glu Val Thr Gly Trp Val Leu Val Ser Pro Leu Ser Lys
1               5                   10

<210> SEQ ID NO 92
```

```
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 92

Ile Thr Val Val Asp Ala Leu His Glu Ile Pro Val Lys
1               5                   10
```